United States Patent [19]
Chen et al.

[11] Patent Number: 6,004,939
[45] Date of Patent: Dec. 21, 1999

[54] METHODS FOR MODULATION AND INHIBITION OF TELOMERASE

[75] Inventors: Shih-Fong Chen; Ira Maine, both of San Antonio; Sean M. Kerwin, Round Rock; Terace M. Fletcher, San Antonio; Miquel Salazar; Blain Mamiya, both of Austin; Makoto Wajima; Bradford E. Windle, both of San Antonio, all of Tex.

[73] Assignees: CTRC Research Foundation Board of Regents, San Antonio, Tex.; The University of Texas System, Austin, Tex.

[21] Appl. No.: 08/879,457

[22] Filed: Jun. 20, 1997

Related U.S. Application Data

[63] Continuation-in-part of application No. 08/675,119, Jul. 3, 1996
[60] Provisional application No. 60/000,927, Jul. 6, 1995.
[51] Int. Cl.$^6$ .................................................. A61K 31/70
[52] U.S. Cl. .............................. 514/43; 514/45; 514/48; 536/23.1; 536/24.5; 536/26.23; 536/26.26; 536/26.7; 536/27.8; 536/27.81
[58] Field of Search ..................... 514/43, 45; 536/23.1, 536/24.5, 26.23, 26.26, 26.7, 27.8, 27.81; 435/6

[56] References Cited

U.S. PATENT DOCUMENTS

| | | | |
|---|---|---|---|
| 5,091,310 | 2/1992 | Innis | 435/91 |
| 5,446,139 | 8/1995 | Seela et al. | 536/26.7 |
| 5,480,980 | 1/1996 | Seela | 536/23.1 |
| 5,489,508 | 2/1996 | West et al. | 435/6 |
| 5,654,286 | 8/1997 | Hostetler | 514/47 |
| 5,656,638 | 8/1997 | Gaeta et al. | 514/301 |
| 5,661,148 | 8/1997 | Sakuma et al. | 514/218 |

FOREIGN PATENT DOCUMENTS

| | | |
|---|---|---|
| 0286028 | 10/1988 | European Pat. Off. |
| 0666313 | 8/1995 | European Pat. Off. |
| 3529478 | 2/1987 | Germany. |
| WO94/08053 | 4/1994 | WIPO. |
| WO95/13381 | 5/1995 | WIPO. |
| WO96/12821 | 5/1996 | WIPO. |
| 9702279 | 1/1997 | WIPO. |

OTHER PUBLICATIONS

Allshire et al., "Human telomeres contain at least three types of G–rich repeat distributed non–randomly," *Nucleic Acids Res.*, 17(12):4611–4627, 1989.

Allsopp et al., "Telomere length predicts replicative capacity of human firbroblasts," *Proc. Natl. Acad., Sci. USA*, 89:10114–10118, 1992 (Nov. 1992).

Bahler et al., Chromosoma 103, 129–141, 1994.

Balagutumoorthy and Brahmachari, *J. Biol. Chem.* 269, 21858–21869, 1994 Aug. 26, 1994.

Baroin et al., "Telomeric site position heterogeneity in macronuclear DNA of *Paramecium primaurelia*," *Nucleic Acids Res.*, 15(4):1717–1728, 1987.

Blackburn, "Telomerases," *Annu. Rev. Biochem.*, 61:113–129, 1992.

Blackburn, "Telomeres sans frontières," *Nature*, 343(11):122, 1990 (Jan. 1, 1990).

Blackburn, "Telomeres: Structure and Synthesis," *J. Biol. Chem.*, 265(11):5919–5921, 1990 (Apr. 15, 1990).

Blackburn, "Telomeres and their synthesis," *Science*, 249:489–490, 1990 (Aug. 3, 1990).

Budarf and Blackburn, "S1 nuclease sensitivity of a double–stranded telomeric DNA sequence," *Nucleic Acids Res.*, 15(15):6273–6292, 1987.

Carlson et al., "Evolution of the dispersed SUC gene family of Saccharomyces by rearrangements of chromosome telomeres," *Mol. Cell Biol.*, 5(11):2894–2902, (Nov. 1985).

Chadeneau et al., *Cancer Res.*, 55:2533–2536, (Jun. 15, 1995).

Challoner and Blackburn, "Conservation of sequences adjacent to the telomeric $C_4A_2$ repeats of ciliate macronuclear ribosomal RNA gene molecules," *Nucleic Acids Res.*, 14(15):6299–6311, 1986.

Cherry and Blackburn, "The internally located telomeric sequences in the germ–line chromosomes of tetrahymena are at the ends of transposon–like elements," *Cell*, 43:747–758:(Dec. 1985).

Chong et al., "A human telomeric protein," *Science*, 270:1663–1667, Dec. 8, 1995.

Collins and Greider, "Utilization of ribonucleotides and RNA primers by Tetrahymena telomerase," *EMBO J.*, 14:5422–5432, 1995.

(List continued on next page.)

*Primary Examiner*—Marian Knode
*Assistant Examiner*—L. Eric Crane
*Attorney, Agent, or Firm*—Arnold, White & Durkee

[57] ABSTRACT

It was found that normal human stem cells produce a regulated non-processive telomerase activity, while cancer cells produce a processive telomerase activity. Nucleotide analogs, such as 7-deaza-2'-deoxyquanosine-5'-triphosphate (7-deaza-dGTP) were found to be substrates for processive telomerase and incorporated into telomeric sequence. The incorporation of this nucleotide subsequently affected the processivity of telomerase, converting processive telomerase to non-processive telomerase. The incorporation of this nucleotide analogs was also found to inhibit formation of G-quartets by telomeric sequence. Other methods for converting cancer processive telomerase to the more benign non-processive telomerase include partially cleaving the telomerase RNA. The nucleoside analogs were found to be capable of a variety of activities including mediating allosteric-like inhibition of telomerase, premature termination and shortening of telomeric DNA, destabilization of telomeric structure and function and eventually cell death. Understanding the mechanisms of telomerase modulation by the 7-deazanucleotides has allowed the design of new telomerase inhibitors, modulators and agents for affecting telomere structure and function. These discoveries have application in the treatment of cancer.

16 Claims, 9 Drawing Sheets

OTHER PUBLICATIONS

Cohn and Blackburn, "Telomerase in yeast," *Science* 269, 396–400, (Jul. 21, 1995).

Counter et al., "Telomerase activity in human ovarian carcinoma," *Proc. Natl. Acad. Sci.*, 91:2900–2904, (Apr., 1994).

Counter et al., "Telomere shortening associated with chromosome instability is arrested in immortal cells which express telomerase activity," *EMBO J.*, 11:1921–1929, 1992.

Counter et al. "Telomerase activity in normal leukocytes and in hematologic malignancies," *Blood,* 85:2315–2320, (May 1, 1995).

Doggett et al., "The Huntington disease locus is most likely within 325 kilobases of the chromosome 4p telomere," *Proc. Natl. Acad. Sci. USA,* 86:10011–10014, (Dec. 1989).

Dunn et al., "Transfer of yeast telomeres to linear plasmids by recombination," *Cell,* 39:191–201, (Nov. 1984).

Game, "Use of a ring chromosome and pulsed–field gels to study interhomolog recombination, double–strand DNA breaks and sister–chromatid exchange in yeast," *Genetics,* 123:695–713, (Dec. 1989).

Seela et al., "3'–Substituted and 2',3'–Unsaturated 7–Deazaguanine 2',3'–Dideoxynucleosides: Syntheses and Inhibition of HIV–1 Reverse Transcriptase," *Helv. Chim. Acta,* 74(5), 1081–1090 (Aug. 7, 1991).

Seela et al., "Syntheses of Pyrrolo[2,3–d]pyrimidine 2',3'–Dideoxyribonucleosides Related to 2',3'–Dideoxyadenosoine and 2',3'–Dideoxyguanosine and Inhibitory Activity of 5'–Triphosphates on HIV–1 Reverse Transcriptase," *Helv. Chim. Acta.* 74(3), 554–564 (May 2, 1991).

Fletcher et al., "Human Telomerase Inhibition by 7–Deaza–2'–deoxypurine Nucleoside Triphosphates," *Biochemistry,* 35(49), 15611–15617 (Dec. 10, 1996).

Tonomura et al., "Interaction Between Synthetic ATP Analogues and Actomyosin Systems. IV," *J. Biochemistry* (Japan), 61(4), 460–472 (Apr. 1967).

Kapuler et al., "Utilization of Substrate Analogs by Mengovirus Induced RNA Polymerase ," *Virology,* 37(4), 701–706 (Apr. 1969).

Vila et al., "Absence of Viral Rebound After Treatment of HIV–Infected Patients with Didanosine [ddI] and Hydroxycarbamide [Hydroxyurea]," *Lancet,* 350(9078), 635–636 (Aug. 30, 1997).

Strahl et al. (I), "The Effects of Nucleoside Analogs on Telomerase and Telemeres and in Tetrahymena," *Nucleic Acids Research,* 22(6), 893–900 (1994).

Strahl et al. (II), "Effects of Reverse Transcriptase Inhibitors on Telomere Length and Telomerase Activity in Two Immortal Human Cell Lines," *Mol. and Cell Biol.,* 16, 53–65 (Jan. 1996).

Zakian and Blanton, Distribution of telomere–associated sequences on natural chromosomes in *Saccharomyces cerevisiae, Mol. Cell. Biol.,* 8(5):2257–2260, (May 1988).

Zakian and Pluta, "Telomere formation in yeast," *Nature,* 338:468, Apr. 6, 1989).

Zakian, "Structure and function of telomeres," *Annu. Rev. Genet.,* 23:579–604, 1989.

Zakian, "Telomeres: Beginning to understand the end" *Science,* 270:1601–1607, 1995 (Feb. 1995).

Fletcher and Chen, "The effect of 7–deaza–2'–deoxyguanosine–5'–triphoshate and 7–deaza–2'–deoxyadenosine–5'–triphoshpate on telomerase activity," EORTC, Proceedings of the 9th NCI–EORTC Symposium on New Drugs in Cancer Therapy, Amsterdam, Netherlands, p. 71, Abstract No. 241, Mar. 12–15, 1996.

Fletcher and Chen, "The effect of 7–deaza–2'–deoxynucleoside triphosphates on telomeres and telomerase," *Proc. Am. Assoc. Cancer Res.,* 37:562, Abstract #3857, (Apr. 21, 1996).

Fletcher and Hansen, "Core histone tail domains mediate oligonucleosome folding and nucleosomal DNA organization through distinct molecular mechanisms," *J. Biol. Chem.,* 270(43):25359–25362, (Oct. 27, 1995).

Fletcher et al., "Human telomerase inhibition by 7–deaza–2'–deoxypurine nucleoside triphosphates," *Biochem.,* 35(49):15611–15617, (Dec. 10, 1996).

Fletcher et al., "The effect of monovalent cations and 7–deazaguanine on G–tetraplex structures and human telomerase," *Proc. Am. Assoc. Cancer Res.,* 38:512, Abstract #3438, (Mar. 1997).

Izbicka et al., "Evaluation of the cytotoxic effects of novel telomerase inhibitors in vitro," *Proc. Am. Assoc. Cancer Res.,* 38:637, Abstract #4277, (Mar. 1997).

Maine et al., "Interaction between telomeric oligonucleotide primers and CHO non–processive telomerase," *Proc. Am. Assoc. Cancer Res.,* 37:561, Abstract #3845, 1996 (Mar. 1997).

Parra et al., "AZT induces high frequency, rapid amplification of centromeric DNA," *Cytogenet. Cell Genet.,* 76:128–133, 1997.

Qiu and Windle, "Analysis of processive and non–processive telomerase activity using a sensitive and quantitative ligation and PCR–based assay," *Proc. Am. Assoc. Cancer Res.,* 37:561, Abstract #3846, (Mar. 1996).

Raymond et al., "Agents that target telomerase and telomeres," *Curr. Opin. Biotechnol.,* 7:583–591, 1996.

Schwarz et al., "Reversible oligonucleosome self–association: Dependence on divalent cations and core histone tail domains," *Biochem.,* 35:4009–4015, 1996 (Issue No. 13).

Sun et al., "Human telomerase inhibition by G–tetraplex interactive compounds," *Proc. Am. Assoc. Cancer Res.,* 38:637, Abstract #4278, (Marhc 1997).

Wajima et al., "Biological evaluation of a novel series of glycosylated camptothecin analogs," *Proc. Am. Assoc. Cancer Res.,* 37:434, Abstract #2963, (Mar. 1996).

Runge and Zakian, "Introduction of extra telomeric DNA sequences into *Saccharomyces cerevisiae* results in telomere elongation," *Mol. Cell. Biol.,* 9(4):1488–1497, (Apr. 1989).

Seela and Thomas, "8. Duplex stabilization of DNA: Oligonucleotides containing 7–substituted 7–deazaadenines," *Helv. Chim. Acta.* 78:94–108, 1995.

Shampay and Blackburn, "Generation of telomere–length heterogeneity in *Saccharomyces cerevisiae,*" *Proc. Natl. Acad. Sci. USA,* 85:534–538, (Jan. 1988).

Shay et al., "Analysis of telomerase and telomeres," *Methods in Molecular Genetics,* 5:263–280, 1994.

Shippen–Lentz and Blackburn, "Functional evidence for an RNA template in telomerase," *Science,* 247:546–552, 1990 (Feb. 2, 1990).

Shippen–Lentz and Blackburn, "Telomere terminal transferase activity from *Euplotes crassus* adds large numbers of TTTTGGGG repeats onto telomeric primers," *Mol. Cell. Biol.,* 9:2761–2764, (Jun. 1989).

Strahl and Blackburn, "The effects of nucleoside analogs on telomerase and telomeres in Tetrahymena," *Nucl. Acids Res.*, 22:893–900, 1994.

Strahl and Blackburn, "Effects of reverse transcriptase inhibitors on telomere length and telomerase activity in two immortalized human cell lines," *Mol. and Cell. Biol.*, 16:53–65, (Jan. 1996).

Sussel and Shore, "Separation of transcriptional activation and silencing functions of the RAP1–encoded repressor/activator protein 1: isolation of viable mutants affecting both silencing and telomere length," *Proc. Natl. Acad. Sci. USA*, 88:7749–7753, (Sep. 1991).

Tishkoff et al., "The sep1 mutant of *Saccharomyces cerevisiae* arrests in pachytene and is deficient in meiotic recombination," *Genetics*, 139:495–509, (Feb. 1995).

Wang and Zakian, "Telomere—telomere recombination provides an express pathway for telomere acquisition," *Nature*, 345:456–458, (May 31, 1990).

Yu and Blackburn, "Developmentally programmed healing of chromosomes by telomerase in tetrahymena," *Cell*, 67:823–832, (Nov. 15, 1991).

Yu et al., "In vivo alteration of telomere sequences and senescence caused by mutated tetrahymena telomerase RNAs," *Nature*, 344:126–132, (Mar. 8, 1990).

Lustig et al., "Involvement of the silencer and UAS binding protein RAP1 in regulation of telomere length," *Science*, 250:549–552, (Oct. 26, 1990).

Lyamichev et al., "An unusual DNA structure detected in a telomeric sequence under superhelical stress and at low pH," *Nature*, 339:634–637, (Jun. 22, 1989).

Matsumoto et al., "Identification of healed terminal DNA fragments in linear minichromosomes of *Schizosaccharomyces pombe*," *Mol. Cell. Biol.* 7(12):4424–4430, Dec. 1987.

McClintock, "The significance of responses of the genome to challenge," *Science*, 226:792–801, (Nov. 5, 1984).

Moyzis, "The human telomere," *Scientific American*, 48–55, (Aug. 1991).

Müller et al., "New telomere formation after developmentally regulated chromosomal breakage during the process of chromatin diminution in ascaris lumbricoides," *Cell*, 67:815–822, (Nov. 15, 1991).

Pluta and Zakian, "Recombination occurs during telomere formation in yeast," *Nature*, 337:429–433, 1989 (Feb. 2, 1989).

Pologe and Ravetch, "Large deletions result from breakage and healing of P. falciparum chromosomes," *Cell*, 55:869–874, 1988 (Dec. 2, 1985).

Prowse et al., "Identification of a nonprocessive telomerase activity from mouse cells," *Proc. Natl. Acad. Sci. USA*, 90:1493–1497, (Feb. 1993).

Ramasamy et al., "Synthesis and antitumor evaluation in mice of certain 7–deazapurine (pyrrolo[2,3,-d]pyrimidine) and 3–deazapurine (imidazo[4,5–c]pyridine) nucleosides structurally related to sulfenosine, sulfinosine, and sulfonosine," *J. Med. Chem.*, 33:1220–1225, 1990.

Rapaport "Anticancer Activities of Adenine Nucleotides in Tumor Bearing Hosts," *Chemical Abstracts*, 119(1):Abstract No. 123, 1993; *Drug Dev. Res.*, 28:428–431, 1993.

Robins, "The potential of nucleotide analogs as inhibitors of retroviruses and tumors," *Chemical Abstracts*, 100(23):Abstract No. 185159, 1984; *Pharm. Res.*, 1:11–18, 1984.

Romero and Blackburn, "A conserved secondary structure for telomerase RNA," *Cell*, 67:343–353, (Oct. 18, 1991).

Greider and Blackburn, "A telomeric sequence in the RNA of Tetrahymena telomerase required for telomere repeat synthesis," *Nature*, 337(6205):331–337, (Jan. 26, 1989).

Greider and Blackburn, "Identification of a specific telomere terminal transferase activity in tetrahymena extracts," *Cell*, 43:405–413, (Dec. 1985).

Greider and Blackburn, "The telomere terminal transferase of tetrahymena is a ribonucleoprotein enzyme with two kinds of primer specificity," *Cell*, 51:887–898, (Dec. 1987).

Greider, "Telomeres, Telomerase and Senescence," *BioEssays*, 12(8):363–369, (Aug. 1990).

Greider, "Chromosome first aid," *Cell*, 67:645–647, Nov. 5, 1991).

Gualberto et al., "Nucleic acid specificity of a vertebrate telomere–binding protein: evidence for G—G base pair recognition at the core–binding site," *Genes & Development*, 6:815–824, 1992.

Haber and Thorburn, "Healing of broken linear dicentric chromosomes in yeast," *Genetics*, 106:207–226, (Feb. 1984).

Haber et al., "Meiotic and mitotic behavior of dicentric chromosomes in *Saccharomyces cerevisiae*," *Genetics*, 106:185–205, (Feb. 1984).

Hardy et al., "A RAP1–interacting protein involved in transcriptional silencing and telomere length regulation," *Genes & Development*, 6:801–814, 1992.

Hardesty et al., "Disposition of the Antitumor Agent Sangivamycin," *Chemical Abstracts*, 81(9), Abstract No. 45178, 1974 and *Cancer Res.*, 34:1005–1009, 1974.

Harrington and Greider, "Telomerase primer specificity and chromosome healing," *Nature*, 353:451–454, (Oct. 3, 1991).

Herrick et al., "Mobile elements bounded by $C_4A_4$ telomeric repeats in oxytricha fallax," *Cell*, 43:759–768, (Dec. 1985).

Hunter et al., "Precise excision of telomere–bearing transposons during oxytricha fallax macronuclear development," *Genes & Development*, 3:2101–2112, 1989.

Jäger and Philipssen, "Stablization of dicentric chromosomes in *Saccharomyces cerevisiae* by telomere addition to broken ends or by centromere deletion," *The EMBO Journal*, 8(1):247–254, 1989.

Kang et al., "Crystal structure of four–stranded oxytricha telomeric DNA," *Nature*, 356:126–131, (Mar. 12, 1992).

Katinka and Bourgain, "Interstitial telomeres are hotspots for illegitimate recombination with DNA molecules injected into the macronucleus of *Paramecium primaurelia*," *The EMBO Journal*, 11(2):725–732, 1992.

Kim, et al., "Specific association of human telomerase activity with immortal cells and cancer," *Science*, 266:2011–2014, (Dec. 13, 1994).

King and Yao, "Tandemly repeated hexanucleotide at tetrahymena rDNA free end is generated from a single copy during development," *Cell*, 31:177–182, (Nov. 1982).

Kipling and Cooke, "Beginning or end! Telomere structure, genetics and biology," *Human Molecular Genetics*, 1(1):3–6, 1992.

Klingelhutz et al., "Restoration of telomeres in human papillomavirus–immortalized human anogenital epithelial cells," *Mol. Cell. Biol.*, 14:961–969, (Feb. 1994).

Lange, et al., "Structure and variability of human chromosome ends," *Mol. Cell. Biol.* 10(2):518–527, (Feb. 1990).

Larson et al., "Dynamics of telomere length variation in tetrahymena thermophila," *Cell*, 50:477–483, (Jul. 31, 1987).

Lee and Blackburn, "Sequence–specific DNA primer effects on telomerase polymerization activity," *Molecular and Cellular Biology,* 13(10):6586–6599, (Oct. 1993).

Liu and Gilbert, "The yeast KEM1 gene encodes a nuclease specific for G$ tetraplex DNA: Implication on in vivo functions for this novel DNA structure," *Cell,* 77:083–1092, (Jul. 1, 1994).

Liu and Gilbert, "Gene disruption of a G4–DNA–dependent nuclease in yeast leads to cellular senescence and telomere shortening," *Proc. Natl. Acad. Sci. USA,* 92:6002–6006, (Jun. 1995).

Lundblad and Szostak, "A mutant with a defect in telomere elongation leads to senescence in yeast," *Cell,* 57:633–643, 1989 (May 19, 1989).

METHODS FOR MODULATION AND INHIBITION OF TELOMERASE

This application is a continuation-in part of patent application Ser. No. 08/675,119 filed Jul. 3, 1996 which is a continuation-in-part patent application No. 60/000,927 filed Jul. 6, 1995, the entire contents of which are incorporated herein without prejudice and without disclaimer.

The government has certain rights in the invention pursuant to Grant CA67760 from the National Institutes of Health.

BACKGROUND OF THE INVENTION

A. Field of the Invention

The present invention relates generally to the field of molecular biology. More particularly, certain embodiments concern methods and compositions useful in modulating or inhibiting human telomerase activity. In certain embodiments, the invention concerns the use of these agents in treatment of proliferative cell disorders, particularly for cancers whose proliferation is determined by processive telomerase activity.

B. Description of Related Art

Telomeres play an important role in chromosome organization and stability. Human telomerase is a terminal transferase that adds TTAGGG units onto the telomere end. In general, telomerase activity is not detected in normal somatic cells leading to the implication of telomerase in cancer and the impetus to develop agents that selectively target telomerase activity.

1. Genomic Instability of Cancer Cells

One of the general characteristics of cancer cells is genomic instability. Though it is still unclear what causes this instability, a hypothesis gaining increasing attention is that free chromosome ends, either from chromosome breakage or from loss of the telomere sequences which cap the ends, are prone to illegitimate recombination events. Thus, telomeres provide stability to the chromosomes. However, there appears to be a gradual loss of telomere sequences with each cell division, perhaps because of the end-replication problem. Tumor cells have shortened telomeres, but they also possess greatly elevated levels of the enzyme telomerase to overcome the end-replication problem, while normal cells do not. Thus, telomerase is an attractive target for new anti-cancer agents because of the expected selectivity for neoplastic cells.

2. Telomeres

Telomeres consist of simple DNA repeats at the end of eukaryotic chromosomes and the proteins that bind specifically to those sequences in whole cells (Blackburn, 1991; Zakian, 1989). Telomeric DNA sequences and structures are conserved among widely divergent eukaryotes. The essential telomeric DNA consists of a stretch of a G rich tandemly repeated sequence. Human and other vertebrate telomeres are based on TTAGGG repeat units. The telomere provides a protective "cap" for the end of the chromosome. Broken chromosomes and free DNA ends are susceptible to end-to-end fusion leading to dicentric, ring or other unstable chromosome forms, and to exonucleolytic degradation (Haber, 1984; Mann, 1983; McClintock, 1941; McClintock, 1942; Roth, 1988). By protecting against these events, telomeres prevent loss of genetic information from subtelomeric regions of the chromosome.

Telomeres, the ends of eukaryotic chromosomes, are composed of tandemly repeated guanine-rich sequences which have an important role in chromosome organization and stability. However, due to the nature of DNA synthesis, the 5' ends of telomeres shorten with each round of replication leaving a 3' overhang that is subject to degradation. This has been described as the "end-replication" problem of linear chromosomes (Watson, 1972; Olovnikov, 1973). The end-replication problem can be overcome by addition of nucleotides to the 3' end of the telomere. A telomere terminal transferase (telomerase) activity was initially discovered in Tetrahymena (Greider & Backburn, 1985). Telomerase activity has since been found in other ciliates (Zahler & Prescott, 1988; Shippen-Lentz & Blackburn, 1989), Xenopus (Mantell & Greider, 1994), yeast (Cohn & Blackburn, 1995), mouse (Prowse et al., 1993), and human cells (Morin, 1989). Telomerase is a ribonucleoprotein in which the internal RNA component serves as a template for directing the appropriate telomeric sequences onto the 3' end of a telomeric primer. The cloning (Greider & Blackburn, 1989) and secondary structure determinations of the Tetrahymena telomerase RNA have determined the template portion of the RNA which has suggested a model for the mechanism of telomerase activity. Telomerase is thought to act by: 1) Telomerase binding to the 3' single-stranded overhang of the telomere (TTAGGG in humans) which base pairs with the complementary bases of the RNA component of telomerase, 2) Nucleotide addition onto the 3' end of the telomere by telomerase using its RNA component as a template, and 3) Dissociation of the newly synthesized telomeric DNA from the RNA template and repositioning to allow for the next round of polymerization. This last step is called the translocation step.

The variety of secondary structures formed by the guanine-rich telomeric sequences involving G-quartets or hairpins(Guschlbauer, 1990; Williamson, 1994) may have an affect on telomerase activity. For example, there is evidence that the G-tetraplex structures formed by telomeric sequences may hinder initial telomerase binding (Zahler et al., 1991). On the other hand, it has been proposed that G-tetraplex formation may actually facilitate the translocation step.

G-quartet structures may also have a role in telomere function. For example, it has been shown that a variety of proteins will preferentially bind to G-quartet structures (Williamson, 1994). Also, the interaction between guanine-rich DNA strands may be involved in the association of chromosomes seen in cells in the presence of varying concentrations of $Na^+$ (Diaz & Lewis, 1975). The function of chromosomal association is unknown but it has been proposed that it is important in such functions as homologous pairing involved in meiosis (Sen & Gilbert, 1988). Recently, a yeast nuclease (Kem1p) was found to specifically recognize and cut only G-quartet structures (Liu & Gilbert, 1994). Deletion of this enzyme was shown to cause telomere shortening, cellular senescence, and blockage in the pachytene stage of meiosis in yeast (Bahler et al., 1994; Tishkoff et al., 1995; Liu et al., 1995).

Another possible function of telomeres has sparked a great deal of interest in cancer research. It has been recently proposed that telomere length may serve as a "mitotic clock"(Harley, 1995; Shay, 1995). Normal cells in which telomeres shorten to a critical length become senescent (Allsopp et al., 1992; Harley, 1991). In contrast, immortal cancer cells have an unlimited replicative capacity. Due to the findings that telomerase activity is present in a variety of tumor cells, (Chadeneau et al., 1995; Counter et al., 1994; Counter et al., 1995; Kim et al., 1994) it appears that activation of telomerase is one link to cellular immortality.

This makes inhibition of telomerase an ideal strategy for anti-cancer therapy. A number of nucleoside reverse transcriptase inhibitors show anti-telomerase activity in human and Tetrahymena (Strahl & Blackburn, 1994; Strahl & Blackburn, 1996).

3. Chromosome End Replication Problem

Telomeres play a critical role in allowing the end of the linear chromosomal DNA to be replicated completely without the loss of terminal bases at the 5'-end of each strand. Watson (1972) and Olovnikov (1971, 1973) independently described the "end-replication" problem, i.e., the inability of DNA polymerase to replicate fully the ends of a linear DNA molecule. All known DNA polymerases require a primer to initiate polymerization that proceeds in 5'→3' direction. After degradation of the RNA primers, filling-in of internal gaps, and ligation events, the parental strand remains incompletely copied. Thus, in the absence of mechanisms to overcome the end-replication problem, the 5' end of the newly synthesized DNA in each duplex is shortened following every round of DNA replication. The 3' single stranded overhang, if not degraded, is converted to a double stranded deletion in the subsequent generation.

4. Telomerase

Immortal cells appear to overcome the end-replication problem by using telomerase to add telomeric DNA repeats to chromosomal ends. Because its mechanism of action involves the copying of an RNA template into DNA, telomerase can be classified as a reverse transcriptase. However, unlike typical reverse transcriptases from retroviruses or lower eukaryotes, it is a ribonucleoprotein that contains its own RNA template as an integral part of the enzyme (Blackburn, 1992). The RNA moiety of telomerase from various ciliates has been cloned and sequenced. For example, the Tetrahymena telomerase RNA moiety is a 159-nucleotide RNA in which a 3'-CAACCCCAA-5' (SEQ ID NO:1) sequence serves as the template for the synthesis of TTGGGG repeats (Greider, 1989). In Euplotes telomerase, a 15 nucleotide portion, 3'-CAAAACCCCAAAACC-5' (SEQ ID NO:2) of a 191 nucleotide RNA was found that could serve as a template for the synthesis of TTTTGGGG repeats (Shippen-Lentz, 1990). It is of interest to note that the Euplotes 191 nucleotide RNA and the Tetrahymena 159 nucleotide RNA share little overall primary sequence similarity. However, despite their divergent primary structures, the Euplotes 191-nucleotide RNA, the telomerase RNAs from *T. thermophila*, and these of other ciliates can all be folded into similar secondary structures with the putative telomeric template domains for each RNA lying in a corresponding position (Shippen-Lentz, 1989). Studies indicate that human telomerase also contains an endogenous RNA as template (Morin, 1989). The RNA component of human telomerase has been cloned (Feng, 1995).

Telomerase activity from human cells possesses a number of characteristics. First, in the presence of a G-rich human telomeric primer (TTAGGG)$_3$ (SEQ ID NO:3), TTP, dATP and [$\alpha$-$^{32}$P]dGTP, a ladder consisting of bands spaced six bases apart will form (Morin, 1989). Second, since telomerase contains an RNA component, telomerase activity can be obliterated in the presence of RNase A. It has been shown that the bands formed in the presence of excess cold nucleotides TTP and dATP and limiting amounts of [$\alpha$-$^{32}$P]dGTP (1.56 $\mu$M) are indicative of a pause site at the first guanine in the repeating unit of TTAGGG (Morin, 1989).

Evidence to date indicates telomerase is present in tumor cells but not in normal somatic cells. Thus, telomerase is an attractive novel drug target because there is a strong possibility for selectivity. Strahl and Blackburn (1994) has reported that several chain-terminating inhibitors (arabinofuranosyl-guanine triphosphate, Ara-GTP and 2', 3'-dideoxyribofuranosyl guanine triphosphate, ddGTP) efficiently inhibit Tetrahymena and human telomerase (Strahl and Blackburn, 1996).

5. Telomere/Telomerase in Cellular Senescence, Immortalization and Cancer

Early studies on human chromosome ends demonstrated that somatic (peripheral blood) telomeres appeared significantly shorter than germline (sperm) telomeres from the same individual (Cooke, 1986; Allshire, 1988; de Lange, 1990). It is now generally known that in most (if not all) somatic tissues, chromosomes gradually lose their terminal telomere sequence with each cell division (Harley, 1990; Hastie, 1990; Lindsey, 1991; Allsopp, 1992; Shay, 1993; Vaziri, 1993; Klingelhutz, 1994). In contrast, sperm telomeres increase in length with donor age, indicating that telomeres are actively maintained and even elongated in the germline (Allsopp, 1992). One explanation for this difference is that telomerase is active in germline cells but somehow is turned off in normal somatic tissues. This hypothesis has some support as no detectable telomerase activity has been found in extracts of embryonic kidney cells, or normal ovarian epithelium (Counter, 1992; Counter, 1994).

Whether telomere shortening has an impact on the proliferative activity of somatic cells remains unknown. The minimum telomere length required for maintaining full telomere function has not been fully established. Some evidence suggesting that telomere shortening could play a role in cellular aging comes from the analysis of primary human fibroblasts grown in culture (Harley, 1990; Allsopp, 1992). These cells lose approximately 50 bp per doubling and eventually stop dividing at a senescence stage call M1. Cells arrested at the M1 stage can be rescued by a variety of viral agents (Counter, 1992; Ide, 1984; Wright, 1989; Radna, 1989). The virally transformed cells continue to divide for as many as 50 cell divisions before they face another crisis, called M2, which is characterized by a balance of cell divisions and cell death (Counter, 1992). Cells that have bypassed the M1 arrest continue to lose their telomeric DNA, resulting in much shorter telomeres. An average telomere length of approximately 1.5 kbp or less as the cell approaches M2 may not contain sufficient telomere sequence to sustain normal telomere function.

Occasionally, virally transformed cultures yield immortal cells that have overcome the M2 crisis. Interestingly, unlike the senescent cells, the telomere of the immortal cell lines is stabilized by re-activation of the enzyme telomerase. Counter has postulated that telomerase activation is an obligatory step in the immortalization of human cells (Counter, 1992). In support of this hypothesis, telomerase activity was recently detected in metastatic human ovarian carcinoma cells but not in normal control cells, including healthy ovarian epithelium (Counter, 1994).

6 Telomerase Biochemistry

Alternatively, nucleotide analogs that are incorporated into telomeres by the action of telomerase may interfere with the function of the telomeres. For example, some nucleotide analogs so incorporated may block the ability of telomeres to form G-quarted or G-hairpin structures, thereby rendering the telomeres unable to be recognized by protein which specifically bind these structures. In the current model for the mechanism of telomeric DNA synthesis by telomerase (Blackburn, 1990), the 3' nucleotides of the overhang region of the chromosome terminus base-pair with a telomere-complementary sequence in the telomerase RNA. Next, the chromosomal end is extended using the RNA as a template, resulting in the addition of six telomeric nucleotides. Then, the extended DNA terminus unpairs from its RNA template and is repositioned on the 3' portion of the template, becoming available for another round of elongation by telomerase.

One of the most striking features of the telomerase reaction is that it involves not only copying of an internal template, but also an efficient translocation event which occurs after the last [5' most] residue of the template has been copied into DNA. The translocation step has been deduced from the processive nature of the telomerase reaction in a cell-free assay. Thus, telomerase initiates synthesis on a telomeric sequence DNA primer, and in the presence of an excess of the same primer or of a high concentration of a challenging primer, continues to elongate the first primer up to hundreds of nucleotides before dissociation (Blackburn, 1992).

Not all telomerase preparations are processive in the cell-free assay. Nonprocessive telomerase activity has been described in mouse FM3A cells (Prowse, 1993), Tetrahymena (Collins, 1993) and Xenopus (Mantell, 1994). Both processive and nonprocessive telomerases have been identified by the inventors from different cell lines. Intriguingly, the telomerase in S100 extracts of the human HeLa-S3 subline is nonprocessive, while the telomerase in the parental HeLa cells is processive. Whether these are two different enzymes or the same enzyme with different isoforms is currently being investigated. Whether processivity or non-processivity of the activity identified in the biochemical assay is relevant to telomerase function in whole cells remains to be elucidated. Evidence suggesting that telomerase functions nonprocessively in whole cells has been documented (Blackburn, 1992).

7. Deficiencies in the Prior Art

Strahl and Blackburn (1994) have tested AZT-TP, ara-GTP and ddGTP against a non-mammalian Tetrahymena telomerase and human telomerase (Strahl and Blackburn, 1996). Detailed methods and agents for inhibiting telomerase have not been described. In addition, there has been no distinction made between the telomerase produced in some normal cells and the telomerase produced by cancer cell. The identification of therapeutic compounds which have modulation or inhibitory activity against human telomerase is a desirable goal, particularly to identify compounds and develop methods of treatment of cancers in which processive telomerase contributes to the immortality and undesirable proliferation.

Toward this end and because of the important if not entirely understood role of telomerase in cell growth and senescence, there has been an effort to identify compounds that affect telomerase activity. Use of such compounds in controlling cell proliferation has obvious implications in treatment of malignant cancers. A goal of current medical investigation is to understand and treat cellular disorders, preferably to selectively target cancer cells either by altering the telomere, the telomerase, or the enzyme structure and/or by inhibiting telomerase.

SUMMARY OF THE INVENTION

The present invention overcomes one or more of these and other drawbacks inherent in the prior art by providing compositions and methods for their use in the inhibition and modulation of eukaryotic telomerase activity. More particularly, certain compositions have been shown to modify telomerase activity in cancer cells to more nearly approximate that found in normal or benign cells. Using a cell free biochemical assay, several classes of compounds, including nucleoside triphosphates and their derivatives have been identified as having an inhibitory effect on human telomerase. These compounds have a surprising effect on telomerase in apparently modulating processive telomerase to a non-processive activity. These results now offer new avenues of therapy for treatment of cancers characterized by cells with processive telomerase activity.

In the quest for finding nucleotide analogues that inhibit telomerase, 7-deaza-2'-deoxyguanosine triphosphate and 7-deaza-2'-deoxyadenosine triphosphate were found to be particularly potent inhibitors of telomerase activity. These compounds were originally investigated based on the rationale that the N-7 nitrogen of purine bases is required for Hoogsteen base-pairing involved in secondary structures formed by telomeric sequences. Unexpectedly, the 7-deaza nucleotides turned out to be poor substrates for human telomerase and were effective modulators of processive telomerase. The nucleotides thus not only present a novel mode of telomerase inhibition but also are useful for the study of the role of DNA secondary structure in telomerase mechanism.

The compounds of the present invention have the general structure (A), (B) or (C)

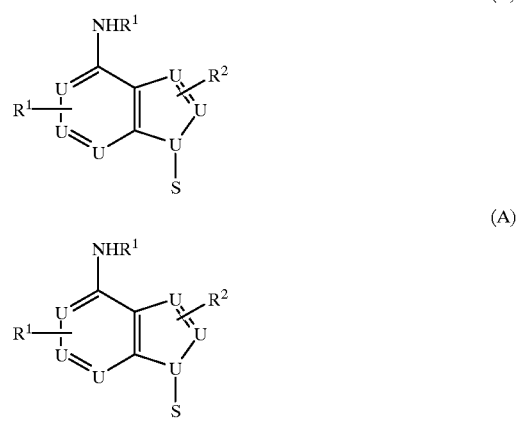

-continued

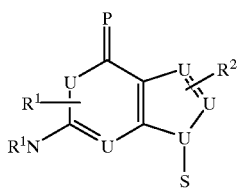
(B)

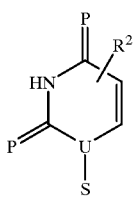
(C)

where U is independently carbon or nitrogen; $R^1$ is independently H, lower alkyl, or phenyl alkyl; $R^2$ is independently H, lower alkyl, $NH_2$, halogen, azido or alkene; P is independently oxygen or sulfur; and S is an acyclic or cyclic glycosyl group represented by the formulae:

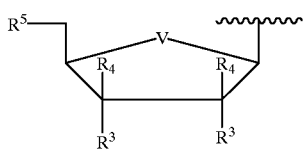

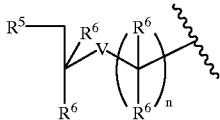

where $R^3$ is independently H, halogen, amino, azido, or hydroxyl; $R^4$ is independently H or OH; V is oxygen or methylene; and $R^5$ is OH, $(CH_2)_n$ $PO(OR^7)_2$, $OP(O)(OR^7)_2$; $R^6$ is H, lower alkyl, hydroxy-substituted lower alkyl, or haloalkyl; $R^7$ is H, lower alkyl, $CH_2OCO$(branched or straight chain alkyl (C1–C8) or aryl, and $R^8$ is H or CO(lower alkyl) and n is 1–2;

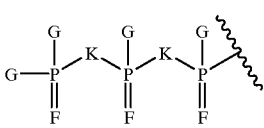

where K is oxygen or methylene; G is independently oxygen, sulfur or methyl; F is independently oxygen or sulfur; and the glycosyl bond between S and U is α or β.

The 7-deaza compositions of the present invention found to be useful telomerase inhibiting analogs may be modified in any of several ways. It is convenient to consider the design of analogs and derivatives in three general categories: (1) modifications of the heterobase of the nucleoside triphosphate. (2) modifications of the ribose sugar; and (3) modifications of the phosphate backbone The discovery that 7-deaza-2'-deoxynucleosides are effective in altering telomerase activity, has led to the conclusion that there are a wide range of modifications that can be made in this general class of deaza purines and pyrimidine nucleosides thus providing a plethora of compounds for selection by the practitioner in seeking to modulate telomerase activity.

Particular structures of the base portion of the nucleotide compounds contemplated by the inventors as useful for telomerase modulation or inhibition include the guanine analogs shown:

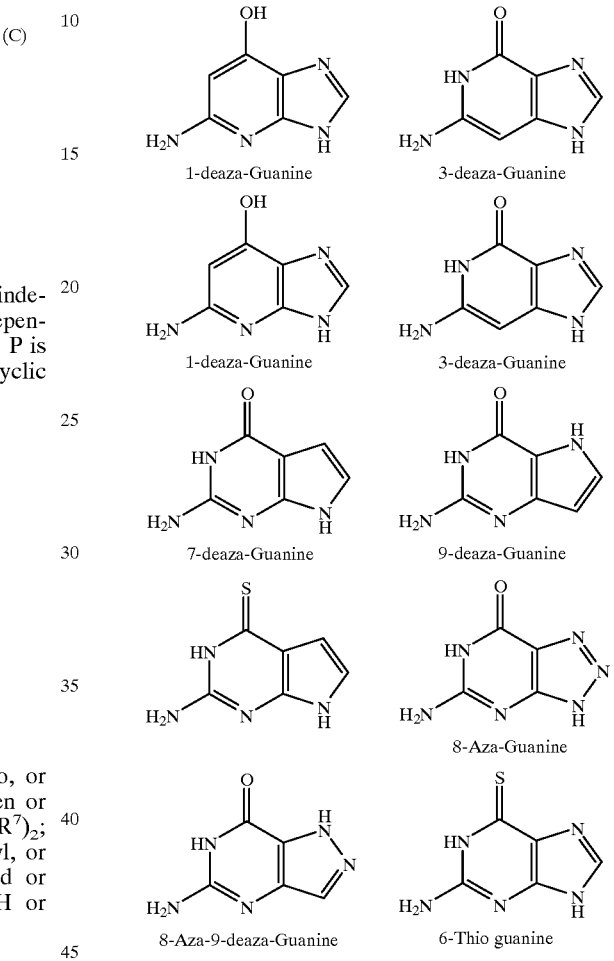

These compounds are summarized in the generalized formula below:

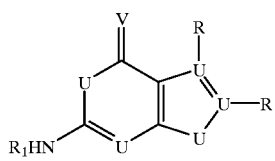

U=separately and independently C or N;
V=O or S;
R=H, Alkyl, Alkene, Alkyne, Amino, Halogen, Azido;
$R_1$=H, Alkyl, phenylaky The base components of dATP, dGTP, and dTTP are Adenine, Guanine, and Thymine, respectively. The structure of adenine, guanine, and thymine is shown below:

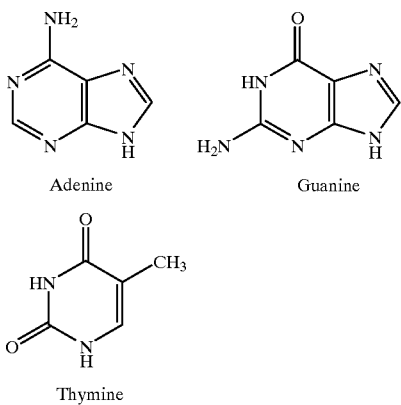

Adenine  Guanine

Thymine

Likewise, one may use adenines, such as deaza or azoadenines:

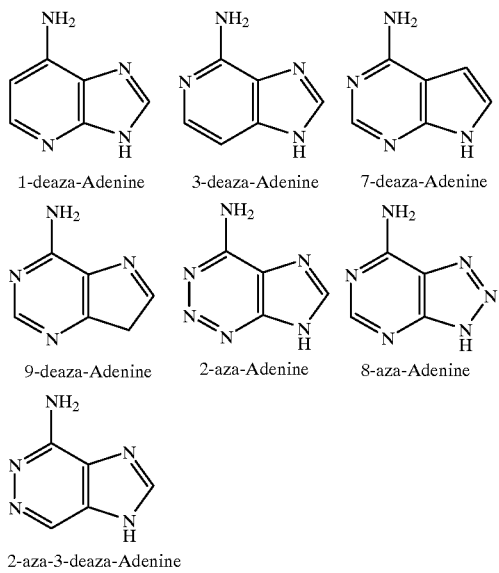

1-deaza-Adenine  3-deaza-Adenine  7-deaza-Adenine 9-deaza-Adenine  2-aza-Adenine  8-aza-Adenine 2-aza-3-deaza-Adenine In like manner modified thymine bases may be used, including:

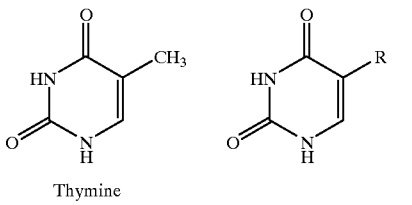

Thymine

R = $C_2H_5$, $C_3H_7$, F, Cl, Br, I

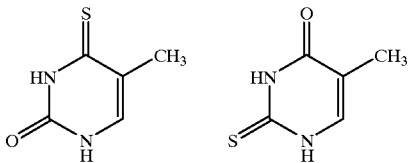

The following general formula summarizes these modifications on the thymine base.

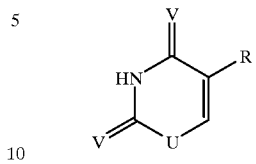

U=separately and independently C or N;

V=O or S;

R=H, Alkyl, Alkene, Alkyne, Amino, Halogen, Azido;

The bond between the base and the sugar moiety may be alpha or beta. The natural nucleoside is the β-D form. Nonnaturally occurring forms include β-L, α-D and α-L.

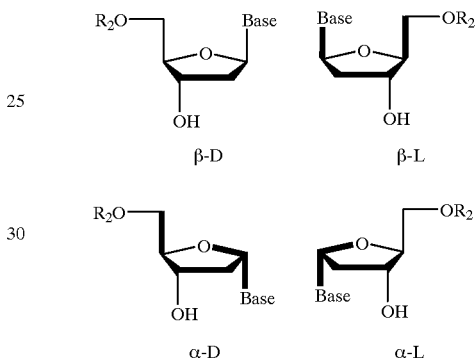

β-D  β-L

α-D  α-L

Further examples of nucleotide analogs with sugar modification include the 2'Deoxy-3'-deoxy-3'-substituted nucleosides (or nucleotides):

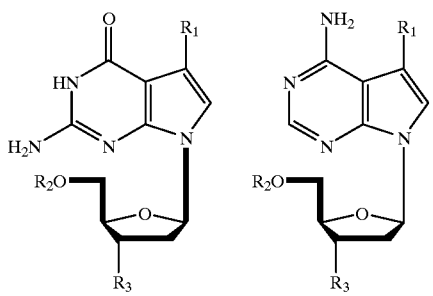

$R_1$=$CH_3$, $C_2H_5$, etc, and Halogen, F, Cl, Br, I etc $R_2$=H (nucleoside), or any of the modified nucleoside triphosphates $R_3$=H, F, Cl, $NH_2$, $N_3$ Of course the sugar moiety need not be limited to any particular sugar and several sugars are contemplated as suitable including in addition to 2'-deoxyribose, ribose, arabinose, xylose, and lyxose

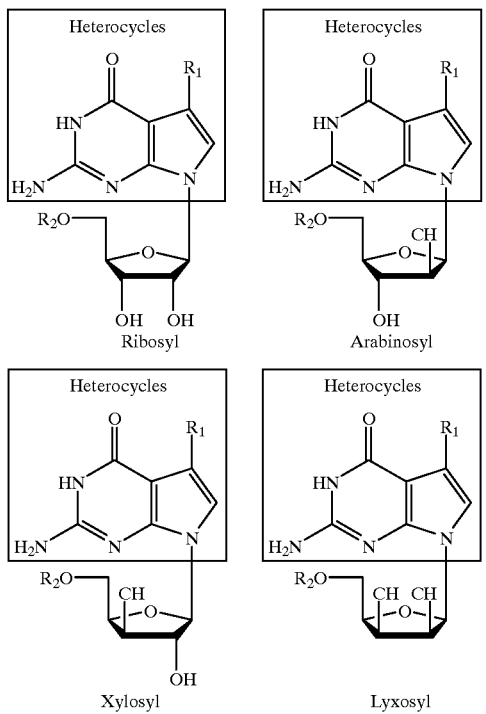

$R_1=CH_3$, $C_2H_5$, etc, and Halogen, F, Cl, Br, I etc
$R_2=H$ (nucleoside), or any of the modified nucleoside triphosphates
Carbocyclic compounds may be substituted for the natural sugars:

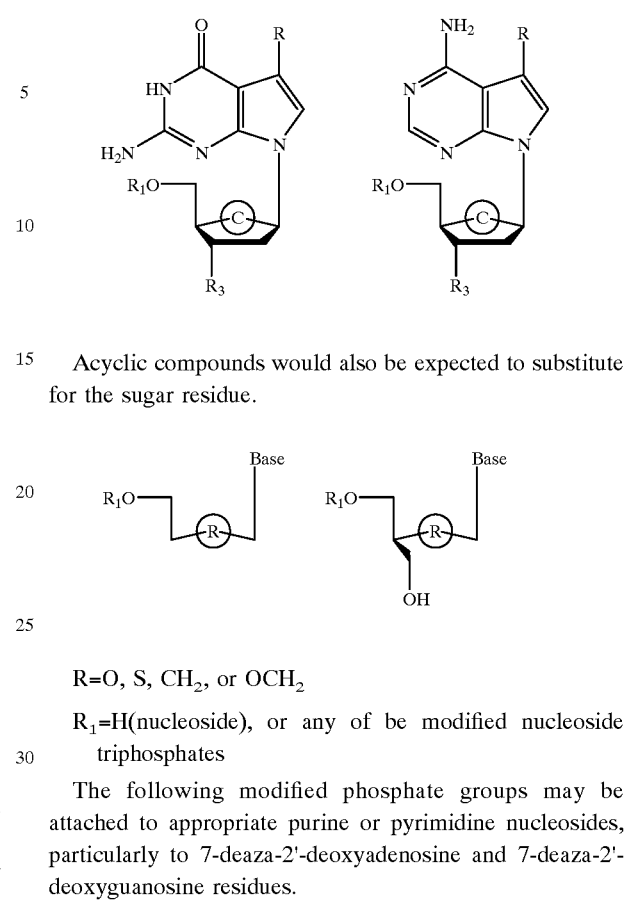

Acyclic compounds would also be expected to substitute for the sugar residue.

$R=O$, $S$, $CH_2$, or $OCH_2$ $R_1=H$(nucleoside), or any of be modified nucleoside triphosphates The following modified phosphate groups may be attached to appropriate purine or pyrimidine nucleosides, particularly to 7-deaza-2'-deoxyadenosine and 7-deaza-2'-deoxyguanosine residues.

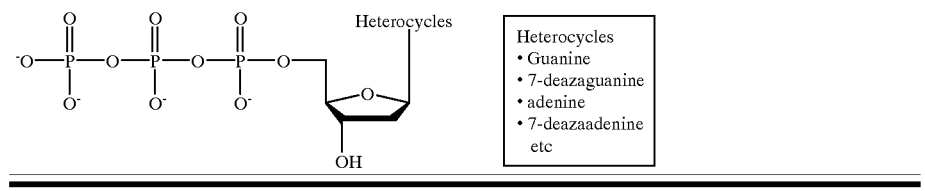

Possible Phosphate Modification:

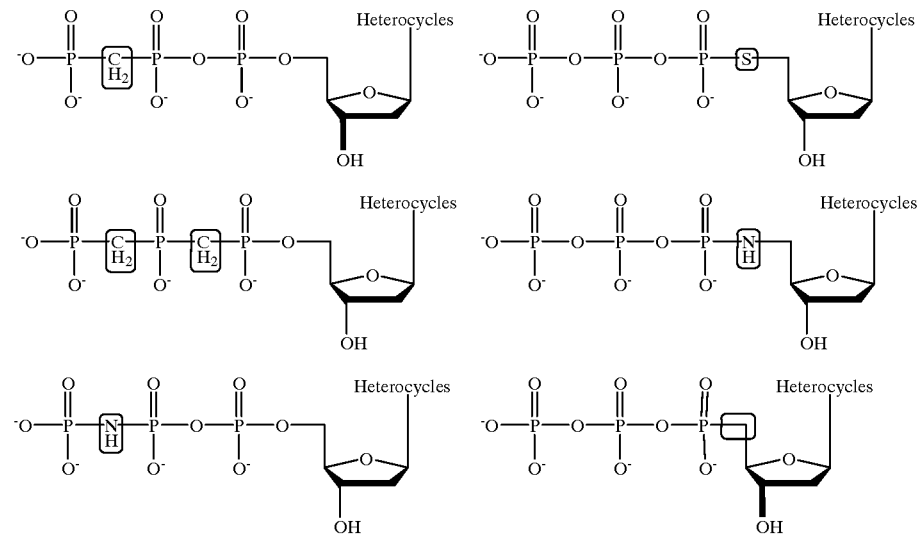

-continued

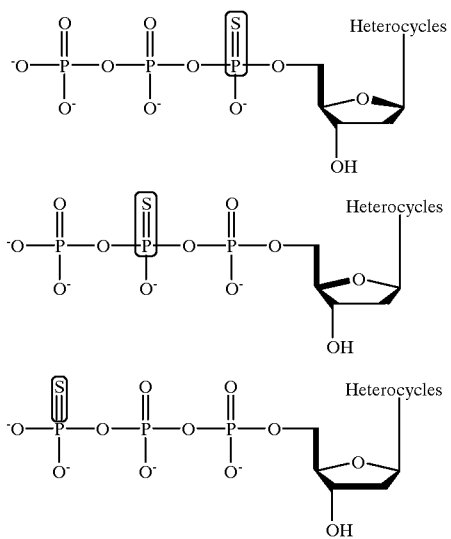

Particularly preferred 7-deaza compounds useful for the practice of the present on are 7-deaza-dGTP and 7-deaza-dATP, having the structures shown:

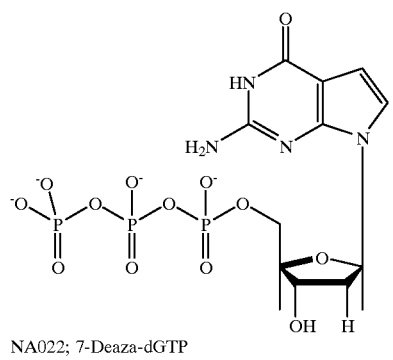

NA022; 7-Deaza-dGTP

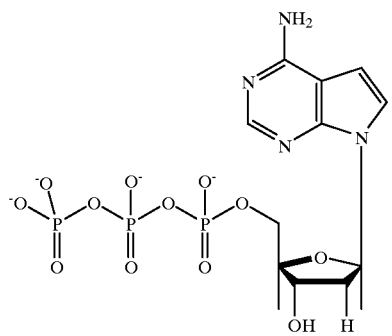

NA023; 7-Deaza-dATP

These analogs have been shown to affect telomerase activity as follows:(i) Both compounds inhibit telomerase in a dose-dependent manner; (ii) 7-deaza-dGTP and 7-deaza-dATP are incorporated into telomeric DNA by telomerase. 7-deaza-dATP can promote non-progressive activity by telomerase. However, incorporation of 7-deaza-dATP or 7-deaza-dGTP results in a telomeric ladder that is prematurely shortened; and (iii) Substrate inhibition (or allosteric inhibition) of 7-deaza-dGTP or 7-deaza-dATP is observed at a high concentration.

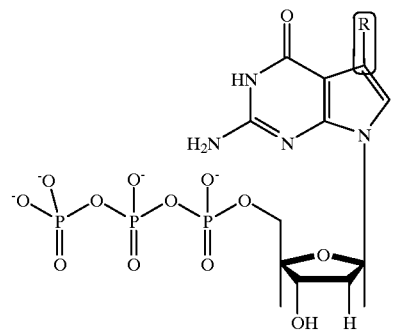

7-Substituted-7-Deaza-dGTP

R = CH₃, C₂H₅, etc or halogen, F, Cl, Br, I

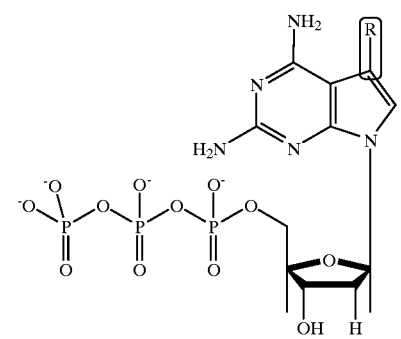

7-Substituted-7-Deaza-dATP

-continued

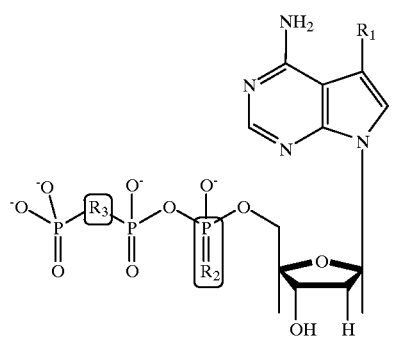

7-Substituted-7-Deaza-dATP

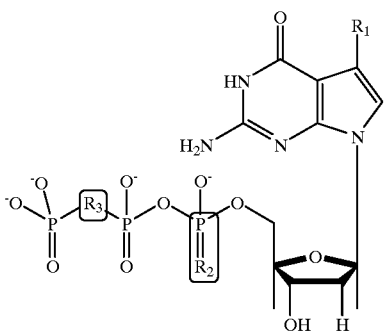

7-Substituted-7-Deaza-dGTP

R = CH₃, C₂H₅, etc or halogen, F, Cl, Br, I

| $R_2 = S, R_3 = O;$ |
| $R_2 = O, R_3 = \text{———CH}_2\text{———}$ or |
| $R_2 = S, R_3 = \text{———CH}_2\text{———}$ |

Synthetic procedures for the preparation of nucleotide analogs are available and some of these are preparable by analogy to procedures found in the literature (Scheit, 1980). A potential general synthetic pathway is outlined below for 7-substituted-7-deaza-dGTP α-phosphorothioates. Selected 7-substituted-7-deaza-dATP α-phosphorothioates could be prepared in a similar manner.

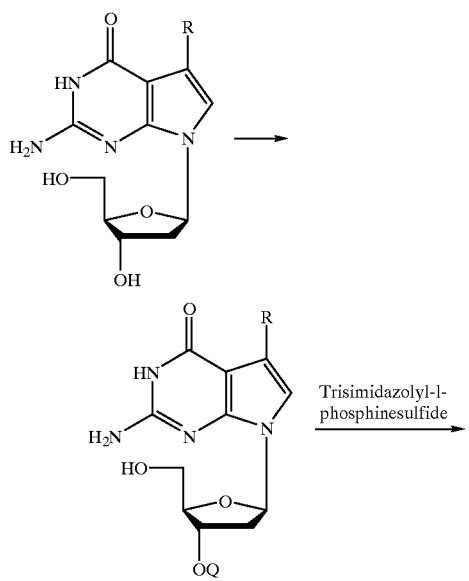

-continued

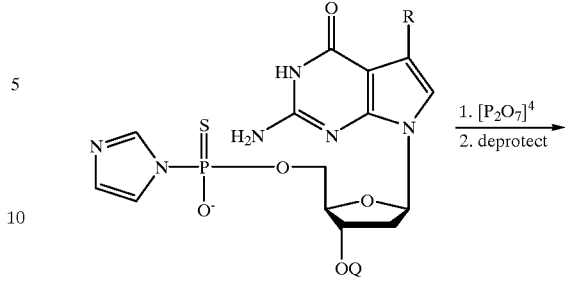

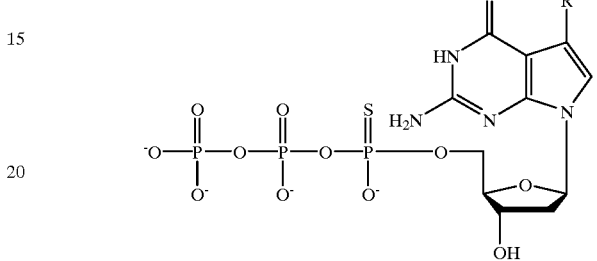

[R = H, CH₃, C₂H₅F, Cl, Br; I]

Where Q is a protecting group such as a silyl protecting group, e.g. tet-butyldimethyl silyl, tetrahydropyranyl, benzyl, etc.. In further aspects of the invention it has been found that human telomerase contains a 3'-5' exonuclease activity, analogous to Tetrahymena telomerase. Thus the synthesis of human telomeric DNA by telomerase is a balance of the 3'-5' exonuclease activity and the 5'-3' polymerase activity. In principle, synthesis of telomeric DNA can be reduced by blocking the polymerase or by stimulating the exonuclease, or both. One should be able to stimulate the exonuclease by drug interaction, thereby providing an effective method to shorten telomeres rapidly in cancer cells that produce high levels of telomerase, leading to a rapid cell death. Methods for stimulating the exonuclease include altering the interaction of dTTP and possibly other nucleotides with the telomerase. Compounds that block or limit dTTP are contemplated as useful with such a method.

Telomerase has a proof-reading-like exonuclease activity, so that incorporated modified nucleotides can be removed with no effect. The inventors contemplate that excision of the modified nucleotides can be achieved by blocking the telomerase exonuclease with an alpha-thionucleotide. Such incorporated nucleotides, cannot easily be removed by exonuclease activity because the thio-phosphate linkage is not cleaved by exonucleases. Suitable compounds include alpha, beta and gamma thio 7-deaza guanosine, adenosine and thymidine triphosphates such as for example alpha-thio-7-deaza-dGTP.

Some of these nucleotide analogs appear to also inhibit telomerase polymerization by a competition or allosteric mechanism mediated through telomerase inhibition.

The inventors believe that 7-deaza-2'-deoxynucleoside purines and pyrimidines herein described as telomerase modulators or inhibitors will be of particular use in the treatment of human cancers associated with high levels of processive telomerase. However, in order for these 2'-deoxynucleosides to exert their activity, they must be converted to triphosphates intracellularly, i.e., 7-deaza-2'-deoxyguanosine must be transported into the cells and be phosphorylated by a nucleoside kinase to 7-deaza-dGMP and, subsequently, further phosphorylated to 7-deaza-dGDP and 7-deaza-dGTP, respectively.

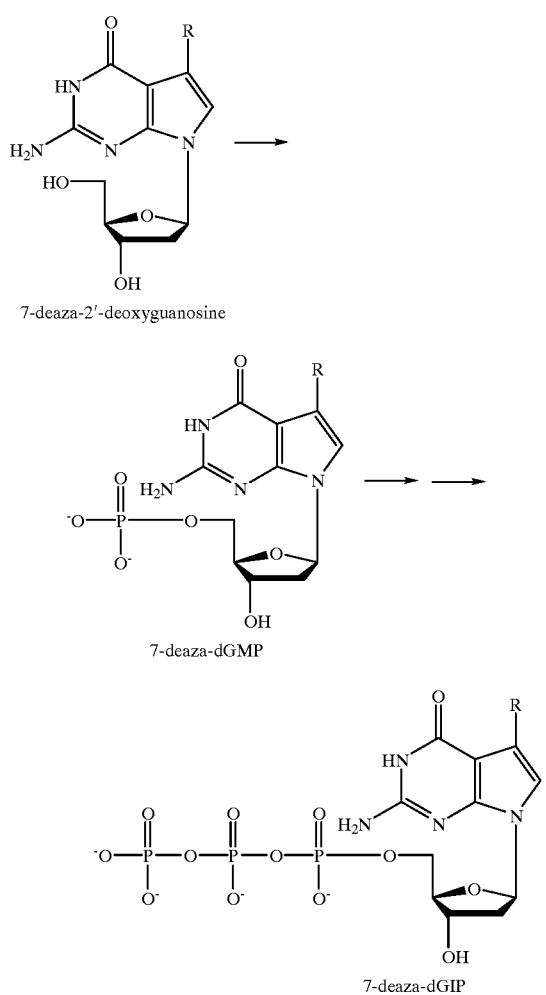

7-deaza-2'-deoxyguanosine 7-deaza-dGMP 7-deaza-dGIP

In general, phosphorylation of a nucleoside to its monophosphate is a rate-limiting step in whole cells. If the cells were unable to phosphorylate the nucleosides to monophosphates, no intracellular di- or triphosphates can be formed or identified. On the other hand, one also cannot simply incubate the cells with the phosphates (mono-, di-, or triphosphates) and expect them to transport into the cells and provide the cells with the triphosphates of nucleoside analogs. The phosphates are highly negatively charged, and therefore, will not transport into cells. Instead, the mono-, di-, or triphosphates will be dephosphorylated extracellularly by alkaline phosphorylase or 5'-nucleotidase back to the nucleoside.

In order to circumvent these problems, one can prepare prodrugs of monophosphates in which the negatively charged phosphate group is functionalized. The prodrug of monophosphates will then contain no charged groups and can be efficiently transported into cells. Once it has entered the cells, the protective group is hydrolyzed by esterase, and nucleoside monophosphate is released. Subsequently, phosphorylation of the liberated monophosphate will produce the desired nucleoside triphosphate. The general structure of the prodrugs is shown below:

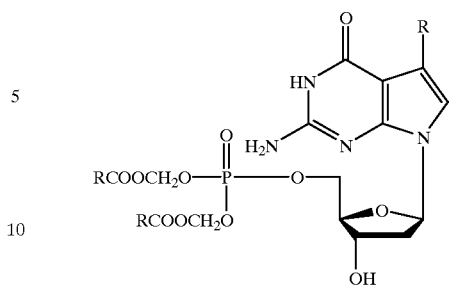

The use of this type of prodrug approach to deliver nucleotides to cells has been described (Farquhar et al., 1983; Sastry et al., 1992). Such compounds can enter cells and release the monophosphates which can be further phosphorylated to the corresponding triphosphates.

The present invention has identified one of the most potent telomerase inhibitors, 7-deaza-2'-deoxyguanosine-5'-triphosphate. The $IC_{50}$ value (6.8 $\mu$M) is at least 50-times more potent than AZT-TP. 7-deaza-2'-deoxyguanosine-5'-triphosphate lacks the 7-nitrogen atom which is essential for the formation of G-quartets or hairpins. If 7-deaza-2'-deoxyguanosine-5'-triphosphate is incorporated into telomeres, further telomere elongation may be prevented.

Several nucleoside triphosphate analogs with phosphate backbone modifications were demonstrated to be potent telomerase inhibitors. These phosphate backbone modifications include (1) thiophosphate, where the ($\alpha$) P=O bond is replaced with a P=S bond, e.g., NA013 ($IC_{50}$=81.5 $\mu$M) and (2) phosphonate, where the oxygen atom joining the $\beta$ and $\gamma$ phosphate (P) atom is replaced with a methylene (—$CH_2$—) group e. g. NA014 ($IC_{50}$=102 $\mu$M). (One of the most potent inhibitors identified was 7-deaza-2'deoxyguanosine-5'-triphosphate (NA022) with $IC_{50}$ value of 6.8 $\mu$M. 7-deaza-2'-deoxyadenosine-5'-triphosphate (NA023) also inhibits telomerase activity with an $IC_{50}$ value of 78.5 $\mu$M);

It is now possible to define the structure-activity relationship of nucleoside/nucleotide analogs as inhibitors and modulators of telomerase, thus allowing additional specific inhibitors and modulators of the enzyme to be identified. The design and synthesis of potent telomerase inhibitors based on these studies provide an array of telomerase modulating drugs to be used in the treatment of proliferative cell disorders, and particularly those involving cancers characterized by high levels of processive telomerase.

Useful telomerase-inhibitory compounds are not believed to be limited in any way to the specific compounds or nucleotide analogs and derivatives specifically disclosed herein. In fact, it may prove to be the case that the most useful pharmacological compounds designed and synthesized in light of this disclosure will be second generation derivatives or further-chemically-modified compositions.

Where telomerase-containing cells are located within an animal, a pharmaceutically acceptable composition of the telomerase inhibitor may be administered to the animal in an amount effective to modify the telomerase activity of the target cell. In terms of inhibiting telomerase activity in tumor cells, this is contemplated to be an effective mechanism by which to treat cancer that will have very limited side effects.

An embodiment in which the compositions of the present invention find particular utility is the treatment of cell proliferative disorders, and in particular human tumors characterized as having processive telomerase. The utilization of telomerase inhibitors (which either directly inhibit the telomerase activity or indirectly incorporate into telomere and thus prevent telomere further elongation) will lead to progressive telomere shortening in tumors where telomerase is active. Once the telomere length shortens to a critical length (ca 2 kb), the tumor will go into crisis and eventually die. These telomerase inhibitors will have little or no effect on the normal somatic cells because telomerase activity in normal cells is generally low or undetectable.

It is believed that the disclosed compounds will be useful for potentially treating a patient after surgical removal of a tumor. The patient would be treated with non-cytotoxic doses of nucleoside/nucleotide analogs for a prolonged period of time to prevent the recurrence of micro-metastasis. Alternatively, effective treatment of invading pathogens susceptible to telomerase inhibition are also contemplated, as are applications in treating age-related disorders such as atherosclerosis and osteoporosis.

There are several methods contemplated by the inventors for the delivery of such telomerase inhibitors into cells. In one embodiment, cells are provided with the corresponding nucleoside analogs, and subsequent cellular metabolism converts the nucleosides into nucleoside mono-, di- and tri-phosphates. In another embodiment, formulations of specific telomerase inhibitors are prepared in vehicles which protect the nucleotide from phosphatase degradation and facilitate the transport of nucleotides. In the case of the latter, a preferred method for delivery would be that of liposome-mediated delivery.

The therapeutic potential for liposome-mediated transfer of such telomerase inhibitors into human cells is well known to those of skill in the art. Based on existing evidence which shows that the systemic injection of cationic liposome complexes into animals is non-toxic (Stewart et al., 1992), the inventors contemplate the use of such liposome-mediated methods for introducing the compositions disclosed herein into animal subjects.

Liposomes have been used successfully with a number of cell types that are normally resistant to transfection by other procedures including T cell suspensions, primary hepatocyte cultures and PC 12 cells (Chang and Brenner, 1988; Muller et al., 1990). Liposomes have been used effectively to introduce drugs (Heath et al., 1986; Storm et al., 1988; Balazsovits et al., 1989), radiotherapeutic agents (Pikul et al., 1987), and enzymes (Imaizumi et al., 1990; Imaizumi et al., 1990) into a variety of cultured cell lines and animals. In addition, several successful clinical trails examining the effectiveness of liposome-mediated drug delivery have been completed (Lopez-Berestein et al., 1985; Coune, 1988). Furthermore, several studies suggest that the use of liposomes is not associated with autoimmune responses, toxicity or gonadal localization after systemic delivery Nabel et al., 1992; Mori and Fukatsu, 1992).

Introduction of the liposome-telomerase inhibitor complex may be by injection, either systemically into peripheral arteries or veins (including the carotid or jugular vessels), or directly into specific tissues to be targeted. Such liposome formulations are commercially available, e.g., 1:1 (w:w) mixture of the cationic lipid n-[1-(2,3-dioleyloxy)propyl]-N,N,N-trimethylammonium chloride (DOTMA) and dioleoyl phosphatidylethanolamine (DOPE) may readily be employed for such liposome formulations.

Based on the inventors' discovery of a method to modify or inhibit telomerase activity, it is contemplated that several classes of compounds will be useful. It will be desirable to determine which analogs and derivatives will be most suitable for particular treatments; for example, depending on the type of cancer cell present and particularly the amount and activity of telomerase present. A related aspect of the invention is the discovery that certain allosteric interactive agents will alter or inhibit telomerase activity. Nucleotides such as 7-deaza dGTP and 7-deaza dATP, are capable of allosterically inducing a reduction in telomerase polymerizing activity. The inventors have demonstrated that other nucleotides such as dGTP will not induce this effect, indicating the importance of the 7-deaza modification. This now provides a new method of modulating telomerase for the treatment of cancer by designing a series of 7-deaza compounds that will allosterically bind with telomerase with varying effects on modulating telomerase activity. Highly processive telomerase for example may require stronger inhibitors or modifications to the nucleotide analog that change allosteric interactions or are less efficiently incorporated into the telomere.

BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 5A shows the progressive telomerase activity of cancer cells.

DETAILED DESCRIPTION OF THE PREFERRED EMBODIMENTS

Figure 1:
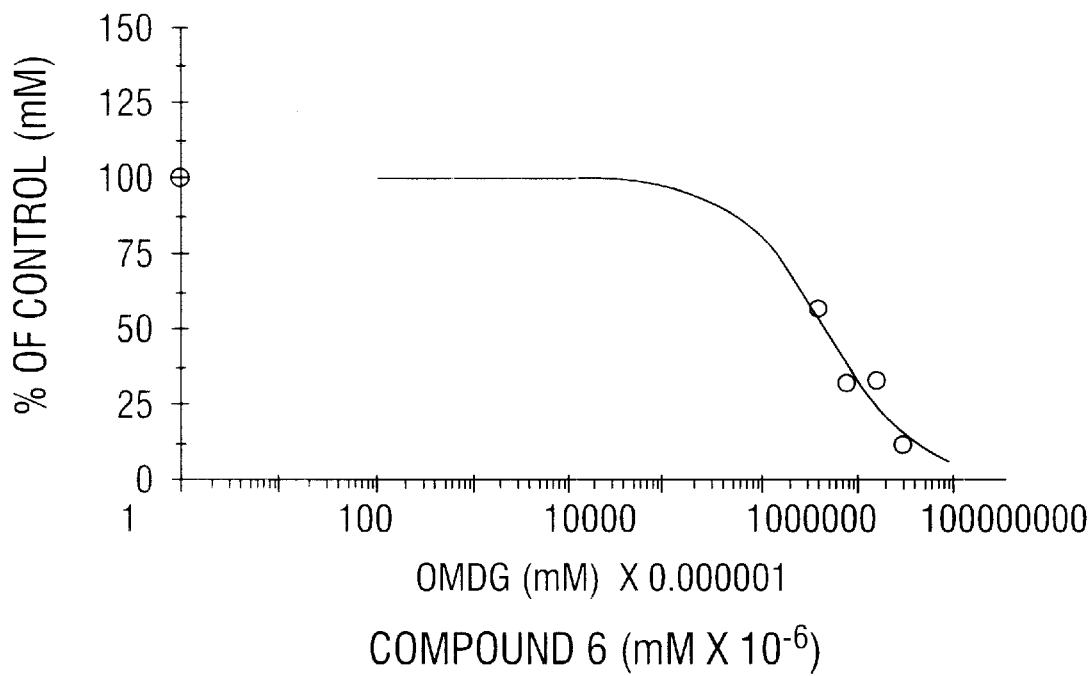
FIG. 1. shows the inhibition of human cancer HeLa cell telomerase activity by 6-methoxy-7-deaza-2'-deoxyguanosine. The inhibition is concentration dependent with an $IC_{50}$ of 4.9 $\mu$M.

The present invention provides several nucleoside triphosphates which are capable of inhibiting mammalian telomerase activity. The compounds show differential inhibition against telomerase in S100 extracts of transformed human fetal kidney tumor 293 cells (a processive telomerase) versus that of hamster UA21 cells (non-processive telomerase). This observation has prompted the investigation of nucleoside/nucleotide analogs which are useful in affecting telomere/telomerase function in cells.

A. Telomeric DNA as a Target

While inhibition of telomerase represents one way of interfering with the function of cellular telomeres, providing DNA reactive drugs which damage telomeric DNA itself is a possible complementary approach.

Damage to telomeres is more detrimental to rapidly growing (i.e. tumor) cells than to normal cells. Given the significance of telomeres, compromised telomere integrity results in incomplete replication of telomeric DNA, disturbed chromatin structure and, eventually, cell death. An attempt to replicate telomeres with unrepaired lesions may further amplify the initial damage. Thus, tumor cells that have very short telomeres would be the most susceptible to incomplete telomere replication. Moreover, lesions in telomeric DNA may be more lethal in those tumor cells that require telomerase to actively maintain their already shortened telomeres.

Because of the presence of highly repetitive sequences $(TTAGGG)_n$, it is possible that DNA-reactive agents with a preference for A/T or G/C may damage telomeric DNA to a different extent than other regions of the chromosome. Also, the repair of damage in telomeres is likely to be slower than repair in the rest of the genome (Kruk and Bohr, 1993).

Conventional DNA-reactive antitumor drugs may affect telomeres in addition to inducing damage to other regions of the genome. Lesions in telomeres may disturb telomerase action. For example, bifunctional alkylating agents may form crosslinks between telomeric DNA and telomerase protein and/or RNA components. Such adducts will probably abrogate enzyme activity. Conversely, inhibition of telomerase may enhance lethality of drug-induced DNA lesions in other regions. By examining the effects of DNA damaging drugs on telomeres one may determine which lesions in telomeres can be tolerated by cells and at what maximal levels, how lesions repaired in telomeres compare to other regions of DNA, and which drugs have potential for preferential targeting of telomeres.

B. Non-Processive/Processive Telomerase Activity

The non-processive telomerase activity produced by normal cells is distinctly different from the processive telomerase activity produced by cancer cells. Processive telomerase aggressively synthesizes telomeric repeats. This type of activity is necessary for maintaining or growing telomeres in cancer cells. Telomere maintenance allows cancer cells to be immortal without the danger of chromosome instability. While normal cells do not maintain or grow their telomeres nor cell do produce a regulated and non-aggressive form of telomerase characterized by its non-processive activity. This activity appears to be necessary for certain functions in normal cells other than maintaining or growing telomeres. Unlike cancer cells, normal cells are not immortal, ostensibly due to lack of or very low levels of processive telomerase. This information indicates that a method for converting processive telomerase to non-processive telomerase in a way that would not harm normal cells but would selectively affect cancer cells.

The present invention demonstrates a method of altering processive telomerase so that it acts non-processively. This modulation causes cancer cell telomerase to more closely mimic normal cell non-processive telomerase. In general, changes to convert processive telomerase to non-processive telomerase may involve either direct changes to the telomerase complex itself or indirect methods that ultimately affect telomerase activity. Direct methods for example may involve cleaving the RNA component into partial fragments, such that only processive activity is affected. Processive telomerase activity may be modulated to non-processive activity by a partial digest treatment with RNase A or with other RNA cleaving agents, such as ribozymes. Similar results may be obtained by chemical modification of the RNA, or binding of agents, such as oligonucleotides.

The present invention illustrates an indirect method for converting processive telomerase to nonprocessive telomerase by allowing telomerase to incorporate 7-deaza-dGTP or related analogs into telomeric DNA. 7-deaza-dGTP and its analogs, once incorporated into the telomere, alter the telomeric secondary structure so that telomerase can no longer recognize it properly for processive telomere synthesis. Other nucleotides that can be used as substrates by telomerase, and which are incorporated into the telomere will also mediate telomere dysfunction, include alpha-thionucleotides. These nucleotide analogs can be incorporated in the telomere by any polymerase capable of replicating the telomere. Once in place, only the telomeric sequence is affected since the unique G-rich repeat structure of telomeric DNA is found only in the telomere.

The inventors' strategy is to provide selected nucleoside analogs that act in two ways; both to alter processive telomerase to act non-processively and to affect telomere structure so that telomere-binding proteins will no longer recognize the telomere. The telomere is thus left unprotected, resulting in chromosome instability and cell death. Cancer cells will be selectively targeted because these cells depend on processive telomerase to incorporate the nucleotide analog. The more telomerase that a cell produces, the more effective the strategy. The method also has advantages over merely inhibiting telomerase, because the telomere is immediately affected and it is not necessary to wait for the telomere to shorten and become dysfunctional.

The disclosed method of using selected nucleoside analogs to alter telomerase activity does not inhibit telomerase but merely converts one form of telomerase to another form of telomerase.

C. Telomerase Activity in Human Tumor Cells

Using a telomerase assay, the inventors have successfully identified the telomerase activity in the following cell lines: 293 (a transformed human embryonic kidney cell line), HeLa and HeLa-S3 (a human cervical tumor cell line), CEM (a human leukemia cell line) and UA-21 (a subline of Chinese hamster cell CHO line). Interestingly, processive telomerase activity has been identified in the S100 extracts of 293, CEM, HeLa cell lines, and non-processive telomerase activity in the S100 extracts of HeLa-S3, UA-21 and W138 cell lines. Rnase prevents telomerase activity.

DNA ladders separated by 6 base-pairs are seen in S100 extracts of HeLa—human cervical tumor cells—indicative of a processive enzyme; whereas only one a band is detected in S100 extracts of UA-21—a subline of Chinese hamster cells indicative of a non-processive enzyme. Both the processive and non-processive enzyme activities are sensitive to RNase treatment. These results indicate that the formation of the processive or non-processive DNA band(s) is RNA-dependent. The effect of RNase on telomerase activity can be prevented if RNase Guard (Pharmacia) is added to inhibit the RNase activity.

D. Inhibition of Telomerase Activity by Selected Nucleoside Triphosphates

Selected nucleoside triphosphates were tested in one or both of the "conventional" or "modified" telomerase assays described in Methods using the human processive and the CHO non-processive telomerases. Initially, three chain-terminators were selected: 2', 3'-dideoxythymidine triphosphate (ddTTP), 3'-fluoro-2', 3'-dideoxythymidine triphosphate (F-ddTTP), and 3'-azido-2-', 3'-dideoxythymidine triphosphate (AZ-ddTTP) as prototype agents to investigate whether they could inhibit telomerase activity. The three compounds are dTTP analogs without a 3'-OH group for subsequent chain elongation. They may either incorporate into the telomere sequence and terminate further chain elongation or compete directly with dTTP for the substrate binding site in the telomerase reaction. In either case, telomerase activity is inhibited.

Results showed that AZ-ddTTP inhibits both the human processive and the CHO non-processive telomerase in a dose-dependent manner. The DNA ladder bands were quantitated using a Molecular Dynamic Personal Densitometer. The concentration of AZ-ddTTP required to inhibit the telomerase activity by 50% of the control is estimated to be 500 and 750 µM against the 293 and UA-21 telomerase, respectively. In contrast, the nucleoside AZT (3'-azidothymidine), at 2 mM, has a small effect on the telomerase activity.

The results suggested that only the nucleoside triphosphate, but not nucleoside, is an inhibitor of telomerase. Inhibition studies are typically performed at concentrations of dTTP and dATP (2 mM) which could be much higher than the $K_m$ of dTTP and dATP for telomerase. The inventors tried lower concentrations of dTTP and dATP (near the $K_m$; in the µM ranges) and showed that AZ-ddTTP is actually a more potent inhibitor of telomerase than previously estimated. It was found that ladder patterns were detectable even at dTTP and dATP concentrations as low as~200 µM. Even lower concentrations of dTTP and dATP are likely be effective with more highly purified enzyme concentrations.

It has been shown that FddTTP, with a 3'-fluoro substituent, inhibits the nonprocessive CHO telomerase completely but has little effect against the processive human telomerase. The change at the 3'- position causing a distinctly different inhibitory effect on two telomerase enzymes was both surprising and quite unexpected.

Additional dTTP analogs were studied. A compound with a 3'-amino substitution had only a marginal effect on the human telomerase activity. However, another compound, 4-thiothymidine triphosphate, with a 4-thio group rather than a 4-keto group on dTTP, inhibited the human processive enzyme completely at 1 mM. 4-thiothymidine triphosphate has a 3'-OH group and, therefore, appears not to chain-terminate the telomerase reaction when incorporated into the nascent DNA strand. This is the first observation that a dNTP analog with a heterocyclic ring modification has an effect on telomerase activity.

Selected dATP and dGTP analogs were also evaluated as potential telomerase inhibitors. 2'3'-dideoxyadenosine triphosphate (ddATP) inhibited human telomerase activity at 1 mM. This was similar to results obtained with 2'3'-dideoxythymidine triphosphate (ddTTP). Two deoxyguanosine triphosphate analogs with modifications on the phosphate group were found to inhibit human telomerase activity. In one modification, the (α) P=O bond was replaced with a P=S bond to form a thiophosphate. In a second modification, the oxygen atom joining the β and γ phosphate (P) atom was replaced with a methylene (—CH$_2$—) group to form a phosphonate. The new analogs have the following structure.

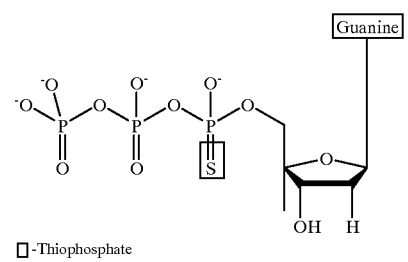

□-Thiophosphate

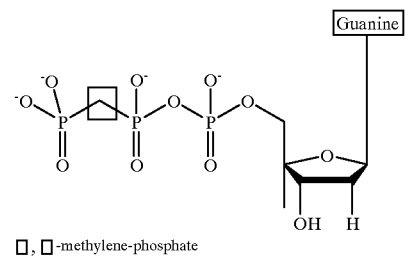

□, □-methylene-phosphate

It is expected that modifications at the sites indicated will provide additional nucleoside triphosphate telomerase inhibitors.

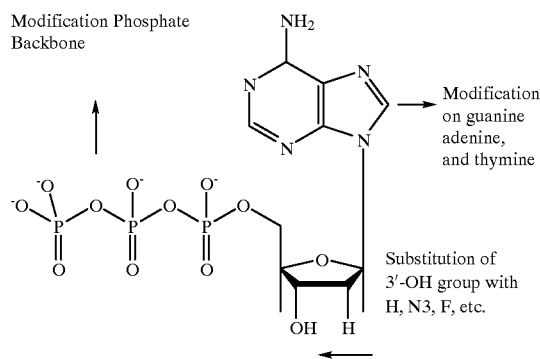

E. Effect of AZT (3'-Azidothymidine) on Telomere Length and Formation of Dicentric Chromosomes AZ-ddTTP is a negatively charged molecule and cannot be transported into cells. In order to study the effects of AZ-ddTTP on telomerase activity in a whole cell system, CHO cells were incubated with 800 $\mu$M (non-cytotoxic concentration) of 3'-azidothymidine (AZT nucleoside) for several generations. The effect of AZT on the telomere length and on the formation of unstable dicentric chromosomes was determined as an indirect measurement of the effect of AZ-ddTTP on intracellular telomerase activity. An initial, gradual shortening of the telomere length was found with a concurrent increase in the number of dicentric chromosomes in the AZT-treated CHO cells. This effect was only transient; after 20 generations, the fraction of cells with dicentric chromosome decreased.

AZ-ddTTP inhibits both the 293 and UA-21 enzymes. Studies have shown that the telomere length in cultured human cells passaged in non-cytotoxic concentrations of AZT (azidothymidine, nucleoside) is progressively shortened. In addition, the frequency of dicentric chromosomes (measured by fluorescence in-situ hybridization) increased in the presence of AZT. Eventually, the cells stopped growing and apparently died.

F. Intracellular Accumulation of AZT Mono-, Di-, and Tri-Phosphate Levels

Since only AZ-ddTTP (AZT triphosphate), and not AZT, inhibits telomerase activity, studies were initiated to determine intracellular AZT triphosphate concentrations. The metabolism of AZT is species-and cell type-specific (Bazarini, 1988; Balzarini 1989). In CHO cells, using $^3$H-labeled AZT, it was found that the uptake (transport and subsequent metabolism to its phosphate metabolites) of AZT was concentration- and time-dependent. AZT accumulates intracellularly at concentrations 2–3 times higher than the extracellular concentrations (0.25–750 $\mu$M) tested. Total AZT uptake reached a plateau in approximately 30 minutes. Subsequent HPLC analysis using a strong anion exchange column showed that the intracellular AZT, AZ-ddTMP, AZ-ddTDP, and AZ-ddTTP ratios are approximately 50–60:20:15:10 following a 90 minute incubation with 5–25 $\mu$M of AZT. It is estimated that about 200 $\mu$M of AZ-ddTTP could be formed intracellularly when cells are incubated with 750 $\mu$M of AZT. This intracellular concentration is lower than the $IC_{50}$ value obtained in the cell-free assay for the inhibition of the telomerase activity.

G. Inhibition of Telomerase by 7-deaza-dGTP and 7-deaza-dATP in the presence of limiting amounts of dGTP and dATP.

Figure 3:
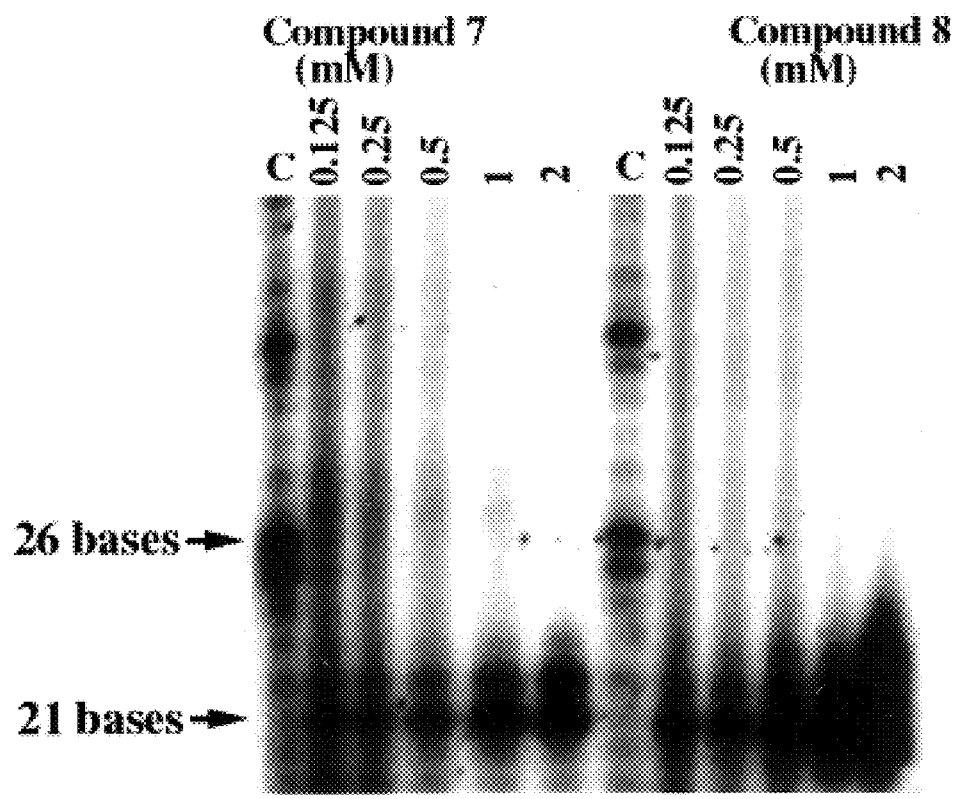
FIG. 3. shows incorporation of 6-methoxy-7-deaza-2'-deoxyguanosine-triphosphate (7) and 6-thio-7-deaza-2'-deoxyguanosine-5'-triphosphate (8) by human cancer telomerase.

FIGS. 3A and 3C illustrate the effect of 7-deaza-dGTP and 7-deaza-dATP on the level of telomerase activity. Inhibition of telomerase activity was indicated by a reduction in the intensity of the bands with increasing concentrations of inhibitor. The degree of inhibition was determined by measuring the intensity of the bands in the telomerase ladder with densitometry. The intensities in each lane were normalized to an internal standard, $^{32}$P 5' end-labeled (TTAGGG)$_3$, to compensate for differences in processing of the products and gel loading. Intensities in all lanes were expressed as a percent of the control to eliminate variability due to differences in film exposure and enzyme preparations. The concentration of inhibitor that results in a 50% reduction in telomerase activity ($IC_{50}$) was determined according to the method outlined in Materials and Methods ($IC_{50}$ values are in Table 1). The similarity of their $IC_{50}$ values reveals that 7-deaza-dGTP is just as efficient as cold dGTP in inhibiting the formation of [$\alpha$-$^{32}$P]dGTP labeled telomerase ladders. Both 7-deaza-dATP and cold dATP have a similar capacity to inhibit the formation of [$\alpha$-$^{32}$P]dATP labeled products.

TABLE 1

Inhibition of radiolabeled human telomerase ladder by 7-deaza-dGTP, 7-deaza-dATP, dGTP, and dATP

| Inhibitor | [$\alpha$-$^{32}$P]dNTP ($\mu$M) | Non-radioactive Nucleotides (mM) | $IC_{50}$ ($\mu$M) |
| --- | --- | --- | --- |
| 7-deaza-dGTP | dGTP* (1.56 $\mu$M) | TTP and dATP (1 mM) | 11 |
| dGTP | dGTP* (1.56 $\mu$M) | TTP and dATP (1 mM) | 5 |
| 7-deaza-dATP | dATP* (3.12 $\mu$M) | TTP and dGTP (1 mM) | 8 |
| dATP | dATP* (3.12 $\mu$M) | TTP and dGTP (1 mM) | 10 |
| 7-deaza-dGTP | dATP* (3.12 $\mu$M) | TTP and dGTP (1 mM) | 56 |
| 7-deaza-dATP | dGTP* (1.56 $\mu$M) | TTP and dATP (1 mM) | 59 |

$IC_{50}$ values were obtained according to Materials and Methods.

H. Inhibition of telomerase activity by 7-deaza-dGTP and 7-deaza-dATP in the presence of excess amounts of dGTP and dATP 7-Deaza-dGTP and 7-deaza-dATP can also inhibit telomerase activity even in excess (1 mM) dGTP or dATP respectively. The $IC_{50}$ value of 7-deaza-dGTP as a telomerse inhibitor in the presence of 1 mM dGTP, dTTP and 3.12 $\mu$M [$\alpha$-$^{32}$P]dATP was 56 $\mu$M. The $IC_{50}$ of 7-deaza-dATP was 59 $\mu$M when in the presence of 1 mM dATP, TTP and 1.56 $\mu$M [$\alpha$-$^{32}$P]dGTP.

I. 7-Deaza-dGTP and 7-deaza-dATP are telomerase substrates

Replacing dGTP with 7-deaza-dGTP in a reaction containing 1 mM dTTP and 3.12 $\mu$M [$\alpha$-$^{32}$P]dATP resulted information of radiolabeled products that are sensitive to RNase A. There are important characteristics of this reaction which distinguish it from a reaction with the native dGTP. First, the total amount of products produced by 7-deaza-dGTP was much less than that produced with dGTP. Second, telomerase appears to be less processive with 7-deaza-dGTP. As the concentration of 7-deaza-dGTP increased, the products became increasingly shorter and the total amount of products decreased until there was no activity at>1.5 mM 7-deaza-dGTP. There is no significant change in activity when dGTP is used as a substrate in the reaction with concentrations varying from 0.25 mM–2.0 mM.

Telomerase paused at significantly more sites in the presence of 7-deaza-dGTP. At a concentration of 0.5 mM 7-deaza-dGTP, there was such a large number of bands pertaining to various pause sites that a predominant pause site could not be determined. When the 7-deaza-dGTP concentration is 0.75–1 mM, a repeating triplet of pause sites was distinguishable. These bands appeared to be two, three, and four bases smaller than that with dGTP corresponding to the guanines in the TTAGGG repeat.

Similar results were observed when dATP was replaced by 7-deaza-dATP with 1 mM TTP and 1.56 $\mu$M [$\alpha$-$^{32}$P] dGTP. The products were sensitive to RNase A and processivity decreased with increasing 7-deaza-dATP concentrations. No telomerase activity was detected at >1.5 mM 7-deaza-dATP. However, the level of telomerase activity remained unchanged with 0.25–2.0 mM dATP as a substrate. Unlike what is observed with 7-deaza-dGTP, the presence of 7-deaza-dATP does not result in a change in pause sites compared to the reactions in the presence of dATP.

The present work shows that a pause site can shift to bands two bases smaller in the presence of excess TTP and dGTP and limiting concentrations of [α-$^{32}$P]dATP which would be the second thymine. The telomerase ladder was difficult to obtain with concentrations less than 3.12 μM of [α-$^{32}$P]dATP. In addition, a telomerase ladder was not generated in the presence of limiting radioactive dTTP. The dependence of the location of the pause sites on the concentration of nucleotides has also been demonstrated in Tetrahymena (Greider & Blackburn, 1987).

J. Inhibitory and Modulating Effect of 7-Deaza Nucleotides

The compounds 7-deaza-dGTP and 7-deaza-dATP have been found to be potent inhibitors and modulators of telomerase activity in the S100 extracts of 293 cells. The level of inhibition of the radioactive native substrate by these compounds is comparable to that caused by the cold native substrate. Even in the presence of high concentrations of the native nucleotide (1–2 mM), the 7-deaza nucleotides are able to inhibit telomerase activity with IC$_{50}$ values of less than 100 μM. These results suggest that both 7-deaza-dGTP and 7-deaza-dATP compete well with the natural substrates, dGTP and dATP.

7-Deaza-dGTP and 7-deaza-dATP can replace the native purine nucleotides, dGTP and dATP respectively. The total activity is weak and shorter ladders are formed when the 7-deaza analogues replace their native nucleotides. In comparison, 7-deaza purine nucleotides are effective substrates for a variety of other DNA polymerases (Mizusawa et al., 1986; McConlogue et al., 1988; Seela & Roling, 1991). There are several possibilities why N7 is a factor in telomerase processive activity.

One explanation for the selective effect of 7-deaza nucleotides involves the propensity of G-rich DNA sequences to form secondary structures involving G-quartets. The oligodeoxgribonucleotide having the sequence d(GGTTAGGGTTAG), corresponding to the human telomeric DNA sequence, forms G-quartet structure, as evidenced by $^1$H NMR. The imino proton spectrum of this sequence demonstrates diagnoshz signals in the region of 10–12 ppm indicating G-quartet formation. As the temperature of this sample is raised, these signals disappear as the G-quartet dissociates. In KCE-containing buffer, these signals up to 70° C. due to the ability of potassium ions to stabilize G-quartets. N7 is involved in G-quartet and hairpin structures. Replacing dG with dI in various telomeric sequences disrupted G-tetraplex formation but had no inhibitory effect on telomerase in vitro (Henderson et al., 1990). Furthermore, it has been shown that G-quartet structures may actually inhibit the initiation of telomerase activity (possibly by prevention of binding of telomerase to the oligonucleotide). However, it has been proposed that G-tetraplex structures can facilitate the translocation step (Zahler et al., 1991). Incorporation of the 7-deaza nucleotides can prevent formation of these structures. The oligodeoxyribonucleotide having the sequence d(GGTTAGG*GTTAG) when G* represents 2'-deoxy-7-deazaguanosine, in KCL-containing buffer displays only weak and broad imino proton signals in the G-quartet diagnostic region of 10–12 ppm in its low temperature $^1$H NMR spectrum. These weak signals disappear as the sample is warmed, and are no longer present at 25° C. making the translocation step more difficult. The result of this would be formation of shorter telomerase products. The telomerase ladder formed in the presence of 7-deaza-dATP is also prematurely shortened. While it is possible that N7 of adenine may also be involved in the formation of stable G-tetraplex structures, there is conflicting evidence to that effect (Murchie & Lilley, 1994; Balagutumoorthy & Brahmachari, 1994). Thus, it remains to be seen if addition of one 7-deaza-2'-deoxyadenine per TTAGGG repeat along the growing chain is sufficient to disrupt G-quartet structures or hairpin formation.

Another explanation for the effect of 7-deaza nucleotides on telomere formation is that incorporation of 7-deaza nucleotides destabilizes the DNA-telomerase RNA duplex or causes a conformational change resulting in complete dissociation of the growing strand from telomerase. It has been shown that replacing dG with 7-deaza-dG in alternating d(G-C) or d(C-G) oligomers does not change the conformation from B DNA but does result in a decrease in melting temperatures (Seela & Driller, 1989). Replacing dA with 7-deaza-dA in homoligomers dAdT also results in a decrease in stability. However, alternating d(A-T) oligomers in which dA is replaced by 7-deaza-dA are slightly more stable than d(A-T) oligomers. Replacing dA with 7-deaza-dA in homoligomers dAdT also results in a decrease in stability. However, alternating d(7-deazaA-T) oligomers are slightly more stable than d(A-T) oligomers (Seela & Thomas, 1995). In addition, replacing dA with 7-deaza-dA within poly dA tracts reduces the degree of bending (Seela et al., 1989). Dissociation of the enzyme from the growing strand may account for decrease in processivity of telomerase as the 7-deaza nucleotides are incorporated. Furthermore, a change in stability or conformational change caused by addition of one or more 7-deaza-dG's per TTAGGG repeat may cause telomerase to dissociate during the elongation step. This could be the cause of the shift and increase in number of pause sites observed in the presence of 7-deaza-dGTP but not 7-deaza-dATP.

A third explanation involves substrate inhibition. The substrate inhibition seen at higher 7-deaza-dGTP and 7-deaza-dATP concentrations has been observed for a variety of other enzymes (Dixon & Webb, 1979). Substrate inhibition is also seen in Tetrahymena in 10 mM dGTP (and 2.5 μM [α-$^{32}$P]TTP) which is 1,000–10,000 fold greater than the 1–10 μM dGTP required for optimum activity (Collins & Greider, 1995). Substrate inhibition could be due to two mechanisms (Dixon & Webb, 1979). In the first mechanism, the nucleotides can bind to the telomerase active site to form other ineffective telomerase-nucleotide complexes which inhibit telomerase activity. The less effective binding modes have a higher K$_m$ than the correct mode so that inhibition becomes more apparent only when higher concentrations of substrate is present.

In the second mechanism, the nucleotides can bind to a site other than the active site which causes a conformational change resulting in inhibition. This binding would have a lower affinity than the active site binding so that inhibition becomes more apparent with increasing substrate concentrations. When the 7-deaza nucleotide competes with the radioactive nucleotide at limiting concentrations, 1–3 μM, the observed IC$_{50}$ value most likely reflects the direct competition between the cold and labeled nucleotide. However, the observed inhibition of telomerase activity by the 7-deaza nucleotides in the presence excess concentrations of the nonradioactive native nucleotide may be due to substrate inhibition. Details of human telomerase structure are unknown at this time; thus, how the substitution of a carbon for N7 is responsible for the observed substrate inhibition is not yet fully defined.

K. Pharmaceutical Compositions

The pharmaceutical compositions disclosed herein may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier") includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral prophylaxis the compounds may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The phrase "pharmaceutically acceptable" refers to molecular entities and compositions that do not produce an allergic or similar untoward reaction when administered to a human. The preparation of an aqueous composition that contains an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA standards.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Abbreviations used: Tris-HCl, Tris(hydroxymethyl)-aminomentane hydrochloride; MEM, minimal essential medium; HEPES, N-[2-Hydroxyethyl]piperazine-N'-[2-ethansulfonic acid]; PMSF, Phenylmethylsulfonic acid; EDTA, ethylenediaminetetraacetate; dGTP, 2'-deoxyguanosine-5'-triphosphate; dATP, 2'-deoxyadenosine-5'-triphosphate; TTP, 2'-deoxythymidine-5'-triphosphate; dG, 2'deoxyguanosine; dA, 2'-deoxyadenosine; dC, 2'-deoxycytidine Materials Oligonucleotide primers (Genosys), dNTP's including 7-deaza-dGTP and 7-deaza-dATP (Pharmacia), [$\alpha$-$^{32}$P]dGTP and [$\alpha$-$^{32}$P]dATP (Dupont NEN), RNase A, PMSF, pepstatin A, and leupeptin, and other chemicals (Sigma).

Methods

1. Telomerase Preparation

Telomerase was prepared from transformed human embryonic kidney 293 cell line. Human embryonic kidney 293 cells were grown in Joklik's modified MEM medium (Sigma, St Louis, Mo.) supplemented with 5% fetal bovine serum at 37° C. in a humidified atmosphere with 5% $CO_2$. The cells were subcultured at 1–2×10$^5$ cells/ml twice a week. When the cells grew to approximately 1×10$^6$ cells/ml, the cells (~2×10$^9$ cells) were centrifuged and transferred into polypropylene centrifuge (50 ml) tubes and kept on ice. The cells were then centrifuged in a (Beckman GS-6R) centrifuge at 1200 RPM for 10 minutes at 4° C., and resuspended in PBS. The washed cells were resuspended in 15 ml Hypobuffer Mix (10 mM HEPES, pH 8.0, 3 mM KCl, 1 mM $MgCl_2$, 1 mM dithiothreitol, 1 $\mu$M leupeptin, 0.1 mM PMSF, 10 $\mu$M pepstatin, 0.83 $\mu$g/ml chymostatin, 0.83 $\mu$g/ml antipain, and 43.2 units/ml RNase Guard) and centrifuged. The cell pellets were resuspended in 0.75×volumes Hypobuffer [Hypobuffer Mix+40 units/ml RNase Guard (Pharmacia, N.J.) to allow the cells to swell. The cell suspensions were homogenized to allow the telomerase to "leak" into the cytosolic fraction. The lysate was then poured into new, autoclaved, 3 ml polyallomer ultracentrifuge tubes and centrifuged at 100,000×g for 1 hour at 4° C. A top lipid layer was carefully removed and discarded, and the supernatant was collected. 1/50 of the volume of 5 M NaCl was added to the clear supernatant fluid to achieve a final concentration of 0.1 M. Sterile glycerol was added until the final glycerol concentration was 20%. The enzyme solution was aliquoted into Eppendorf tubes and quickly frozen in liquid nitrogen and stored at −70° C.

2. Conventional Telomerase Assay ($^{32}$P-dGTP as Radiolabel Substrate)

The assay is based on the ability of the telomerase enzyme in the S100 fractions to recognize an 18-base DNA primer with the DNA sequence (TTAGGG)$_3$. DNA polymerization initiates from the 3'-OH group of the oligonucleotide. By reading from its complementary internal RNA template, telomerase adds a repeated set of 5'-TTAGGG-3' to the original 18-base primer. Non-synchronous "starts" and "terminations" among the different enzyme complexes result in a degenerative set of different length DNA primers occurring in 6-base increments. Incorporation of [$\alpha$-$^{32}$P]dGTP at the guanine positions of the 5'-TTAGGG-3' sequence allows the newly synthesized DNA fragments to be visualized by autoradiography. The resulting image forms the characteristic "ladder" structure that is used to identify telomerase activity. The images are scanned using a phosphoimager or laser densitometer (Molecular Dynamics, Sunnyvale, Calif.). Comparisons of the total volumes under the corresponding peaks are used to quantitate the total amount of [$\alpha$-$^{32}$P] incorporated in the primer extension reaction.

The telomerase assay was initiated by mixing 20 $\mu$l of 2×reaction mix (100 mM Tris-OAc, pH 8.5, 100 mM KOAc, 10 mM P-mercaptoethanol, 2 mM spermidine, 2 mM $MgCl_2$, 2 mM dATP, 2 mM dTTP, 2 $\mu$M oligo primer, potential inhibitors of interest at the appropriate concentration, and 50 $\mu$Ci [$\alpha^{32}$-P]dGTP) with 20 $\mu$l of S100 enzyme extract. The reaction mixture was then incubated at 30° C. for 1 hour. The reaction was stopped by incubating sequentially with 50 $\mu$l of the stop solution (10 mM Tris pH 7.5, 20 mM EDTA, 0.1 mg/ml RNase A) and 50 $\mu$l of deproteinase solution (10 mM Tris pH 7.5, 0.5% SDS, 0.3 mg/ml Proteinase K). The mixture was extracted with 50% phenol/50% chloroform (v/v). The DNA was then precipitated by adding 2.5×volumes of cold EtOH and letting it stand overnight at −70° C. The DNAs were separated on an 8% polyacrylamide/7M urea denaturing gel at 1600 V for 1.5 hours. The gel was dried and exposed to Kodak XAR-5 film to gel in −70° C. Typical autoradiographic exposures required 3–14 days.

3. Modified Telomerase Assay ($^{32}$P-dATP as Radiolabeled Substrate)

In the conventional telomerase assay, the concentrations of both non-radiolabeled nucleotides, dATP and dTTP, are 1 mM, and the concentration of the radiolabeled [$^{32}$P]dGTP is 1.56 $\mu$M. Because of the high concentration of dATP and dTTP, the standard assay may not be suitable for determining the potential telomerase inhibition of any "Adenine or Thymine" analogs. A modified alternative telomerase assay was developed which uses dGTP (1 mM) and dTTP (1 mM) as the non-radiolabeled substrates and 3.12 $\mu$M [$\alpha^{32}$P]-dATP as the radiolabeled substrate. All other chemicals and reaction conditions are identical to the conventional assay.

4. Testing Selected Nucleoside Triphosphates as Telomerase Substrates

As described in Section 2, telomerase catalyzes the incorporation of dATP, dTTP and [$\alpha$-$^{32}$P]dGTP into a (TTAGGG)$_3$ primer. In order to determine whether dATP analog can be incorporated into telomere, native dATP in the standard telomerase reaction is replaced with various concentrations of dATP analogs. Following the reaction, telomeric products are isolated and analyzed as described in Section 2. Similarly, native dTTP in the standard telomerase reaction can be replaced by a structurally modified dTTP analog to test whether the dTTP analog can be used as a telomerase substrate.

In order to evaluate whether or not a dGTP analog can be incorporated by telomerase, native dGTP in the modified telomerase reaction (1 mM dGTP, 1 mM dTTP and 3.12 $\mu$M [$\alpha^{32}$P]dATP) is replaced with the dGTP analog.

5. Testing Selected Nucleotides for Their ability to Destabilize of G-quartet Formation.

The oligodeoxyribonucleotide having the sequence d(GGTTAGGGTTAG), corresponding to the human telomeric DNA sequence, was prepared using standard automated solid phase synthesis techniques employing a ten micromole synthesis on an Applied Biosystems Model 381A automated DNA synthesizer. Solid support and reagents were purchased from Biogenex, Glen Research, or Applied Biosystems, South San Francisco, Calif. The DNA sample was deprotected in concentrated $NH_4OH$ at 55° C. overnight, purified by reverse phase HPLC on a C18 column (Dynamax-300A) and then dialyzed extensively against deionized water. NMR samples were prepared by reconstituting lyophilized DNA in 90% $H_2O$/10% $D_2O$ containing 1 mM EDTA/50 mM potassium phosphate and either 100 mM KCl or 100 mM NaCl. NMR experiments were carried out on a Bruker AMX 500 MHz spectrophotometer using a 1-1 echo pulse sequence with maximum excitation centered as 12.0 ppm. At temperatures as high at 70° C., the NMR spectrum of the sample dissolved in KCl buffer displayed characteristic resonances in the region of 10–12 ppm that corresponded to the imino protons of the G-quartet structure. The same sample dissolved in NaCl buffer only displayed these imino resonances at 10–12 ppm up to temperatures of 60° C., indicating that these resonances correspond to the potassium-stabilized G-quartet structure.

In a similar manner, the fully protected phosphoramidite of a selected nucleotide analog was used in an automated solid phase DNA synthesizer to synthesize a oligodeoxyribonucleotide having the same sequence but with one natural base substituted with the nucleotide analog, for example d(GGTTAGG*GTTAG) where G* represents a 7-deaza-2'-deoxyguanosine residue. After cleavage from the solid support, deprotection and purification, the oligodeoxyribonucleotide is dissolved in 90% $H_2O$/10% $D_2O$ containing 100 mM KCl/1 mM EDTA/50 mM potassium phosphate. The imino NMR spectrum of this oligodeoxyribonucleotide is acquired at various temperatures from about 0°C.–80° C. and the presence of the diagnostic G-quartet imino is indicated by the presence of resonances at 10–12 ppm.

6. Growth Inhibition Studies

Exponentially growing cells (1–2×10³ cells, unless specified otherwise) in 0.1 ml medium were seeded on day 0 in a 96-well microtiter plate. On day 1, 0.1 ml aliquots of medium containing graded concentrations of test analogs were added in duplicate to the cell plates. After incubation at 37° C. in a humidified incubator for 6 days, the plates were centrifuged briefly and 100 μl of the growth medium was removed. Cell cultures were incubated with 50 μl of 3-(4,5-dimethylthiazol-2-yl)-2,5-diphenyl-tetrazolium bromide, (MTT) at a concentration of 1 mg/ml in Dulbecco's phosphate buffered saline (PBS)) for 4 hr at 37° C. The resulting purple formazan precipitate was solubilized with 200 μl of 0.04 N HCl in isopropyl alcohol. Absorbance was monitored in a BioRad Model 3550 Microplate Reader at a test wavelength of 570 nm and a reference wavelength of 630 nm. The absorbance was transferred to a PC 486 computer. The $IC_{50}$ values were determined by a computer program (EZ-ED50) that fits all the data to the following four-parameter logistic equation:

$$Y = \frac{A_{max} - A_{min}}{1 + (X/IC^{50})^n} + A_{min}$$

where $A_{max}$ is the absorbance of control cells, $A_{min}$ is the absorbance of cells in the presence of highest agent concentration, Y is the observed absorbance, X is the agent concentration, $IC_{50}$ is the concentration of agent that inhibits the cell growth by 50% of control cells (based on the absorbance) and n is the slope of the curve.

7. Detection of AZTTP Formation in Cells

Tumor cells were incubated with graded concentrations of [³H]AZT at 37° C. At the indicated intervals, 2×10⁷ cells were centrifuged at 1000×g for 6 min and were washed once with 5 ml of cold 0.9% NaCl. Cold perchloric acid (4%; 0.45 ml) was added to the pellets, and the tubes were vortexed vigorously. The cold perchloric acid mixture was placed in ice for 20 min and was vortexed occasionally. The precipitated protein and nucleic acids were removed by centrifugation at 3000×g for 20 min at 4° C. The supernatant fluids (4° C.) were then neutralized to pH 6.5 to 7.5 by 5 N KOH, the precipitated potassium perchlorate was removed by centrifugation, and the supernatant fluids were frozen for BPLC analysis. HPLC analysis was performed on a Beckman HPLC. The separation was achieved by a linear gradient elution of potassium phosphate buffer pH 4.5 (10 to 500 mM on a Whatman strong anion exchange column, Partsil 10 SAX.

8. Determination of the Effect of Agents on Telomere Length

HeLa cells were cultured in DMEM medium supplemented with 10% fetal bovine serum in the presence of testing agents (at the indicated concentration ~$IC_{10}$ value). The cells were subcultured every 3.5 days. The cells were grown for 4 passages which is equivalent to ~12 cell population doublings. At the appropriate cell passage, ~1×10⁷ HeLa cells were harvested by trypsin treatment. High quality DNA (large in size) was prepared by Proteinase K and RNase treatment, followed by phenol extraction. DNA isolated from the control and analog-treated HeLa cells was digested with restriction enzyme MseI to completion. Restriction digested DNAs were electrophoresed on a 0.8% agarose gel. The gel was Southern blotted onto a nitrocellulose or nylon membrane and the membrane was probed by hybridization with a telomere specific sequence containing TTAGGG repeats. The membrane was exposed to autoradiographic film. After development, the signals in each lane were scanned and quantitated by video (CCD) densitometry. The median length, peak, and other curve characteristics were determined by computer (using Image 1.5). Duplicate samples were analyzed for each compound.

9. Induction of Dicentric Chromosome by a Telomerase Inhibitor

The same cells grown for the telomere analysis were plated for chromosome preparation. Metaphase cells were harvested, fixed by methanol/acetic acid and the chromosomes spread on slides for fluorescent in situ hybridization analysis. The spreads were hybridized with a centromere probe and detected by a fluorescein tag. The number of fused chromosomes per cell was calculated for each compound tested.

EXAMPLE 1

Figure 4:
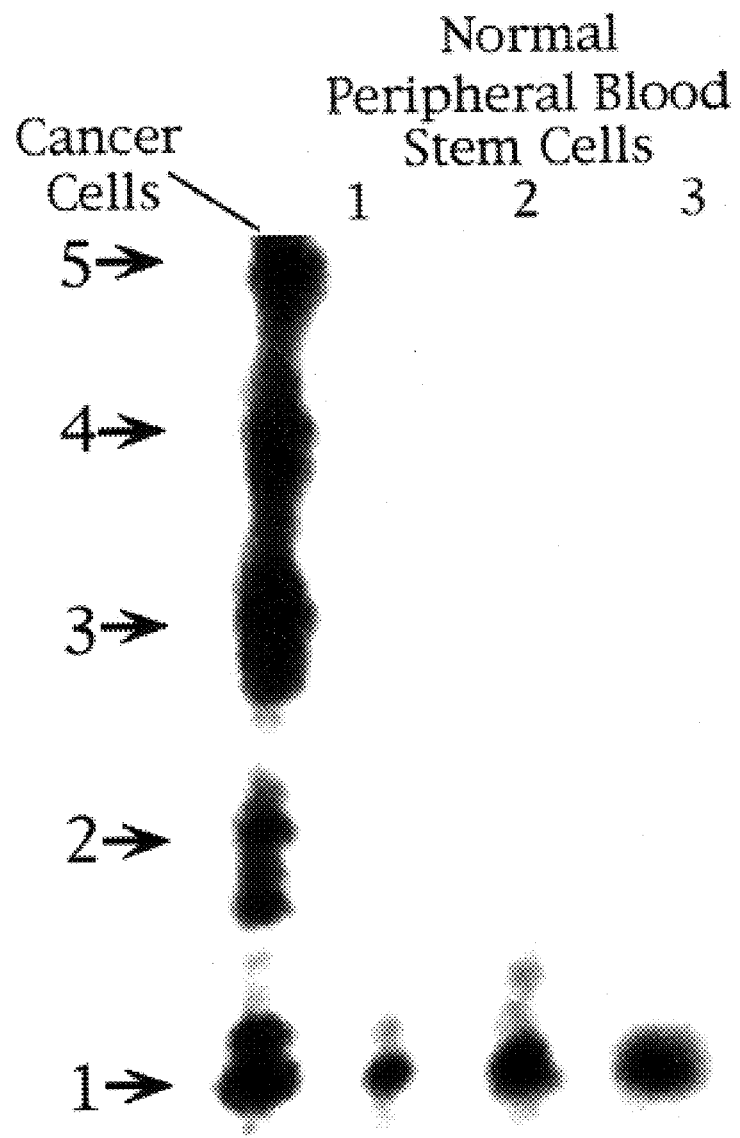
FIG. 4. shows the production of processive telomerase by cancer cells and the production of non-processive telomerase by normal cells. Telomerase incorporates labeled dGTP into a telomeric primer by adding a telomeric repeat or repeats. The labeled primers were electrophoresed and visualized by autoradiography. Lane one is from human renal cell carcinoma cancer cells. The telomerase product bands are indicated by numbered arrows. Lanes 1, 2, and 3 show telomerase activity from normal human blood stem cells.
Figure 5A:
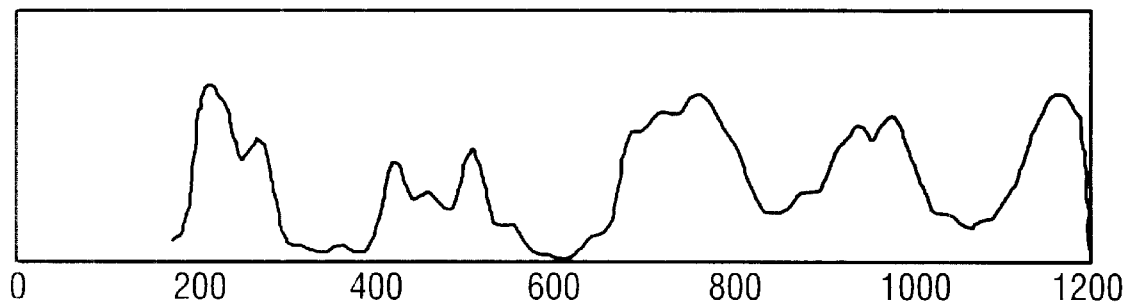
FIG. 5A, B, C and D shows the densiometric scans of telomerase activities from cancer cells and normal stem cells.
Figure 5B:
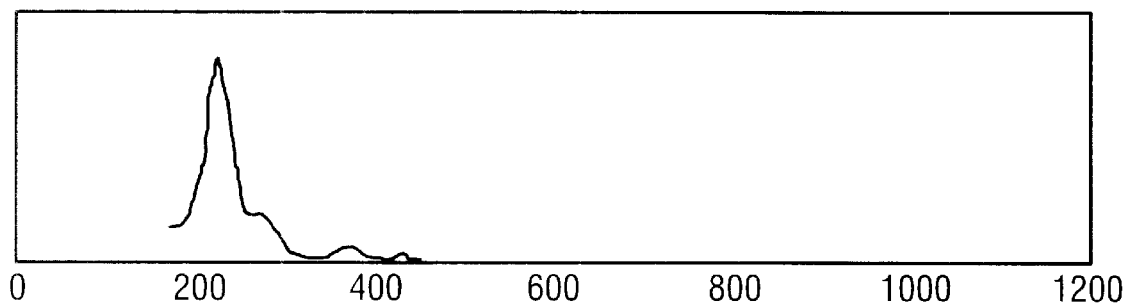
FIG. 5B, C and D show the non-progressive telomerase activity of normal cells.
Figure 5C:
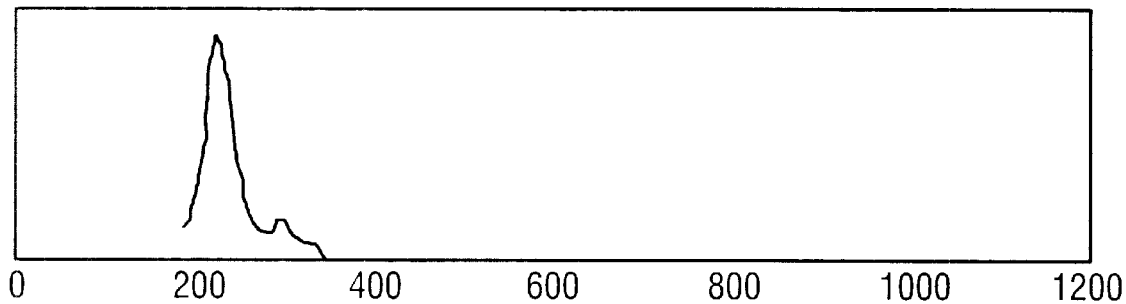
Figure 5D:
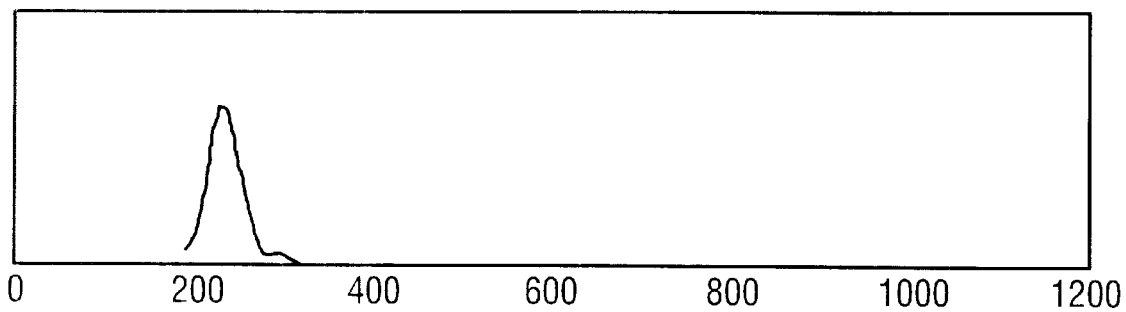

A. Normal Cells Produce Non-Processive Telomerase While Cancer Cells Produce Processive Telomerase Telomerase was prepared from various human cancer cells and normal stem cells. Telomerase activity was compared using the conventional telomerase assay (see section 2 under Materials and Methods) and modified conventional telomerase assay see section 3 under Materials and Methods). Telomerase incorporates labeled dGTP into a telomeric primer by adding a telomeric repeat or repeats. The labeled primers were electrophoresed and visualized by autoradiography. Telomerase activity is indicated in FIG. 4; the first lane on the left is from human renal cell carcinoma cancer cells. The telomerase product bands are indicated by numbered arrows. This activity is processive as indicated in FIG. 4 by the multiple bands produced by the cancer telomerase adding multiple telomeric repeats. The telomerase activities in lane marked 1,2, and 3 are from normal human blood stem cells. These normal telomerase activities are non-processive as indicated by the single band produced by normal telomerase adding a single repeat to the primer.

B. Densitometric Scans of the Telomerase Activities from Cancer Cells and Normal Stem Cells The density of signal in the lanes shown in the activity scan in FIG. 5 was determined along each lane. The scans show in a quantitative manner that cancer cell telomerase activity is processive and distinctly different from the non-processive telomerase activity of normal cells. The numerous peaks past coordinate position 300 are indicative of processive telomerase activity. Normal cells essentially have no peaks past position 300 and only have the first peak, which is indicative of non-processive telomerase activity.

C. Conversion of Processive Telomerase to Non-processive Telomerase

Figure 6:
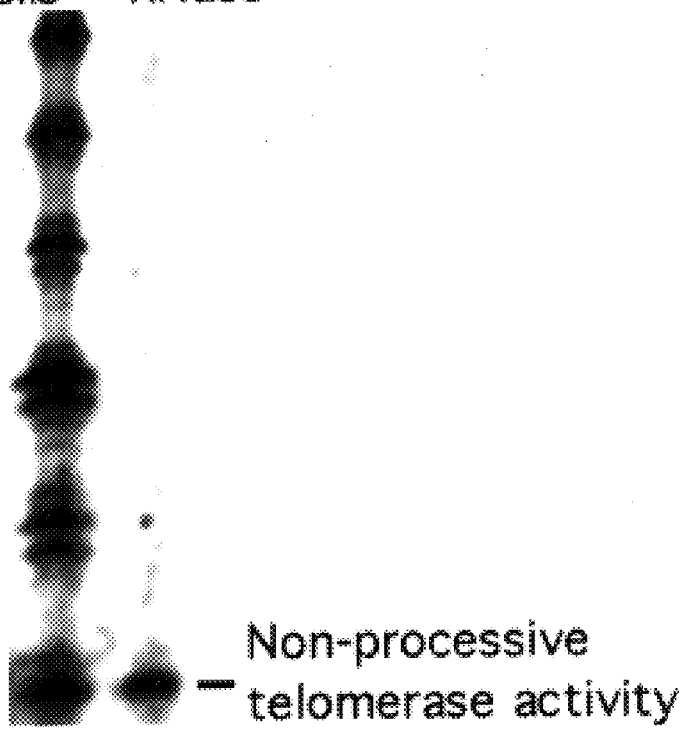
FIG. 6 shows the conversion of processive telomerase to non-processive telomerase. Human cancer telomerase was incubated with limited amounts of RNase A, and assayed by the incorporation of labeled dGTP into the telomerase products. The products were separated by electrophoresis, and visualized by autoradiography. The left lane of autoradiogram below shows the human cancer telomerase activity without treatment and the right lane shows the same telomerase activity with RNase treatment.

Human cancer telomerase was incubated with limited amounts of RNase A, and then assayed using the conventional telomerase assay where labeled dGTP is incorporated into the telomerase products. The products were separated by electrophoresis, and visualized by autoradiography. The left lane of autoradiogram in FIG. 6 shows the human cancer telomerase activity without treatment and the right lane shows the same telomerase activity with RNase treatment. The limited amount of RNase partially cleaved the telomerase RNA component so that the telomerase acts non-processively. This is consistent with the RNA component having structures required for the processive function of telomerase. These structures can be targeted to convert a cancer's aggressive processive telomerase activity to a non-aggressive or benign and non-processive activity.

Figure 7:
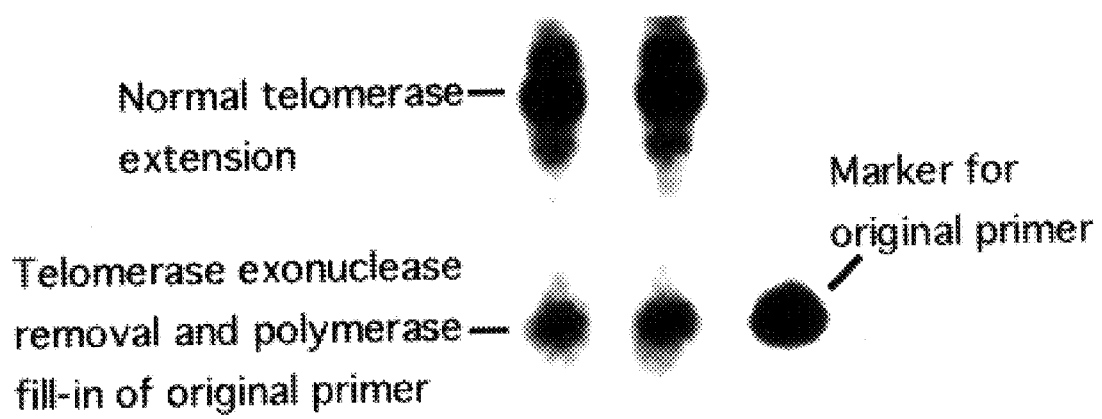
FIG. 7 shows the modulation of human telomerase exonuclease to promote shortening of telomeres. Human cancer telomerase was incubated in the presence of a limited amount of dTTP. Telomerase activity was determined by the conventional assay using an 18-mer telomeric sequence primer, and the products were separated by electrophoresis. The two left lanes show products revealing that telomerase has removed a significant amount of the telomeric sequence as the result of a 3' to 5' exonuclease. This activity was stimulated by the limitation of dTTP (e.g. 100 mm) and is not normally observed under normal conditions (e.g. 1 mm).

D. Modulation of Human Telomerase Exonuclease to Promote Shortening of Telomeres Human processive telomerase exhibits a 3' to 5' exonuclease activity that can be stimulated to remove telomeric sequence rather than synthesize telomerase sequence. Human cancer telomerase was incubated in the presence of a limited amount of dTTP. The autoradiogram in FIG. 7 shows the exonuclease activity of telomerase where a reduction in nucleotides such as dTTP and a change in the DNA primer substrate can induce the exonuclease activity. As the exonuclease removes G residues from the primer, the polymerase of telomerase can fill them back in, thus labeling the original primer with labeled dGTP.

Telomerase activity was determined by the conventional assay using an 18-mer telomeric sequence primer, and the products were separated by electrophoresis. The two left lanes show products revealing that telomerase has removed a significant amount of the telomeric sequence as the result of a 3' to 5' exonuclease. This activity was stimulated by the limitation of dTTP (e.g. 100 mm) and is not normally observed under normal conditions (e.g. 1 mm).

EXAMPLE 2

Inhibition of Human Cancer 293 Cell Telomerase Activity by Selected Thymidine Triphosphates.

The following examples demonstrate that thymidine triphosphates with modifications on the 2'-deoxyribose moiety or on the heterocyclic moiety are capable of inhibiting human telomerase activity. The studies were performed using the conventional telomerase assay in which the competing dTTP concentration is in the range of 1–2 mM.

A. Inhibition of Human Cancer Telomerase by 3'-Azido-3'-deoxythymidine-5'-triphosphate (AZTTP, NA010).

Figure 8:
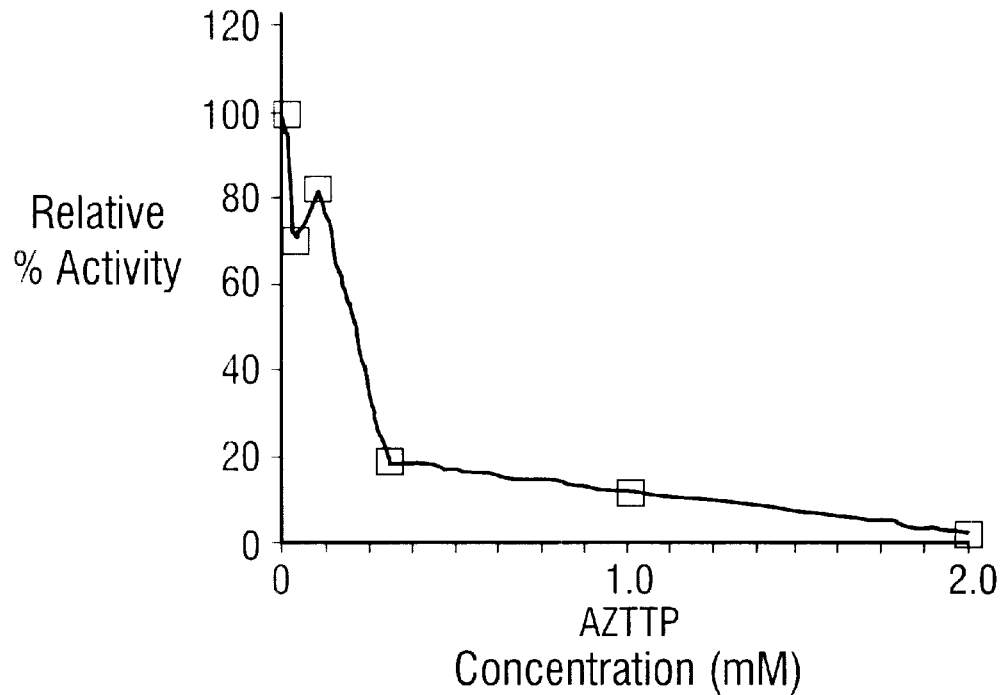
FIG. 8 shows the inhibition of human cancer telomerase by 3'-azido-3'-deoxythymidine-5'-triphosphate (AZTTP). Telomerase was prepared from 293 cells and activity assayed by the incorporation of labeled dGTP into a telomeric primer. Telomerase was incubated with concentrations of AZTTP ranging from 0 to 2 mM.

Telomerase was prepared from 293 cells. The conventional telomerase assay was performed where telomerase incorporates labeled dGTP into a telomeric primer and the labeled primers are electrophoresed and signal quantitated by autoradiography and densitometry. Telomerase was incubated with concentrations of AZTTP ranging from 0 to 2 mM. The $IC_{50}$ was ~200 $\mu$M. The relative percent activity of AZTTP at different concentrations is shown in FIG. 8.

B. Inhibition of Human Cancer Telomerase by 2', 3'-Dideoxythymidine5'-triphosphate (ddTTP, NA001).

Figure 9:
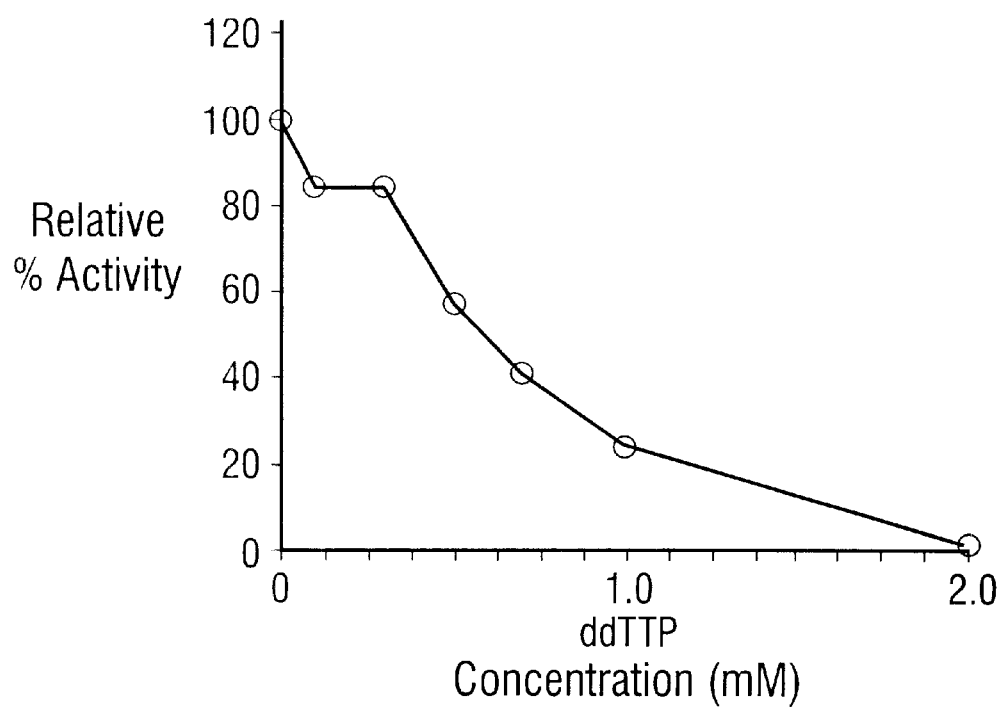
FIG. 9 shows the inhibition of human cancer telomerase by 2', 3'-dideoxythymidine-5'-triphosphate (ddTTP). Telomerase was prepared from 293 cells and activity assayed by the incorporation of labeled dGTP into a telomeric primer. Telomerase was incubated with concentrations of ddTTP ranging from 0 to 2 mM.

Telomerase was prepared from 293 cells. The conventional telomerase assay was performed where telomerase incorporates labeled dGTP into a telomeric primer and the labeled primers are electrophoresed and signal quantitated by autoradiography and densitometry. Telomerase was incubated with concentrations of ddTTP ranging from 0 to 2 mM. The $IC_{50}$ was ~500 $\mu$M. The relative percent activity of the ddTTP with increasing concentration is shown in FIG. 9.

C. Inhibition of Human Cancer Telomerase by 3'-Amino-2'-deoxythymidine-5'-triphosphate (3'-Amino-TTP, NA005).

Figure 10:
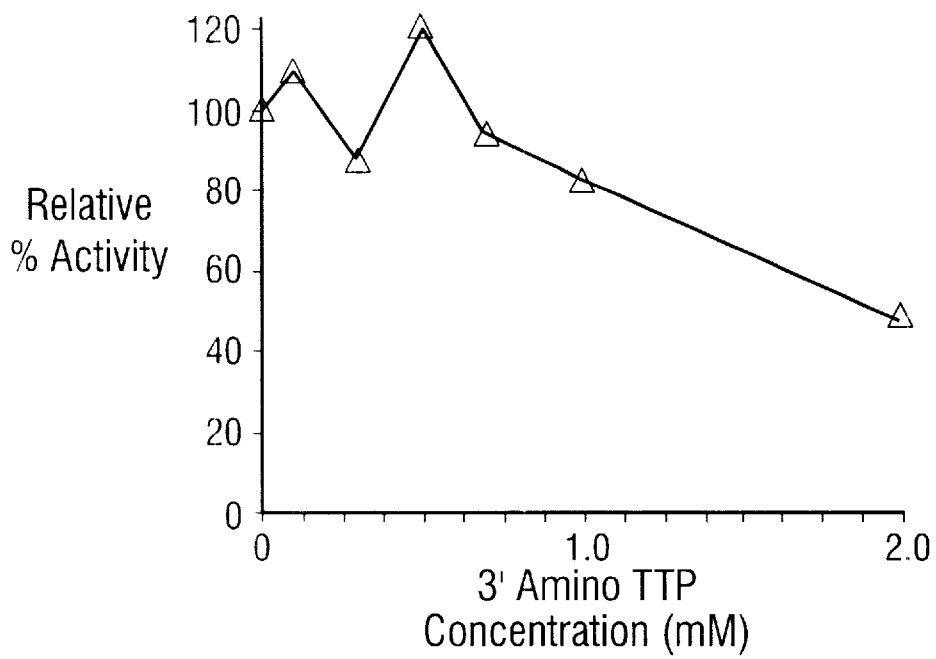
FIG. 10. shows the inhibition of human cancer telomerase by 3' -amino-2'-deoxythymidine-5'-triphosphate (3'-amino-TTP). Telomerase was prepared from 293 cells and activity assayed by the incorporation of labeled dGTP into a telomeric primer. Telomerase was incubated with concentrations of 3'-Amino-TTP ranging from 0 to 2 mM.

Telomerase was prepared from 293 cells. The conventional telomerase assay was performed where telomerase incorporates labeled dGTP into a telomeric primer and the labeled primers were electrophoresed and signal quantitated by autoradiography and densitometry. Relative activity change with concentration is shown in FIG. 10. Telomerase was incubated with concentrations of 3'-Amino-TTP ranging from 0 to 2 mM. The $IC_{50}$ was ~2 mM.

D. Inhibition of Human Cancer Telomerase by 5-Allylamino-2'-deoxythymidine-5'-triphosphate (NA021).

NA021 is an analog of dTTP in which the methyl group is replaced with an allylamino group. NA021 demonstrated a concentration dependent inhibition of 293 cell telomerase with an estimated IC50 value of ~0.5 mM. This is shown in Table 2.

TABLE 2

| NA021(mM) | % of Control |
|---|---|
| 10 | 100 |
| 0.125 | 51 |
| 0.25 | 70 |
| 0.5 | 43 |
| 1.0 | 33 |
| 2.0 | 30 |

EXAMPLE 3

Inhibition of Human Cancer 293 Cell Telomerase Activity by Selected Deoxyguanosine Triphosphates.

The following examples demonstrate that 2'-deoxyguanosine triphosphates with modifications on the phosphate moiety, on the sugar moiety or on the heterocyclic moiety are capable of inhibiting human telomerase activity. Since the testing analogs are dGTP analogs, the inhibitory activity was evaluated using the conventional telomerase assay.

A. Lack of Telomerase Inhibitory Activity by Guanosine-5'-β, γ-methylene triphosphate (NA011).

Compound NA011—(a guanine ribonucleotide and not a 2'-deoxyribonucleotide) was inactive as telomerase inhibitor. Compared with the results for compound NA014, 2'-deoxyguanosine-5'-α,γ-methylene triphosphate (see Example 3. B), the 2'-deoxyribose appears to be required for inhibitory activity.

TABLE 3A

| NA011(mM) | % of Control |
|---|---|
| 0.125 | 82 |
| 0.25 | 63 |

TABLE 3A-continued

| NA011(mM) | % of Control |
|---|---|
| 0.5 | 86 |
| 1.0 | 70 |
| 2.0 | 65 |

B. Inhibition of Human Cancer Telomerase Activity by 2'Deoxyguanosine-5'-β,γ-methylene triphosphate (NA014)

NA014 is a dGTP analog with a modification on the phosphate moiety in which the oxygen atom linking the β and γ phosphate groups is replaced with a methylene group. Using the conventional telomerase assay, NA014 demonstrated a concentration-dependent inhibition of human 293 cells telomerase activity.

TABLE 3B

| NA014(mM) | % of Control |
|---|---|
| 0. | 100 |
| 0.125 | 60 |
| 0.25 | 38 |
| 0.5 | 42 |
| 1.0 | 40 |
| 2.0 | 28 |

C. Inhibition of Human Cancer Telomerase Activity by 2'-Deoxyguanosine-5'-O-(1-thiotriphosphate) (NA013)

NA013 is a dGTP analog with a modification on the phosphate moiety in which the α(P=O) bond is replaced with a P=S bond. Using the conventional telomerase assay, NA013 demonstrated a concentration-dependent inhibition of human 293 cell telomerase activity.

TABLE 3C

| NA013(mM) | % of Control |
|---|---|
| 0. | 100 |
| 0.125 | 75 |
| 0.25 | 47 |
| 0.5 | 0 |
| 1.0 | 0 |
| 2.0 | 0 |

D. Inhibition of Human Cancer Telomerase Activity by 2', 3'-dideoxyguanosine-5'-triphosphate (NA020).

NA020 is a dGTP analog in which the 2'-deoxyribose moiety is replaced with a 2', 3'-dideoxyribose moiety. Using the conventional telomerase assay, NA020 completely at concentrations as low as 12.5 μM (0.0125 mM) inhibits human 293 cell telomerase activity.

TABLE 3D

| NA020(mM) | % of Control |
|---|---|
| 0. | 100 |
| 0.0125 | 0 |
| 0.025 | 0 |
| 0.05 | 0 |
| 0.1 | 0 |
| 0.2 | 0 |
| 0.5 | 0 |
| 1.0 | 0 |

E. Inhibition of Human Cancer Telomerase Activity by 7-Deaza-2'-deoxyguanosine-5'-triphosphate (NA022).

NA022 is an example of a dGTP analog in which the heterocyclic base, guanine, is replaced with a 7-deazaguanine. Using both the conventional telomerase assay and the modified assay, NA022 demonstrated concentration-dependent inhibition of human 293 cell telomerase activity.

TABLE 3E

| NA022(μM) | % of Control |
|---|---|
| 0. | 100 |
| 1.0 | 99 |
| 2.5 | 114 |
| 5.0 | 67 |
| 7.5 | 81 |
| 10 | 24 |
| 25 | 27 |
| 50 | 18 |
| 75 | 0 |
| 100 | 0 |

EXAMPLE 4

Inhibition of Human Cancer 293 Cell Telomerase Activity by Selected Deoxyadenosine Triphosphates The following examples demonstrate that 2'-deoxyadenosine triphosphates with modifications on the phosphate moiety, on the sugar moiety or on the heterocyclic moiety are capable of inhibiting human telomerase activity. Both conventional and modified telomerase assays were used to determine the inhibitory activity of selected deoxyadenosine triphosphate analogs.

A.i. Lack of Inhibition of Human Cancer Telomerase Activity by 2'-Deoxyadenosine-5'-β,γ-methylene triphosphate (NA004) Using the Conventional Telomerase Assay.

NA004 is a dATP analog with a modification on the phosphate moiety in which the oxygen atom linking the β and γ phosphate groups is replaced with a methylene group. Using the conventional telomerase assay, NA004 demonstrated no inhibition of human 293 cells telomerase activity up to 2 mM.

TABLE 4Ai

| NA004(mM) | % of Control |
|---|---|
| 0. | 100 |
| 0.125 | 70 |
| 0.25 | 72 |
| 0.5 | 88 |
| 1.0 | 98 |
| 2 | 99 |

A.ii. Inhibition of Human Cancer Telomerase Activity by 2'-Deoxyadenosine-5'-β,γ-methylene triphosphate (NA004) Using the Modified Telomerase Assay.

On the other hand, NA004 demonstrated a concentration-dependent inhibition of human 293 cell telomerase activity using the modified telomerase assay in which the competing radioactive nucleotides is 3.12 μM [α$^{32}$P]dATP.

TABLE 4Aii

| NA004(mM) | % of Control |
|---|---|
| 0. | 100 |
| 0.125 | 6 |
| 0.25 | 1.7 |
| 0.5 | 0 |
| 1.0 | 0 |

TABLE 4Aii-continued

| NA004(mM) | % of Control |
|---|---|
| 2 | 0 |

B.i. Lack of Inhibition of Human Cancer Telomerase Activity by 2'-Deoxyadenosine-5'-O-(1-thiotriphosphate) (NA006) Using the Conventional Telomerase Assay.

NA006 is an example of a dATP analog with a modification on the phosphate moiety in which the a (P=O) bond is replace with a P=S bond. Using the conventional telomerase assay, NA006 demonstrated no inhibition of human 293 cells telomerase activity up to 2 mM.

TABLE 4Bi

| NA006(mM) | % of Control |
|---|---|
| 0 | 0 |
| 0.125 | 120 |
| 0.25 | 103 |
| 0.5 | 103 |
| 1.0 | 100 |
| 2 | 113 |

B.ii. Inhibition of Human Cancer Telomerase Activity by 2'-Deoxyadenosine-5'-O-(1-thiotriphosphate) (NA006) Using the Modified Telomerase Assay.

On the other hand, NA006 demonstrates a concentration-dependent inhibition of human 293 cell telomerase activity using the modified telomerase assay in which the competing radioactive nucleotides is 3.12 $\mu$M [$\alpha^{32}$P]dATP.

TABLE 4Bii

| NA006(mM) | % of Control |
|---|---|
| 0 | 100 |
| 0.125 | 0 |
| 0.25 | 0 |
| 0.5 | 0 |
| 1.0 | 0 |
| 2 | 0 |

C.i. Lack of Inhibition of Human Cancer Telomerase Activity by 2',3'-dideoxyadenosine-5'-triphosphate (NA007) Using the Conventional Telomerase Assay.

NA007 is an example of a dATP analog in which the 2'-deoxyribose moiety is replaced with a 2',3'-dideoxyribose moiety. Using the conventional telomerase assay, NA007 demonstrated no inhibition of human 293 cells telomerase activity up to 2 mM.

TABLE 4Ci

| NA007(mM) | % of Control |
|---|---|
| 0 | 100 |
| 0.125 | 118 |
| 0.25 | 116 |
| 0.5 | 141 |
| 1.0 | 126 |
| 2 | 133 |

C.ii. Inhibition of Human Cancer Telomerase Activity by 2', 3'-dideoxyadenosine-5'-triphosphate (NA007) Using the Modified Telomerase Assay.

On the other hand, NA006 demonstrated a concentration-dependent inhibition of human 293 cell telomerase activity using the modified telomerase assay in which the competing radioactive nucleotides is 3.12 $\mu$M [$\alpha^{32}$P]dATP.

TABLE 4Cii

| NA007(mM) | % of Control |
|---|---|
| 0 | 100 |
| 0.125 | 0 |
| 0.25 | 0 |
| 0.5 | 0 |
| 1.0 | 0 |
| 2 | 0 |

D. Inhibition of Human Cancer Telomerase Activity by 7-Deaza-2'-deoxyadenosine-5'-triphosphate (NA023) using both the Conventional and Modified Telomerase Assays.

NA023 is an example of a dATP analog in which the heterocyclic base, adenine, was replaced with a 7-deazaadenine. Using both the conventional telomerase assay and the modified assay, NA023 demonstrated concentration-dependent inhibition of human 293 cell telomerase activity.

TABLE 4D

| NA023($\mu$M) | % of Control |
|---|---|
| 0 | 100 |
| 1.0 | 69 |
| 2.5 | 46 |
| 5.0 | 57 |
| 7.5 | 40 |
| 10 | 23 |
| 25 | 4 |
| 50 | 0 |
| 75 | 0 |
| 100 | 0 |

EXAMPLE 5

Use of Selected Nucleoside Triphosphates as Telomerase Substrate

Human cancer telomerase catalyzes the polymerization of a (TTAGGG)$_3$ primer using dTTP, dATP, dGTP. Using either the conventional or modified telomerase assay, the following examples illustrate that selected nucleoside triphosphate analogs can replace the native nucleotides (dTTP, dATP, and dGTP). In some examples, incorporation of these nucleotide analogs leads to a prematurely shorten telomere. These examples demonstrate a novel method of affecting telomerase activity.

A. Incorporation of 2'-Deoxyadenosine-5'-β,γ-methylene triphosphate (NA004) by Human Cancer Telomerase NA004, a dATP analog with a 5'-β,γ-methylene group, is able to replace dATP and become incorporated into telomeric ladders. Using the conventional telomerase assay, NA004 was shown to be incorporated at all the concentrations tested (0.125–2 mM).

B. Incorporation of 2'-Deoxyadenosine-5'-O-(1-Thiotriphosphate) (NA006) by Human Cancer Telomerase.

NA006, a dATP analog having a P=S bond rather than the P=O bond at the a phosphate group will replace dATP and become incorporated into telomeric ladders. Using the conventional telomerase assay, NA006 was shown to be incorporated at the concentrations tested (0.125–2 mM).

C. Incorporation of 2',3'-dideoxyadenosine-5'-Triphosphate (NA007) by Human Cancer Telomerase Using the conventional telomerase assay NA007, a dATP analog lacking the 3'-OH group, showed no apparent NA007 incorporation was detected at the concentrations tested (0.125–2 mM).

D. Incorporation of 2'-Deoxyguanosine-5'-O-(1-Thiotriphosphate) (NA013) by Human Cancer Telomerase NA013, a dGTP analog having a P=S bond rather than the P=O bond at the a phosphate group replaced dGTP and was incorporated into telomeric ladders. Using the modified telomerase assay, NA013 was shown to be incorporated at concentrations of 0.5–2 mM.

E. Incorporation of 2'-Deoxyguanosine-5'-β,γ-methylene triphosphate (NA014) by Human Cancer Telomerase.

NA014, a dGTP analog with a 5'-β,γ-methylene group, replaced dGTP and became incorporated into telomeric ladders. Despite the weak activity, using the modified telomerase assay, NA014 incorporated into telomere could be detected at concentrations of 0.5–2 mM.

F. Lack of Incorporation of 2',3'-dideoxyguanosine-5'-Triphosphate (NA020) by Human Cancer Telomerase.

NA020, a dGTP analog lacking the 3'-OH group, once incorporated into telomere was shown to chain-terminate the reaction. Using the modified telomerase assay, no apparent NA020 incorporation was detected at all concentrations tested (0.125–2 mM).

G. Incorporation of 7-Deaza-2'-deoxyadenosine-5'-triphosphate (NA023) by Human Cancer Telomerase dATP was replaced by 7-deaza-dATP (NA023) with 1 mM TTP and 1.56 μM [α-$^{32}$P]dGTP in the conventional telomerase assay). The products were sensitive to RNase A and processivity decreased with increasing 7-deaza-dATP concentrations. No telomerase activity was detected at >1.5 mM 7-deaza-dATP. However, the level of telomerase activity remained unchanged with 0.25–2 mM dATP as a substrate. The presence of 7-deaza-dATP did not result in a change in pause sites compared to the reactions in the presence of dATP.

H. Incorporation of 7-Deaza-2'-deoxyguanosine-5'-triphosphate (NA022) by Human Cancer Telomerase Replacing dGTP with 7-deaza-dGTP (NA022) in a modified telomerase reaction containing 1 mM dTTP and 3.12 μM [α-$^{32}$P]dATP resulted in formation of radiolabeled products that were sensitive to RNase A. This reaction was distinguished from a reaction with the native dGTP. First, the total amount of products produced by 7-deaza-dGTP was much less than that produced with dGTP. Second, telomerase appeared to be less processive with 7-deaza-dGTP. As the concentration of 7-deaza-dGTP increased, the products became increasingly shorter and the total amount of products decreased until there was no activity at >1.5 mM 7-deaza-dGTP. There was no significant change in activity when dGTP is used as a substrate in the reaction with concentrations varying from 0.25–2 mM. Finally, telomerase paused at significantly more sites in the presence of 7-deaza-dGTP. At a concentration of 0.5 mM 7-deaza-dGTP, there was such a large number of bands pertaining to various pause sites that a predominant pause site could not be determined. When the 7-deaza-dGTP concentration is 0.75–1 mM, a repeated triplet of pause sites was distinguishable.

EXAMPLE 6

Growth Inhibitory Activity of Selected Nucleoside Analogs

Examples 1–4 demonstrated various dTTP, dATP, and dGTP analogs useful for modulating human tumor telomerase activity either by inhibiting the enzyme activity or by incorporating into telomere and as the result of incorporation affecting subsequent telomere elongation. The following examples demonstrate that these compounds have growth inhibitory activity.

To demonstrate the growth inhibitory activity, one cannot simply incubate the cells with the phosphates (mono-, di-, or triphosphates) and expect them to transport into the cells and provide the cells with the triphosphates of nucleoside analogs. The phosphates are highly negatively charged, and therefore do not effectively transport into cells. This is due to the extracellular dephosphorylation of the mono-, di-, or triphosphates by alkaline phosphorylase or 5'-nucleotidase back to the nucleoside. With this in mind, the inventors used only nucleosides rather than nucleoside triphosphates in these studies. Cultured tumor cells were incubated with selected nucleosides at graded concentrations for 6 days and the growth inhibition was determined by the standard MTT assay.

Growth Inhibition of 7-deaza Nucleoside Compounds Against Cancer Cell Lines

Table 4A shows the growth inhibition of the indicated 7-deaza-2'-deoxynucleoside compounds against several cancer cell lines.

TABLE 4A

In Vitro Evaluation of Selected 7-Deazanucleoside Compounds

| Compound | MCF-7 | MDA-231 | BT-20 | DU145 | PC3 | SKBR3 | Raji |
|---|---|---|---|---|---|---|---|
| 1-methyl-7-deaza-2'-deoxyguanosine | 57.52 | >50 | 60.27 | >50 | 93.43 | Not Tested | 43.42 |
| 6-methoxy-7-deaza-2'-deoxyguanosine | 36.11 | 77.25 | 294.59 | >50 | >50 | Not Tested | 37.11 |
| 6-thio-7-deaza-2'-deoxyguanosine | 107.82 | 116.74 | 83.97 | >100 | 209.23 | 108.07 | 102.95 |
| 6-thiomethyl-7-deaza-2'-deoxyguanosine | 88.6 | 281.44 | 94.32 | >100 | >100 | 74.03 | 84.08 |
| 6-thio-7-deaza guanine | 84.25 | >50 | 258.14 | >100 | 119.53 | 74.03 | 84.08 |

A. Growth Inhibition of Selected 7-Deaza-2'-deoxynucleoside against Transformed Embryonic Kidney 293 Cells.

The following table shows the growth inhibition of the indicated 7-deaza-2'-deoxynucleoside compounds against transformed human embryonic kidney cells.

TABLE 5

| Code No. | Chemical Name | IC50 ($\mu$M) |
|---|---|---|
| FS004 | 7-Iodo-7-Deaza-2'-Deoxyadenosine | 0.319 |
| FS015 | 7-Iodo-7-Deaza-8-Aza-2'-Deoxyadenosine | 1.884 |
| FS018 | 7-Bromo-7-Deaza-2'-Deoxyadenosine | 1.144 |
| FS017 | 7-Chloro-7-Deaza-2'-Deoxyadenosine | 3.319 |
| FS005 | 7-Cyano-7-Deaza-2'-Deoxyadenosine | 18.162 |
| FS024 | 7-Methyl-7-Deaza-2'-Deoxyadenosine | 108.555 |
| NA024 | 7-Deaza-2'-Deoxyadenosine | 533.320 |
| FS021 | 7-Iodo-7-Deaza-2'-Deoxyguanosine | 63.445 |
| FS020 | 7-Bromo-7-Deaza-2'-Deoxyguanosine | 180.320 |
| FS019 | 7-Chloro-7-Deaza-2'-Deoxyguanosine | 236.706 |
| FS022 | 7-Methyl-7-Deaza-2'-Deoxyguanosine | 488.850 |
| NA025 | 7-Deaza-2'-Deoxyguanosine | 130.220 |
| NA027 | 1-Methyl-6-Thio-7-Deaza-2'-Deoxyguanosine | 161.000 |
| NA028 | 6-Thio-7-Deaza-2'-Deoxyguanosine | 461.000 |

B. Growth Inhibition of Selected 7-Deaza-2'-deoxynucleoside against Human Colon Carcinoma HT29 Cells.

The following table shows growth inhibition of the indicated 7-deaza-2'-deoxynucleoside compounds against human colon carcinoma cells.

TABLE 6

| Code No. | Chemical Name | IC50 ($\mu$M) |
|---|---|---|
| FS004 | 7-Iodo-7-Deaza-2'-Deoxyadenosine | 1.879 |
| FS015 | 7-Iodo-7-Deaza-8-Aza-2'-Deoxyadenosine | 8.090 |
| FS018 | 7-Bromo-7-Deaza-2'-Deoxyadenosine | 0.963 |
| FS017 | 7-Chloro-7-Deaza-2'-Deoxyadenosine | 15.589 |
| FS005 | 7-Cyano-7-Deaza-2'-Deoxyadenosine | 51.230 |
| FS024 | 7-Methyl-7-Deaza-2'-Deoxyadenosine | 99.620 |
| NA024 | 7-Deaza-2'-Deoxyadenosine | 146.490 |
| FS021 | 7-Iodo-7-Deaza-2'-Deoxyguanosine | 78.755 |
| FS020 | 7-Bromo-7-Deaza-2'-Deoxyguanosine | 170.310 |
| FS019 | 7-Chloro-7-Deaza-2'-Deoxyguanosine | 108.540 |
| FS022 | 7-Methyl-7-Deaza-2'-Deoxyguanosine | 195.540 |
| NA025 | 7-Deaza-2'-Deoxyguanosine | 101.930 |
| NA027 | 1-Methyl-6-Thio-7-Deaza-2'-Deoxyguanosine | 309.500 |
| NA028 | 6-Thio-7-Deaza-2'-Deoxyguanosine | 461.100 |

EXAMPLE 7

Effect of AZT on Cells.

A reasonable outcome of incubating tumor cells with appropriate 2'deoxynucleosides is the formation of the corresponding 2'deoxynucleoside triphosphate intracellularly. If 2'-deoxynucleoside triphosphates inhibit intracellular telomerase, one would expect the gradually shortening the telomere length with the formation of dicentric chromosome. Example 6 provided evidence to demonstrate these effects using AZT as the model agent.

A. AZT Induces Telomere Shortening

Figure 11:
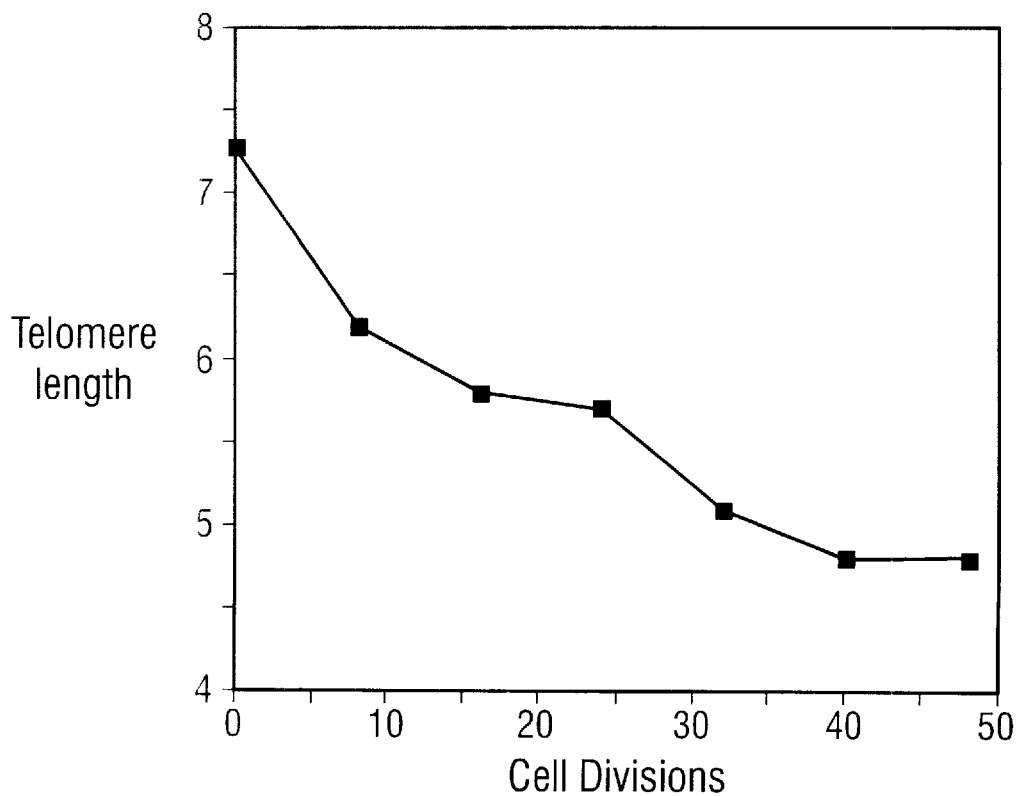
FIG. 11 shows that AZT induces telomere shortening. HeLa cells were incubated and grown with 800 $\mu$M of AZT and telomeres were measured by digesting the chromosomal ends with MSEI. The telomeric fragments were separated by electrophoresis, probed for telomeric sequence and the average size of the signals produced was determined by autoradiography and densitometry. The decrease in telomer length is graphed relative to the number of cell divisions.

HeLa cells were incubated and grown with 800 $\mu$M of AZT. The amount of AZTTP produced within the cell was expected to inhibit telomerase. Telomeres were measured by digesting the chromosomal ends with MSEI. The telomeric fragments were separated by electrophoresis, probed for telomeric sequence and the average size of the signals produced was determined by autoradiography and densitometry. Without telomerase activity, the HeLa cells can no longer maintain their telomeres and therefore the telomeres shorten with each generation. The decrease in telomer length with cell divisions is shown in FIG. 11.

B. AZT Induces Telomere Fusion and Chromosome Instability in CHO Cells

Figure 12:
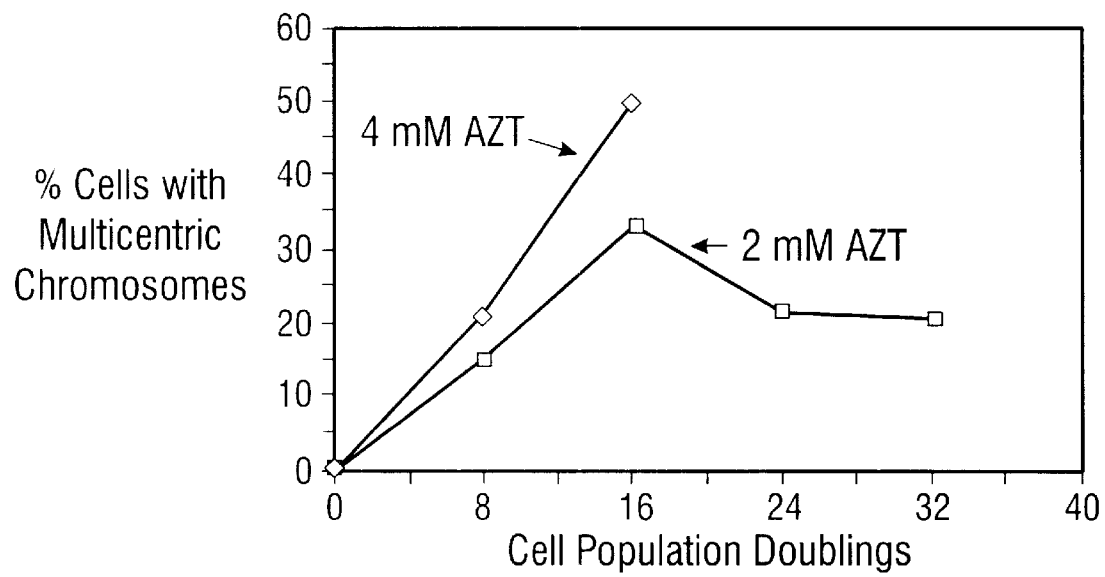
FIG. 12 shows that AZT induces telomere fusion and chromosome instability in CHO cells. CHO cells were incubated and grown with 2 and 4 mM AZT. Cytogenetic analysis was performed on the chromosomes and the number of chromosome end fusions was determined. AZT induced a AZT concentration dependent and cell doubling dependent destabilization of the chromosomes by inhibition of telomerase.

Chinese hamster ovary cells were incubated and grown with 2 and 4 mM AZT. Cytogenetic analysis was performed on the chromosomes and the number of chromosome end fusions was determined. AZT induced a AZT concentration dependent and cell doubling dependent destabilization of the chromosomes by inhibition of telomerase as illustrated in FIG. 12.

E. AZT Induces Delayed Cell Death in CHO Cells

Figure 13:
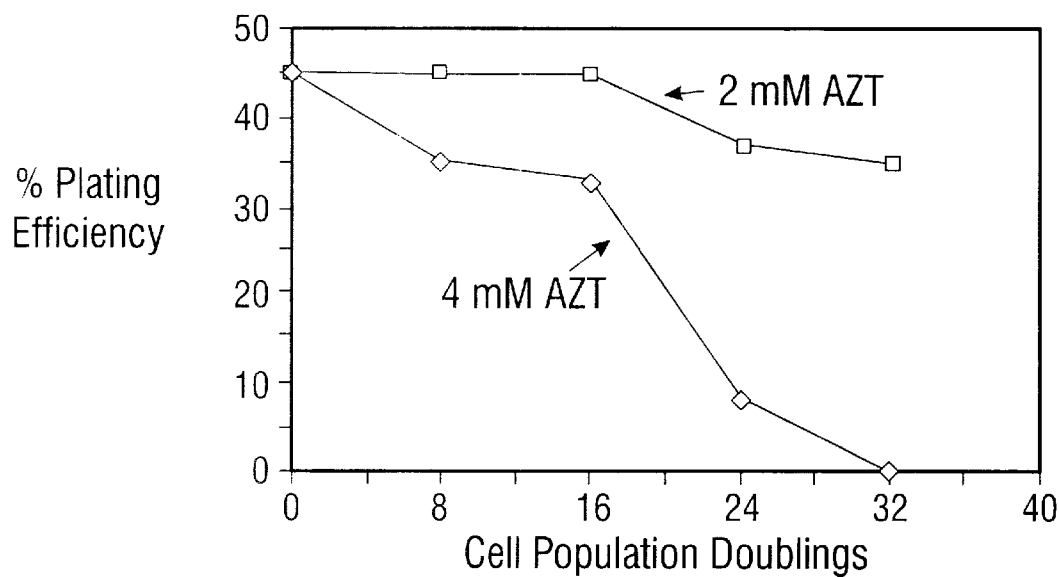
FIG. 13 shows that AZT induces delayed cell death in CHO cells CHO cells were incubated and grown with 2 and 4 mM AZT. The cell viability was determined by the cells' ability to form colonies. After 16 cell doublings, the cells began to die in both 2 and 4 mM AZT. Eventually all cells died in 4 mM AZT.

Chinese hamster ovary cells were incubated and grown with 2 and 4 mM AZT. The cell viability was determined by the cells' ability to form colonies. Initially, there was little effect on viability, but after 16 cell doublings, the cells began to die in both 2 and 4 mM AZT. Eventually all cells died in 4 mM AZT. Cell death appears to result from massive chromosome instability due to the inhibition telomerase. Results are illustrated in FIG. 13.

EXAMPLE 8

Preparation of 7-deaza-1-methyl-6-thio-2'-deoxyguaosine

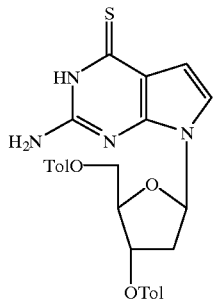

1

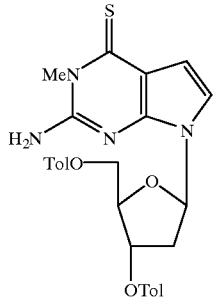

2

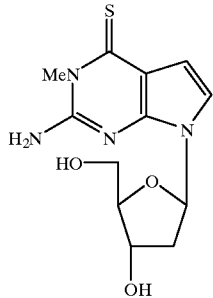

3

1-methyl-2-amino-7-[2'deoxy-3,5-di-O-(p-toluoyl)-
$\beta$-D-erythro-pentofuranose]-7H-pyrrolo[2,3-d]
pyrimidine-4-(3H)-thione(2).

To a cooled solution (0°C., 1 ml DMF) of 1 [Seela, et al (1987)](300 mg, 0.578 mmol) was added NaH (60% in oil, 25.5 mg, 0.636 mmol). This was allowed to stir for 1 hr at 0° C. Dimethyl sulfate (73.0 mg, 54.7 $\mu$l, 0.578 mmol) was added to the solution at 0° C. The reaction was stirred for 1 hr and quenched using sat. NH$_4$Cl. The beige solid was filtered and compound 2 was purified by flash silica gel chromatography (methanol:chloroform 0→5% methanol) to give a white solid (221 mg, 72% yield). R=0.60 (methanol:chloroform 5:95)

1-methyl-2-amino-7-[2'deoxy-β-D-erythro-pentofuranose]-7H-pyrrolo [2,3d]pyrimidine-4-(3H)-thione (NA027).

A solution of 2 (180 mg, 0.338 mmol) in 13 ml of 0.1 N sodium methoxide in methanol was stirred at room temperature for 3 hr. The reaction was neutralized with 6 N HCl and evaporated to dryness. The compound, 3, was purified by flash silica gel chromatography (methanol:chloroform 0→10% methanol) to give a white solid (72 mg, 72% yield). $R_f$-0.27 (methanol:chloroform 10:90). $^1$H-NMR (DMSO-d$_6$) 7.22 (d, 1H, J=6 Hz), 6.59 (s, 2H, NH$_2$), 6.40 (d, 1H, J=6 Hz), 6.32 (dd, 1H, J=6 Hz and 8 Hz, H-1'), 4.30 (m, 1H, H-3'), 3.78 (m, 1H, H-4'), 3.49 (m, 2H, H-5'), 2.60 (s, 3H, CH$_3$N), 2.35 and 2.12 (m, 2H, H-2').

EXAMPLE 9

A general procedure for the synthesis of 7-substituted 7-deaza-dGTP α-phosphorothionates is illustrated in the scheme below. dGTP is shown in the scheme but it is equally applicable to the preparation of dATP analogs.

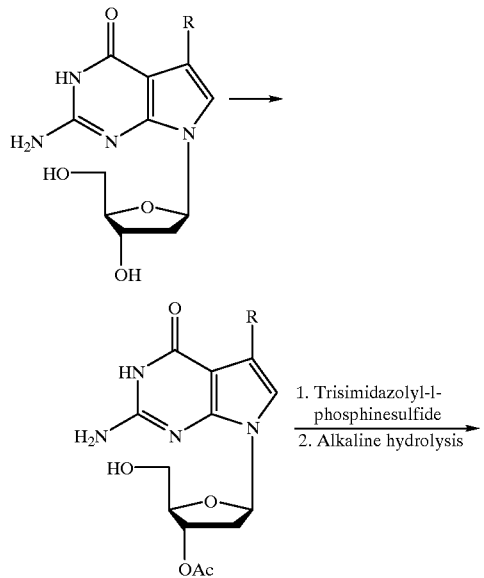

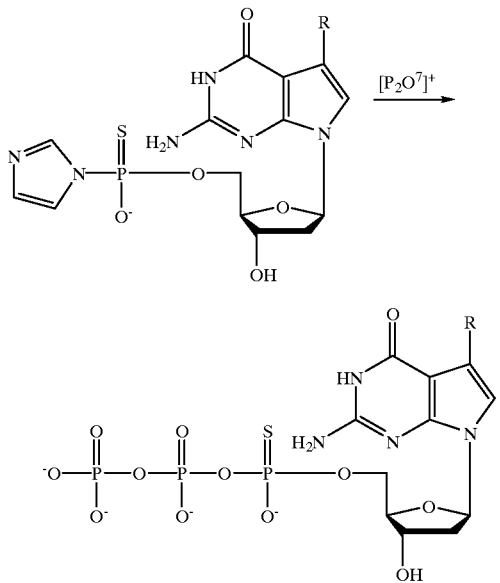

[R = H, CH$_3$, C$_2$H$_5$, F, Cl, Br, I]

EXAMPLE 10

Destabilization of the ability of human DNA to adopt a G-quartet structure as a result of incorporation of selected 7-deazapurine-2'-deoxyribonucleotides into human telomeric DNA.

The incorporation of 7-deaza-2'-deoxyguanosine into an oligodeoxyribonucleotide of the sequence d(GGTTAGG*GTTAG) where G* represents the 7-deaza-2'-deoxyguanosine residue results in the inability of this sequence to form G-quartet structure in Kcl-containing buffers at temperatures above about 20° C., as evidenced by the lack of imino proton resonances in the region of 10–12 ppm in the NMR spectrum of this sample. In comparison, the corresponding natural sequence d(GGTTAGGGTTAG) forms G-quartet structures at temperatures as high as 70° C., as evidence by the imino proton resonances at 10–12 ppm observed in the NMR spectrum of this DNA.

| | | Inhibition of 293 Telomerase | | |
|---|---|---|---|---|
| | | Conventional Assay *dGTP | Modified Assay *dATP | Substrate of 293 Telomerase |
| NA004 | 2'-Deoxyadenosine-5'-β,γ-Methylene Triphosphate | No Inhibition (Up to 2 mM) | | Replace dATP Is a substrate No substrate inhibition |

Inhibition of 293 Telomerase

| | Conventional Assay *dGTP | Modified Assay *dATP | Substrate of 293 Telomerase |
|---|---|---|---|
| NA006 2'-Deoxyadenosine-5'-O-(1-Thio-Triphosphate) | No Inhibition (up to 2 mM) | | Is a substrate<br>No substrate inhibition |
| NA007 2',3'-Dideoxyadenosine-5'-Triphosphate | No Inhibition (up to 2 mM) | | No product formed using (TTAGGG)3 primer |
| NA023 7-Deaza-2'-Deoxyadenosine-5'-Triphosphate | (IC50 = 59 μM) | Yes (IC50 = 8 μM) | Is a substrate<br>Produces short telomere<br>Substrate Inhibition |
| NA011 Guanosine-5'-β,γ-Methylene Triphosphate | No Inhibition (up to 2 mM) | | |

-continued

| | Inhibition of 293 Telomerase | | |
|---|---|---|---|
| | Conventional Assay *dGTP | Modified Assay *dATP | Substrate of 293 Telomerase |

NA014  2'-Deoxyguanosine-5'-β,γ-Methylene Triphosphate  (IC50 < 0.125 mM)

NA013  2'-Deoxyguanosine-5'-O-(1-Thio-Triphosphate)  (IC50 < 0.125 mM)

NA015  2'-Deoxyguanosine-5'-Phosphorothioate  No Inhibition (up to 2 mM)

-continued

| | | Conventional Assay *dGTP | Modified Assay *dATP | Substrate of 293 Telomerase |
|---|---|---|---|---|
| NA020 | 2',3'-Dideoxyguanosine-5'-Triphosphate | IC50 < 125 μM | | |
| NA022 | 7-Deaza-2'-Deoxyguanosine-5'-Triphosphate | Yes (IC50 = 11 μM) | Yes (IC50 = 56 μM) | Is a substrate Produces short telomere Substrate Inhibition |
| NA001 | 2',3'-Dideoxythymidine-5'-Triphosphate | | | |

Inhibition of 293 Telomerase

-continued

Inhibition of 293 Telomerase

| | Conventional Assay *dGTP | Modified Assay *dATP | Substrate of 293 Telomerase |
|---|---|---|---|

NA002  3'-Fluoro-3'-Deoxythymidine-5'-Triphosphate

NA005  3'-Amino-3'-Deoxythymidine-5'-Triphosphate

NA010  3'-Azido-3'-Deoxythymidine-5'-Triphosphate

NA021  5-Allylamino-2'-Deoxyuridine-5'-Triphosphate    the telomerase activity is weak)

EXAMPLE 12

This example describes the synthesis of 7-deaza deoxyguanosine compounds that have shown inhibition activity against human cancers cells. Structures of intermediates employed in the synthesis of compounds 3 and 5 are set forth.

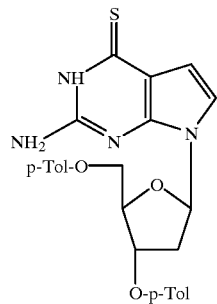
1
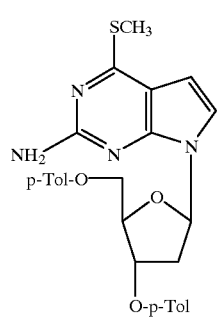
2
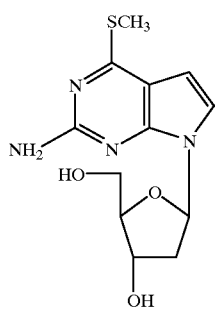
3
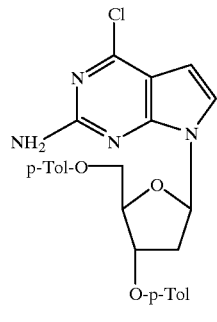
4
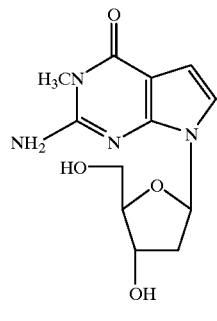
5
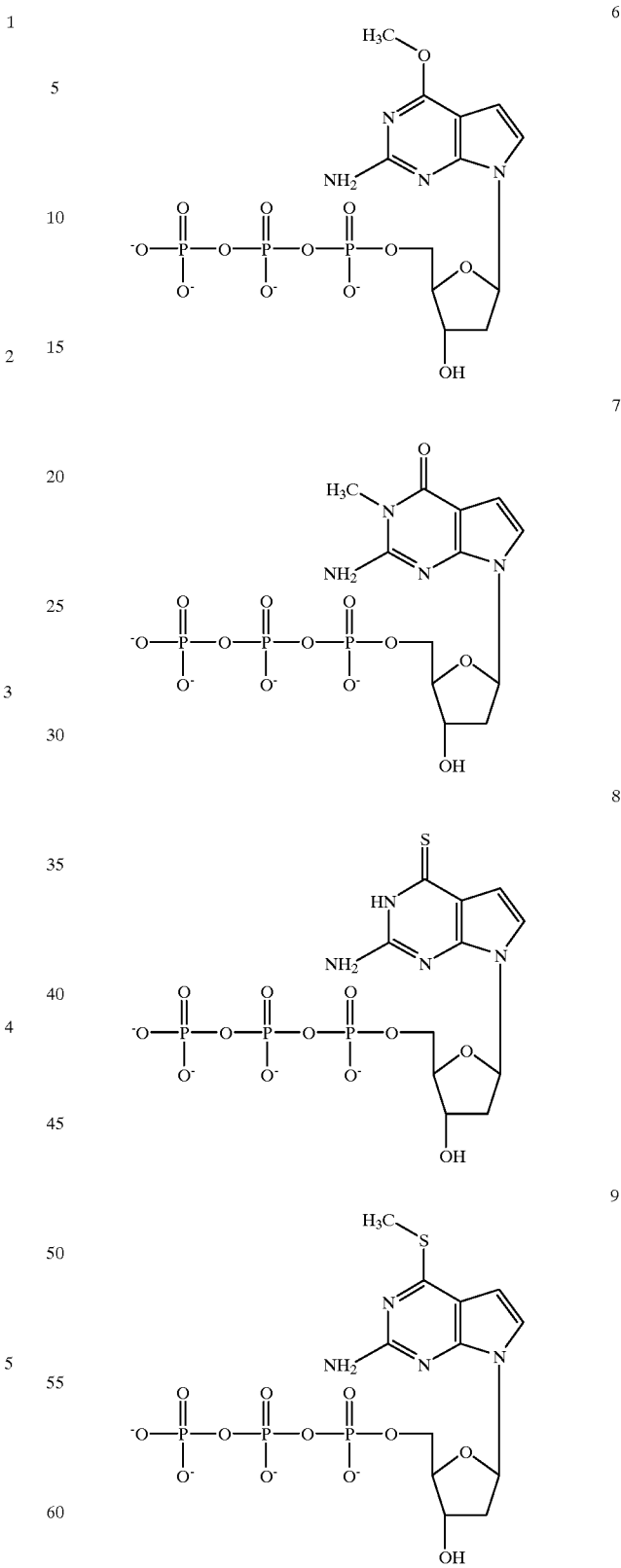
6-thiomethyl-7-deaza-2'-deoxyguanosine (3)
To a cooled solution (0° C.,1 ml DMF) of 1 (300 mg, 0.578 mmole) was added NaH (60% in oil, 25.5 mg, 0.636 mmole). This was allowed to stir for 1 hr at 0° C. Dimethyl sulfate (73.0 mg, 54.7 ml, 0.578 mmole) was added and the reaction mixture was allowed to stir for an additional hour. The reaction was quenched using sat. $NH_4Cl$ (aq) and the beige solid filtered. The product was purified by flash silica gel chromatography (methanol:chloroform, 0→5% methanol) to give (2) a white solid (221 mg, 72% yield) $R_f$–0.27 (chloroform:methanol, 95:5). A solution of 2 (180 mg, 0.338 mmole) in 13 ml of 0.1 N sodium methoxide in methanol was stirred at room temperature for 3 hr. The reaction was neutralized with 6 M HCl and evaporated to dryness. The compound 3 was purified by flash silica gel chromatography (methanol:chloroform, 0→10% methanol) to give an amorphous solid (72 mg, 72% yield) $R_f$–0.27 (chloroform:methanol, 90:10). NMR data are shown in Tables 13, 14 and 15.

TABLE 13

$^1$H NMR data 7-deaza purine nucleosides in DMSO-$d_6$ and nucleotides in $D_2O$

| Compound | H(7,8) | Other |
|---|---|---|
| 3 | 7.22 (d, 1H), 6.40 (d, 1H), $J_{H-H}$ = 6 Hz | S6-CH$_3$ 2.60 (s, 3H) |
| 5 | 6.90 (d, 1H), 6.27 (d, 1H), $J_{H-H}$ = 4 Hz | N1-CH$_3$ 3.31 (s, 3H) |
| 6 | 6.98 (d, 1H), 6.19 (d, 1H), $J_{H-H}$ = 4 Hz | O6-CH$_3$ 3.77 (s, 3H) |
| 7 | 6.91 (d, 1H), 6.26 (d, 1H), $J_{H-H}$ = 4 Hz | N1-CH$_3$ 3.27 (s, 3H) |

TABLE 13-continued $^1$H NMR data 7-deaza purine nucleosides in DMSO-$d_6$ and nucleotides in $D_2O$

| Compound | H(7,8) | | Other |
|---|---|---|---|
| 8 | 7.09 (d, 1H), 6.41 (d, 1H), $J_{H-H}$ = 3.5 Hz | | NA |
| 9 | 7.24 (d, 1H), 6.42 (d, 1H), $J_{H-H}$ = 4 Hz | | S6-CH$_3$ 2.54 (s, 3H) |

| Compound | H1' | H2'a & b | H3' | H4' | H5' |
|---|---|---|---|---|---|
| 3 | 6.32 (dd, 1H) $J_{H-H}$ = 2.35, 2.12 5,8 Hz | (m, 2H) | 4.30 (m, 1H) | 3.78 (m, 1H) | 3.49 (m, 2H) |
| 5 | 6.42 (dd, 1H) $J_{H-H}$ = 2.55, 2.26 4,8 Hz | (m, 2H) | 4.62 (m, 1H) | 4.08 (m, 1H) | 4.03 (m, 2H) |
| 6 | 6.25 (dd, 1H) $J_{H-H}$ = 2.50, 2.23 4,8 Hz | (m, 2H) | 4.47 (m, 1H) | 4.01 (m, 1H) | 3.77 (m, 2H) |
| 7 | 6.27 (dd, 1H) $J_{H-H}$ = 2.33, 2.06 5,8 Hz | (m, 2H) | 4.26 (m, 1H) | 3.75 (m, 1H) | 3.53 (m, 2H) |
| 8 | 6.24 (dd, 1H) $J_{H-H}$ = 2.49, 2.26 4,8 Hz | (m, 2H) | 4.48 (m, 1H) | 4.01 (m, 1H) | 3.82 (m, 2H) |
| 9 | 6.46 (dd, 1H) $J_{H-H}$ = 2.66, 2.40 4,8 Hz | (m, 2H) | 4.70 (m, 1H) | 4.16 (m, 1H) | 4.10 (m, 2H) |

Chemical shifts all given ppm relative to TMS or TSP.

TABLE 14

$^{13}$C NMR data 7-deaza purine nucleosides n DMSO-$d_6$ and nucleotides in $D_2O$

| Compound | C2 | C4 | C5 | C6 | C7 | C8 | Other |
|---|---|---|---|---|---|---|---|
| 3 | 158.04 | 153.44 | 99.37 | 165.52 | 102.98 | 116.59 | S6-CH3 35.93 |
| 5 | 153.26 | 148.81 | 99.10 | 158.08 | 102.43 | 116.89 | N1-CH3 27.76 |
| 6 | 159.88 | 154.11 | 99.28 | 164.49 | 101.23 | 120.80 | O6-CH3 54.78 |
| 7 | 154.11 | 149.93 | 101.26 | 161.28 | 103.58 | 119.43 | N1-CH3 29.11 |
| 8 | 153.01 | 148.52 | 105.44 | 173.62 | 114.84 | 122.87 | NA |
| 9 | 160.02 | 154.33 | 98.53 | 164.59 | 101.30 | 120.98 | S6-CH3 42.89 |

| Compound | C1' | C2' | C3' | C4' | C5' |
|---|---|---|---|---|---|
| 3 | 82.39 | 39.37 | 72.35 | 80.40 | 64.37 |
| 5 | 86.90 | 39.52 | 71.04 | 81.9 | 62.07 |
| 6 | 83.51 | 39.11 | 72.50 | 85.87 JC-P = 8.1 Hz | 65.44 JC-P = 4.5 Hz |
| 7 | 83.62 | 37.52 | 80.52 | 84.06 JC-P = 8.9 Hz | 65.36 JC-P = ? Hz |
| 8 | 86.00 | 39.16 | 72.43 | 86.06 JC-P = 8.0 Hz | 65.40 JC-P = 4.4 Hz |
| 9 | 83.34 | 39.05 | 72.47 | 85.82 JC-P = 8.1 Hz | 65.58 JC-P = 4.5 Hz |

Chemical shifts all given ppm relative to TMS or TSP.

TABLE 15

$^{31}$P NMR data 7-deaza purine nucleotides in D$_2$O

| Compound | Monophosphate | Triphosphate a | Triphosphate b | Triphosphate g |
|---|---|---|---|---|
| 6 | 2.24 | −8.18 JP-P = 6 Hz | −10.61 JP-P = 6 Hz | −22.24 JP-P = 6 Hz |
| 7 | 4.64 | −9.36 JP-P = 6 Hz | −10.48 JP-P = 6 Hz | −22.19 JP-P = 6 Hz |
| 8 | 2.20 | −8.59 JP-P = 6 Hz | −10.62 JP-P = 6 Hz | −22.31 JP-P = 6 Hz |
| 9 | 1.75 | −9.85 JP-P = 6 Hz | −10.65 JP-P = 6 Hz | −22.54 JP-P = 6 Hz |

Chemical shifts all given ppm relative to phosphoric acid

1-N-methyl-7-deaza-2'-deoxyguanosine (5)

Compound 4 (332 mg, 0.637 mmole) was refluxed in 2 M NaOH (2.0 ml, 4 mmole) for 4 hr. The solution was cooled to room temperature and dimethyl sulfate (401.9 mg, 301.5 ml, 3.186 mmole) was added and the reaction was stirred for an additional 2 hr. The solvent was evaporated in vacuo and the residue was treated with methanol and silica gel. The methanol was removed and chloroform was added to the silica gel. The chloroform mixture was added to a flash silica gel chromatography column and washed with chloroform. The product 5 was eluted with chloroform:methanol (90:10) to give a white solid (107 mg, 60% yield). Further elution with chloroform:methanol (90:10) gave a second product which was determined to be 7-deaza-2'-deoxyguanosine (68 mg, 40% yield). NMR data shown in Tables 13, 14 and 15.

General Procedure: 7-deaza-2'-deoxy nucleoside-5'-triphosphates

The unprotected nucleosides (150–250 mmole) were treated, at 0° C., with phosphorus oxychloride and water (1:2:1 equivalence of nucleoside:POCl$_3$:water) in trimethyl phosphate (1–3 ml). The reactions were stirred at 0° C. for 1 to 4 hr. The reactions were quenched by the addition of 1 M aqueous trimethylammonium bicarbonate and the solvent evaporated in vacuo. The residue taken up in water and applied to an ion-exchange column (DEAE-Sephadex A-25, HCO$_3^-$form). The column was then washed with water (about 500 ml) and a linear gradient applied from 0 to 0.5 M triethylammonium bicarbonate over 500 ml. A UV detector (254 nm) was used to identify those fractions containing the nucleoside monophosphate. The fractions containing the product were evaporated in vacuo. The residual triethylammonium bicarbonate was removed by evaporation with ethanol several times. The yields ranged from 78–140 mmole or roughly 52 to 73%.

The nucleoside monophosphates were converted to the triphosphates using the following procedure. The nucleoside monophosphate (70–130 mmole) was dissolved in water and applied to a cation-exchange column (Merck, pyridinium form). The column was washed with water and tributylamine (1 eq) was added to the eluate. The solvent was removed and residual water was removed by repeated evaporations with DMF. The residue was then dissolved in anhydrous DMF (1–2 ml) and 1,1'-carbonyldiimidazole (5 eq) in DMF (1 ml) was added. The reaction was allowed to stir overnight at room temperature. The excess 1,1'-carbonyldiimidazole was quenched with methanol (8 eq) and the solution treated with bis-triethylammonium pyrophosphate (5 eq) dissolved in DMF. The reaction was allowed to stir again overnight at room temperature. The reaction was evaporated and applied to an ion-exchange column (DEAE-Sephadex A-25, HCO$_3^-$form) and washed with water (500 ml). The triphosphates were eluted with a linear gradient, 0 to 0.5 M triethylammonium bicarbonate over 1000 ml. A UV detector (254 nm) was used to isolate the nucleoside triphosphate. The fractions containing the product were evaporated in vacuo. The residual triethylammonium bicarbonate was removed by evaporation with ethanol several times. The yields ranged from 43–87 mmole or roughly 58 to 67%.

6-methoxy-7-deaza-2'-deoxyguanosine triphosphate (6)

This compound (6) was prepared starting with 187 mmole of unprotected nucleoside and yielding 72 mmole (40% overall). NMR data shown on Tables 13, 14 and 15. Compound 6 inhibited HeLa cell telomerase in a concentration dependent manner, shown in FIG. 1. The IC$_{50}$ was 4.9 µM.

1-methyl-7-deaza-2'-deoxyguanosine triphosphate (7)

Figure 2:
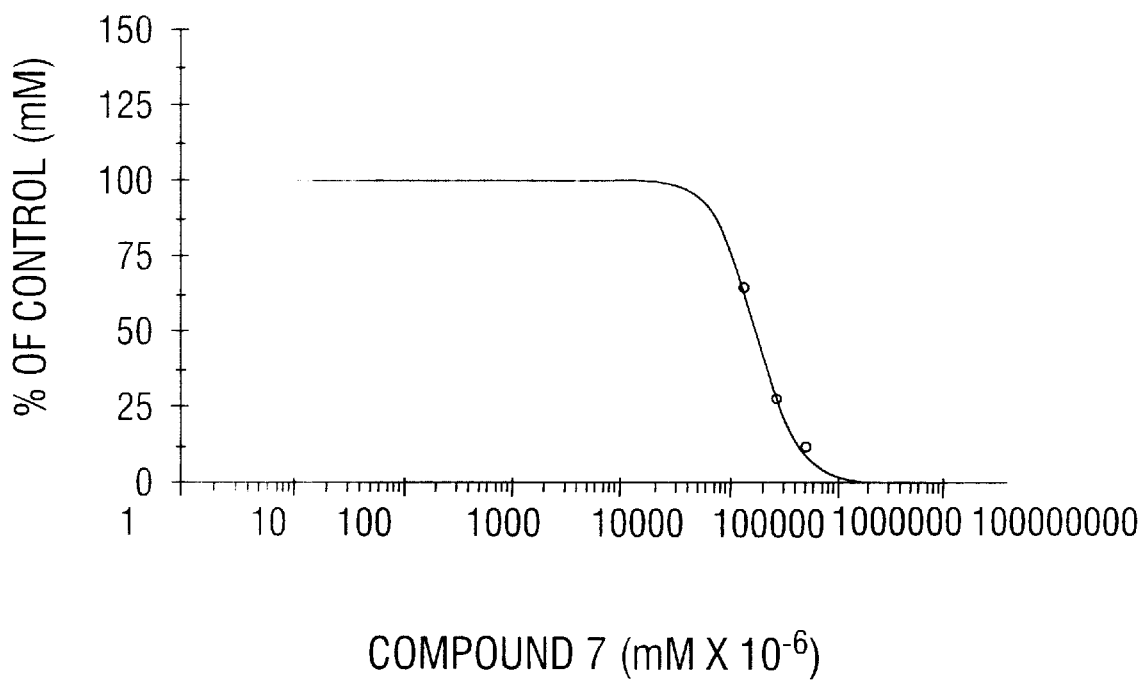
FIG. 2. shows inhibition of human cancer HeLa cell telomerase activity by 1-methyl-7-deaza-2'-deoxyguanosine. The inhibition is concentration dependent with an $IC_{50}$ of 159 $\mu$M.

This compound (7) was prepared starting with 210 mmole of unprotected nucleoside and yielding 92 mmole (44% overall). NMR data shown on Tables 13, 14 and 15. Compound 7 inhibited HeLa cell telomerase in a concentration dependent manner, shown in FIG. 2. The IC$_{50}$ was 159 µM.

6-thio-7-deaza-2'-deoxyguanosine triphosphate (8)

This compound (8) was prepared starting with 172 mmole of unprotected nucleoside and yielding 78 mmole (45% overall). NMR data shown in Tables 13, 14 and 15.

6-thiomethyl-7-deaza-2'-deoxyguanosine triphosphate (9)

This compound (9) was prepared starting with 204 mmole of unprotected nucleoside and yielding 105 mmole (51% overall). NMR data shown in Tables 1,2 and 3. Compound 9 exhibited no inhibition in a HeLa cell telomerase assay up to a concentration of 62.5 µM.

EXAMPLE 13

This example illustrates that nucleoside triphosphate analogs can replace native nucleotides (dTTp, dATP, dGTP). In some cases, incorporation of the nucleotide analogs leads to a prematurely shortened telomere. Replacing dGTP by modified dGTP analogs (G*) such as 6-methoxy-7-deaza-dGTP (Compound 6, 0.125–2 mM, left hand lanes) or 6-thio-7deaza-dGTP (Compound 8, 0.125–2 mM, right hand lanes, FIG. 3) in a modified telomerase reaction containing 1 mM dTTP and 3.12 µM [α-$^{32}$P]dATP results in the formation of radiolabeled products that are different from those produced in the presence of dGTP (1 mM, far left-hand lane, FIG. 3). In the presence of dGTP, the telomerase products correspond to addition of two nucleotides to the primer [i.e. (TTAGGG)$_3$TT] in addition higher molecular weight products. This pausing pattern changes to reflect incorporation of three [(TTAGGG)$_3$TTA] and four [TTAGGG)$_3$TTAG] nucleotides, indicating incorporation of Compound 7 and Compound 8 into the telomerase product. The lack of longer products in reactions run in the presence of Compounds 7 and 8 indicates that after incorporation of Compound 7 or Compound 8, there is little extension of the telomerase product.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following literature citations as well as those cited above are incorporated in pertinent part by reference herein for the reasons cited in the above text:

Allshire et al., "Telomeric repeat from *T. thermophila* cross hybridizes with human telomeres," *Nature* (London), 332:656–659, 1988.

Allsopp, R. C., Vaziri, H., Patterson, C., Goldstein, S., Youiglai, E., Futcher, A. B., Greider, C. W., and Harley, C. B, "Telomere length predicts replicative capacity of human fibroblasts," *Proc. Natl. Acad, Sci. USA*, 89:10114–10118, 1992.

Bahler, J., Hagens, G., Holzinger, G., Scherthan, H., and Heyer, W.-H, *Chromosoma* 103, 129–141, 1994.

Balagutumoorthy, P., and Brahmachari, S. K., *J. Biol. Chem.* 269, 21858–21869, 1994.

Balazsovits et al., "Analysis of the effect of liposome encapsulation on the vesicant properties, acute and cardiac toxicities, and antitumor efficacy of doxorubicin," *Cancer Chemother. Pharmacol.*, 23:81–86, 1989.

Balzarini et al., "Differential patterns of intracellular metabolism of 2',3'-didehydro-2',3'dideoxythymidine and 3'-azido-2',3'-dideoxythymidine, two potent anti-human immunodeficiency virus compounds," *J. Biol. Chem.*, 264:6127–6133, 1989.

Balzarini et al., "The in vitro and in vivo anti-retrovirus activity, and intracellular metabolism of 3'-azido-2',3'-dideoxythymidine and 2',3'-dideoxycytidine are highly dependent on the cell species," *Biochem. Pharmacol.*, 37:897–903, 1988.

Blackburn et al., "Telomerases," *Annu. Rev. Biochem.*, 61:113–29, 1992.

Blackburn, "Structure and function of telomeres," *Nature (London)*, 350:569–573, 1991.

Blackburn, "Telomeres and their synthesis," *Science*, 249:489–490, 1990.

Bohr and Hanawalt, "DNA Repair in Genes," *Pharmac. Ther.*, 38:305–319, 1988.

Chadeneau, C., Hay, K., Hirte, H. W., Gallinger, S., and Bacchetti, S., *Cancer Res.*, 55:2533–2536, 1995.

Chang and Brenner, *Focus*, 6(4):66–69, 1988.

Cohn, M., and Blackburn, E. H., *Science* 269, 396–400, 1995.

Collins, K., and Greider, C. W., *EMBO J.*, 14:5422–5432, 1995.

Cooke and Smith, "Variability at the telomeres of the human X/Y pseudoautosomal region," *Cold Spring Harbor Symp. Quant. Biol.*, 51:213–219, 1986.

Coune et al., 1988.

Counter et al., "Telomere shortening associated with chromosome instability is arrested in immortal cells which express telomerase activity," *EMBO J.*, 11:1921–1929, 1992.

Counter, C. M., Gupta, J., Harley, C. B., Leger, B., and Bacchetti, S., *Blood*, 85:2315–2320, 1995.

Counter, C. M., Hirte, H. W., Bacchetti, S., and Harley, C. B., "Telomerase activity in human ovarian carcinoma," *Proc. Natl. Acad. Sci.*, 91:2900–2904, 1994.

DeLange et al., "Structure and variability of human chromosome ends," *Mol. Cell Biol.*, 10:518–527, 1990.

Diaz, G., and Lewis, K. R., *Chromosoma*, 52:27–35, 1975.

Dixon, M., and Webb, E. C., *Enzymes*, 3rd Edition, New York, N. Y., 1979.

Farquhar et al., 1983.

Feng et al., *Science*, 1995.

Greider and Blackburn, "The telomere terminal transferase of Tetrahymena is a ribonucleoprotein enzyme with two kinds of primer specificity," *Cell*, 51:887–898, 1987.

Greider, C. W. And Blackburn, E. H., *Cell*, 43:405, 1985.

Greider, C. W., and Blackburn, E. H., *Cell*, 51:887–898, 1987.

Guschlbauer, W., Chantot, J. -F., and Thiele, D., *J Biomol. Struct. Dyn.*, 8:491–510, 1990.

Haber and Thorburn, "Healing of broken linear dicentric chromosomes in yeast," *Genetics*, 106:207–226, 1984.

Harley et al., "Telomeres shorten during aging of human fibroblasts," *Nature*, 345:458–460, 1990.

Harley, C. B., *J. NIH Research*, 7:64–68, 1995.

Harley, C. W., *Mutat. Res.*, 256:271, 1991.

Hastie et al., "Telomere reduction in hu man colorectal carcinoma and with aging," *Nature*, 346:866–868, 1990.

Heath et al, "Liposome-mediate delivery of pteridine antifolates to cells in vitro: potency of methotrexate, and its a and y substituents," *Biochem. Biophys. Acta*, 862:72–80, 1986.

Henderson et al, 1990.

Ide et al., "Progress of aging in human diploid cells transformed with a tsA mutant of Simian Virus 40," *Exp. Cell Res.*, 150:321–328, 1984.

Imaizumi et al., "Liposome-entrapped superoxide dismutase ameliorates infarct volume in focal cerebral ischemia," *Acta Neurochurgia Suppl.*, 51:236–239, 1990.

Imaizumi et al., "Liposome-entrapped superoxide dismutase reduces cerebral infarction in cerebral ischemia in rats," *Stroke*, 21:1312–1317, 1990.

Kim, N. W., Piatyszek, M. A., Prowse, K. R., Harley, C. B., West, M. D., Ho, P. L. C., Coviello, G. M., Wright., W. E., Weinrich, S. L., and Shay, J. W., *Science*, 266:2011, 1994.

Klingelhutz et al., "Restoration of telomeres in human papillomavirus-immortalized human anogenital epithelial cells," *Mol. Cell Biol.*, 14:961–969, 1994.

Kruk and Bohr, "DNA damage and repair in telomeres," *Proc. Am. Assoc. Cancer Res.,* 34:3, 1993.

Lindsey et al., "In vivo loss of telomeric repeats with age in humans," *Mutat. Res.,* 256:45–48, 1991.

Liu, Z., and Gilbert, W., *Cell,* 77:083–1092, 1994.

Liu, Z., Lee, A., and Gilbert, W., *Proc. Natl. Acad., Sci. USA,* 92:6002-6006, 1995.

Lopez-Berestein et al., Liposomal amphotericin B for the treatment of systemic fungal infections in patients with cancer: A preliminary study," *J. Infect. Diseases,* 151(4):704–710, 1985.

Mann and Davis, "Instability of dicentric plasmids in yeast," *Proc. Natl. Acad. Sci. USA,* 80:228–232, 1983.

Mantell, L. L. and Greider, C. W., "Telomerase activity in germline and embryonic cells of Xenopus," *EMBO J,* 13:3211–3217, 1994.

McClintock, "The stability of broken ends of chromosome in *Zea mays, Genetics,* 26:234–282, 1941.

McClintock, "The fusion of broken ends of chromosomes following nuclear fusion," *Proc. Natl. Acad. Sci. USA,* 28:458–463, 1942.

McConlogue, L., Brow, M. A. D., and Innis, M. A., *Nucleic Acids Res.,* 16:9869, 1988.

Mizusawa, S., Nishimura, S., and Seela, F., *Nucleic Acids Res.,* 14:1319–1324, 1986.

Mori and Fukatsu, "Anticonvulsant effect of DN-1417, a derivative of thyrotropin-releasing hormone, and liposome entrapped DN-1417, on amygdaloid-kindled rats," *Epilepsia,* 33(6):994–1000, 1992.

Morin G. B., "The human telomere terminal transferase enzyme is a ribonucleoprotein that synthesizes TTAGGG repeats," *Cell,* 59:521–529, 1989.

Muller et al., "Laboratory methods: Efficient transfection and expression of heterologous genes in PC12 cells," *DNA Cell Biol.,* 9(3):221–229, 1990.

Murchie, A. I. H., and Lilley, D. M. J., *EMBO J.,* 13:993–1001, 1994.

Nabel et al., "Gene transfer in vivo with DNA-liposome complexes: lack of autoimmunity and gonadal localizations," *Human Gene Ther.,* 3:649–656, 1992b.

Olovnikov, "A theory of marginotomy," *J Theor Biol,* 41:181–190, 1973.

Pikul et al., "In vitro killing of melanoma by liposome-delivered intracellular irradiation," *Arch. Surg,* 122:1417–1420, 1987.

Prowse, K., Avilion, A. A., and Greider, C. W., "Identification of a nonprocessive telomerase activity from mouse cells," *Proc. Natl. Acad. Sci. USA,* 90:1493–1497, 1993.

Radna et al., "Growth of immortal Simian Virus 40 tsA-transformed human fibroblasts is temperature dependent," *Mol. Cell Biol.,* 9:3093–3096, 1989.

Roth and Wilson, In: *"Genetic Recombination,"* (R. Kucherlapati, G. R. Smith, Eds.), pp. 621–653, New York, AMS Press, 1988.

Sastry et al., 1992.

Scheit, K. H., In: *Nucleotide Analogs Synthesis and Biological Function,* Chapter 4.

Seela, F., and Driller, H., *Nucleic Acids Res.,* 17:901–910, 1989.

Seela, F., and Roling, A., *Nucleic Acids Res.,* 20:55–61, 1991.

Seela, F., and Thomas, H., *Helv. Chim. Acta,* 78:94–108, 1995.

Seela, F., Berg, H., and Rosemeyer, H., *Biochemistry,* 28:6193–6198, 1989.

Seela, F., Steker, H., Driller, H., and Bindig, U., *Liebigs Ann. Chem.,* 15–19, 1987.

Seela, F., Westermann, B., and Bindig, U., *J. Chem. Soc. Perkin Trans. I,* 697–702, 1988.

Sen, S. and Gilbert, W., *Nature,* 334:364–366, 1988.

Shay et al., "E6 of human papillomavirus type 16 can overcome the M1 stage of immortalization in human mammary epithelial cells but not in human fibroblasts," *Oncogene,* 8:1407–1413, 1993.

Shay, J. W., *Mol. Med. Today,* 1:378–384, 1995.

Shippen-Lentz and Blackburn, "Functional evidence for an RNA template in telomerase," *Science,* 546–552, 1990.

Shippen-Lentz, D. and Blackburn, E. H., "Telomere terminal transferase activity from Euplotes crassus adds large numbers of TTTTGGGG repeats onto telomeric primers," *Mol Cell Biol.,* 9:2761–2764, 1989.

Stewart et al., "Gene transfer in vivo with DNA-liposome complexes: safety and acute toxicity in mice," *Human Gene Ther.,* 3:267–275, 1992.

Storm et al., "Potential pitfalls in in vitro antitumor activity testing of free and liposome-entrapped doxorubicin," *J. Pharm. Sci,* 77(10):823–830, 1988.

Strahl, C. and Blackburn, E. H., "The effects of nucleoside analogs on telomerase and telomeres in Tetrahymena," *Nucl. Acids Res.,* 22:893–900, 1994.

Strahl, C., and Blackburn, E. H., *Mol. and Cell. Biol.,* 16:53–65, 1996.

Tishkoff, D. X., Rockmill, B., Toeder, S., and Kolodner, T. D., *Genetics,* 139:495–509, 1995.

Vaziri et al., "Loss of telomeric DNA during aging of normal and trisomy 21 human lymphocytes," *Am. J. Hum. Genet.,* 52:661–667, 1993.

Watson, J. D., "Origin of concatameric T4 DNA," *Nature New Biol.,* 239:197–201, 1972.

Williamson, J. R., *Annu. Rev. Biomol. Struct.,* 23:703–730, 1994.

Wright et al., "Reversible Cell Senescence: Implications for immortalization of normal human diploid fibroblasts," *Mol. Cell Biol.,* 9:3088–3092, 1989.

Zahler, A. M. and Prescott, D. M., *Nucleic Acid Res.,* 16:6953–6972, 1988.

Zahler, A. M., Williamson, J. R., Cech, T. R., and Prescott, D. M., *Nature,* 350, 718–720, 1991.

Zakian, "Structure and function of telomeres," *Annu. Rev. Genet.,* 23:579–604, 1989.

What is claimed is:

1. A method of inhibiting cell growth in vitro, comprising contacting said cell with a compound or a salt thereof or a stereoisomer of said compound that has the formula (A) or (B):

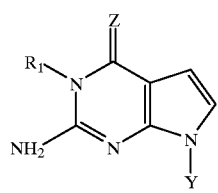

(A)

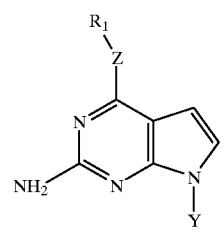

(B)

where $R_1$ is independently H, alkyl, arylalkyl, or aryl; Z is sulfur or oxygen; Y is independently H, alkyl, arylalkyl, aryl or acyclic or cyclic glycosyl groups represented by the formulae:

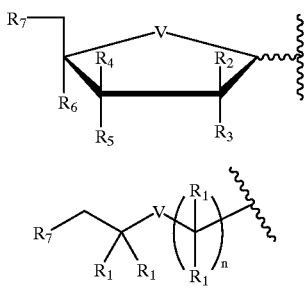

where $R_2$, $R_3$, $R_4$, $R_5$, are independently H, OH, halogen, amino or azido; provided that R3 and R5 may be unsubstituted when there is a double bond between the carbons bonded to $R_2$ and $R_4$; $R_6$ is independently H, alkylcarbonyl or arylcarbonyl; $R_7$ is independently OH, triphosphate, $PO(OR_8)_2$, $OP(O)(OR_8)_2$, $OP(O)(OR_9)(R_{10})$; $R_8$ is independently H, alkyl, aryl, or $CH_2C(O)$ alkyl; $R_9$ is independently H, alkyl, or aryl, and $R_{10}$ is independently an N-linked amino acid alkyl ester; N-linked amino acid arylalkyl ester, or N-linked amino acid aryl ester; V is independently sulfur, oxygen or methylene and n is 1–2.

2. The method of claim 1 wherein compound (B) has the formula:

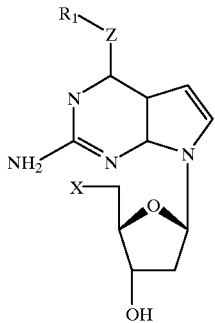

where Z is independently oxygen or sulfur; $R_1$ is independently H, alkyl, arylalkyl, or aryl and X is independently OH, triphosphate, $PO(OR_8)_2$, $OP(O)(OR_8)_2$, $OP(O)(OR_9)(R_{10})$; $R_8$ is independently H, alkyl, aryl, or $CH_2C(O)$-alkyl; $R_9$ is independently H, alkyl, or aryl, and $R_{10}$ is independently an N-linked amino acid alkyl ester; N-linked amino acid arylalkyl ester, or N-linked amino acid aryl ester.

3. A method of converting processive telomerase to non-processive telomerase in vitro comprising contacting telomerase containing cells in solution with an amount of 7-deaza nucleoside triphosphate sufficient to incorporate said triphosphate into telomeric DNA or by cleaving the telomerase RNA component.

4. The method of claim 1 wherein compound (B) is 1-methyl-7-deaza-2'-deoxyguanosine triphosphate, 6-methoxy-7-deaza-2'-deoxyguanosine triphosphate, or 6-thiomethyl-7-deaza-2'-deoxyguanosine triphosphate, or the corresponding nucleoside thereof.

5. The method of claim 1 wherein the cell is a mammalian cell.

6. The method of claim 1 wherein the cell is a human cell.

7. The method of claim 1 wherein the cell is a cancer cell.

8. A method of inhibiting telomerase activity in vitro, comprising contacting telomerase with an amount of deaza purine nucleotide in an amount sufficient to inhibit telomere extension.

9. The method of claim 1 wherein the inhibiting of cell growth leads to cell death.

10. The method of claim 8 wherein the 7-deaza nucleoside triphosphate is:

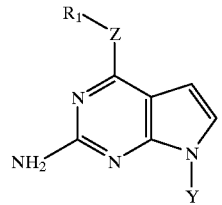

where Z is oxygen, $R_1$ is methyl, and Y is 2'-deoxy-5'-ribose triphosphate.

11. The method of claim 8 wherein the 7-deaza purine nucleoside or 7-deaza purine nucleotide is identified as

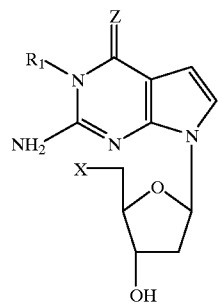

where Z is independently oxygen or sulfur; $R_1$ is independently H, alkyl, arylalkyl, or aryl and X is independently OH, triphosphate, $PO(OR_8)_2$, $OP(O)(OR_8)_2$, $OP(O)(OR_9)(R_{10})$; $R_8$ is independently H, alkyl, aryl, or $CH_2C(O)$ alkyl; $R_9$ is independently H, alkyl, or aryl, and $R_{10}$ is independently an N-linked amino acid alkyl ester; N-linked amino acid arylalkyl ester, or N-linked amino acid aryl ester.

12. The method of claim 3 where in the 7-deaza purine nucleoside or 7-deaza purine nucleotide is identified as

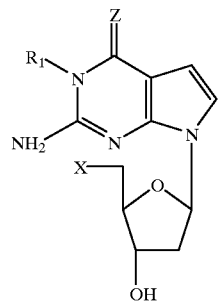

where Z is independently oxygen or sulfur; $R_1$ is independently H, alkyl, arylalkyl, or aryl and X is independently OH, triphosphate, $PO(OR_8)_2$, $OP(O)(OR_8)_2$, $OP(O)(OR_9)(R_{10})$; $R_8$ is independently H, alkyl, aryl, or $CH_2C(O)$ alkyl; $R_9$ is independently H, alkyl, or aryl, and $R_{10}$ is independently an N-linked amino acid alkyl ester; N-linked amino acid arylalkyl ester, or N-linked amino acid aryl ester.

13. The method of claim 7 wherein the cancer cell is ACF-7, MDA-231, BD-20, DU-145, PC3, SKBR3, Raji or CHO cells.
14. The method of claim 7 wherein the cancer cell is an embryonic kidney cell.
15. The method of claim 7 wherein the cancer cell is a human colon cancer cell.
16. The method of claim 8 wherein the 7-deaza nucleoside triphosphate has the structure:
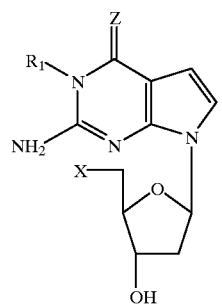
where Z is sulfur, $R_1$ is hydrogen and X is triphosphate.
* * * * *

UNITED STATES PATENT AND TRADEMARK OFFICE
CERTIFICATE OF CORRECTION

PATENT NO.   :   6,004,939

DATED        :   December 21, 1999

INVENTOR(S)  :   Shih-Fong Chen, Ira Maine, Sean M. Kerwin, Terace M. Fletcher, Miguel Salazar, Blain Mamiya, Makoto Wajima, and Bradford E. Windle It is certified that error appears in the above-identified patent and that said Letters Patent is hereby corrected as shown below:

Title Page, item [75], delete "Miquel" and insert --Miguel-- therefor.

Title Page, item [73], delete "CTRC Research Foundation Board of Regents, San Antonio, Tex.; The University of Texas System, Austin, Tex." and insert --CTRC Research Foundation, San Antonio, Tex.; Board of Regents, The University of Texas System, Austin, Tex.-- therefor.

UNITED STATES PATENT AND TRADEMARK OFFICE
CERTIFICATE OF CORRECTION

PATENT NO. : 6,004,939

DATED : December 21, 1999

INVENTOR(S) : Shih-Fong Chen, Ira Maine, Sean M. Kerwin, Terace M. Fletcher, Miguel Salazar, Blain Mamiya, Makoto Wajima, and Bradford E. Windle It is certified that error appears in the above-identified patent and that said Letters Patent is hereby corrected as shown below:

In claim 2, column 67, lines 27-39, delete the chemical formula and insert --

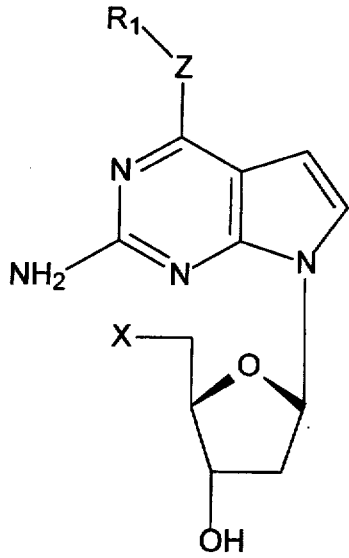

-- therefor.

UNITED STATES PATENT AND TRADEMARK OFFICE
CERTIFICATE OF CORRECTION

PATENT NO. : 6,004,939

DATED : December 21, 1999

INVENTOR(S) : Shih-Fong Chen, Ira Maine, Sean M. Kerwin, Terace M. Fletcher, Miguel Salazar, Blain Mamiya, Makoto Wajima, and Bradford E. Windle It is certified that error appears in the above-identified patent and that said Letters Patent is hereby corrected as shown below:

Claim 8, column 67, line 65, delete "deaza" and insert --7 deaza purine nucleoside or 7-deaza-- therefor.

Signed and Sealed this

Eighth Day of August, 2000

Attest:

Q. TODD DICKINSON

Attesting Officer

Director of Patents and Trademarks

SEQUENCE LISTING (1) GENERAL INFORMATION:

(iii) NUMBER OF SEQUENCES: 4

(2) INFORMATION FOR SEQ ID NO:1:

```
        (i) SEQUENCE CHARACTERISTICS:
            (A) LENGTH: 9 base pairs
            (B) TYPE: nucleic acid
            (C) STRANDEDNESS: single
            (D) TOPOLOGY: linear (xi) SEQUENCE DESCRIPTION: SEQ ID NO:1:

CAACCCCAA                                                                   9

(2) INFORMATION FOR SEQ ID NO:2:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:2:

CAAAACCCCA AAACC                                                           15

(2) INFORMATION FOR SEQ ID NO:3:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:3:

TTAGGGTTAG GGTTAGGG                                                        18

(2) INFORMATION FOR SEQ ID NO:4:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ix) FEATURE:
            (A) NAME/KEY: modified_base
            (B) LOCATION: 7
            (D) OTHER INFORMATION: /mod_base= OTHER
                /note= "N = G or 7-deaza-G"

(xi) SEQUENCE DESCRIPTION: SEQ ID NO:4:

GGTTAGNGTT AT                                                              12
```